US012276654B2

(12) United States Patent
Moellering et al.

(10) Patent No.: US 12,276,654 B2
(45) Date of Patent: Apr. 15, 2025

(54) CHEMICAL PROBE-DEPENDENT EVALUATION OF PROTEIN ACTIVITY AND USES THEREOF

(71) Applicant: The University of Chicago, Chicago, IL (US)

(72) Inventors: Raymond E. Moellering, Chicago, IL (US); Gang Li, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1207 days.

(21) Appl. No.: 15/733,113

(22) PCT Filed: Nov. 21, 2018

(86) PCT No.: PCT/US2018/062231
§ 371 (c)(1),
(2) Date: May 19, 2020

(87) PCT Pub. No.: WO2019/104155
PCT Pub. Date: May 31, 2019

(65) Prior Publication Data
US 2020/0355673 A1    Nov. 12, 2020

Related U.S. Application Data

(60) Provisional application No. 62/589,946, filed on Nov. 22, 2017.

(51) Int. Cl.
*G01N 33/50* (2006.01)
*A61K 31/7088* (2006.01)
(Continued)

(52) U.S. Cl.
CPC ..... *G01N 33/5035* (2013.01); *A61K 31/7088* (2013.01); *C07K 14/003* (2013.01);
(Continued)

(58) Field of Classification Search
CPC ............... C12Q 1/6841; C12Q 1/6804; C12Q 2525/125; C12Q 2563/179
See application file for complete search history.

(56) References Cited

U.S. PATENT DOCUMENTS 7,306,904 B2   12/2007   Landegren et al.
8,940,497 B2    1/2015   Cravatt et al.
(Continued)

FOREIGN PATENT DOCUMENTS

| WO | WO 2012/006556 | 1/2012 | |
|---|---|---|---|
| WO | WO-2015175856 A1 * | 11/2015 | ........... C12Q 1/6832 |
| WO | WO 2017/192633 | 11/2017 | |

OTHER PUBLICATIONS

Schedin-Weiss et al. PLOS ONE. 2013. 8(5):e63962. (Year: 2013).*
(Continued)

*Primary Examiner* — Joseph G. Dauner
(74) *Attorney, Agent, or Firm* — Norton Rose Fulbright US LLP

(57) ABSTRACT

Disclosed, in part, are methods and compositions for evaluating two or more target proteins from the same family through the use of a molecular construct that contains a targeting group and a retrieval tag. The method can, in some aspects, quantify the activity and function of the proteins of interest, visualize active enzymes at the subcellular and intercellular scale, and increase dynamic range via signal amplification.

20 Claims, 38 Drawing Sheets

Specification includes a Sequence Listing.

(51) Int. Cl.
  C07K 14/00 (2006.01)
  C07K 16/44 (2006.01)
  C12P 19/34 (2006.01)
  G01N 33/542 (2006.01)
(52) U.S. Cl.
  CPC .............. *C07K 16/44* (2013.01); *C12P 19/34* (2013.01); *G01N 33/542* (2013.01); *C07K 2317/622* (2013.01); *C07K 2318/20* (2013.01); *G01N 2458/10* (2013.01)

(56) References Cited

U.S. PATENT DOCUMENTS

2002/0064779 A1  5/2002  Landegren et al.
2011/0143955 A1  6/2011  Weiner

OTHER PUBLICATIONS

Fredriksson et al. Nature Methods. 2007. 4(4):327. (Year: 2007).*
Chang et al., "A Potent and Selective Inhibitor of KIAA1363/AADACL1 that Impairs Prostate Cancer Pathogenesis," Chemistry & Biology 18, pp. 476-484 (2011).
Extended European Search Report and Opinion for EP 18880198.9 issued Oct. 26, 2021.
Jessani et al., "A streamlined platform for high-content functional proteomics of primary human specimens," Nature Methods 2:9, pp. 691-697 (2005).
Jessani et al., "Enzyme activity profiles of the secreted and membrane proteome that depict cancer cell invasiveness," PNAS 99:16, pp. 10335-10340 (2002).
Li et al., "A Concise, Modular Antibody-Oligonucleotide Conjugation Strategy Based on Disuccinimidyl Ester Activation Chemistry," ChemBioChem 20, pp. 1-8 (2019).
Nomura et al., "Monoacylglycerol Lipase Exerts Dual Control over Endocannabinoid and Fatty Acid Pathways to Support Prostate Cancer", Chemistry & Biology 18, pp. 846-856 (2011).
Kidd et al., "Profiling Serine Hydrolase Activities in Complex Proteomes" *Biochemistry* 2001, 40, 4005-4015.
Liu et al., "Activity-based protein profiling: The serine hydrolases" *PNAS* 1999, 96(26), 14694-14699.
Partial Supplementary European Search Report issued in corresponding European application No. 18880198.9, dated Jul. 14, 2021.
Chang et al., "An activity-based imaging probe for the integral membrane hydrolase KIAA1363." *Angew Chem Int Ed Engl* 2012, 51, 966-970.
Elfineh, L., et al., "Tyrosine phosphorylation profiling via in situ proximity ligation assay." *BMC cancer* 2014, 14(435), 9 pages.

Fonović, M. & M. Bogyo, "Activity Based Probes as a tool for Functional Proteomic Analysis of Proteases" *Expert Rev Proteomics* 2008, 5(5): 721-730.
Fredriksson, S., et al., "Protein detection using proximity-dependent DNA ligation assays." *Nature Biotechnology* 2002, 20, 473-477.
Gajadhar, A. & Guha, A., "A proximity ligation assay using transiently transfected, epitope-tagged proteins: application for in situ detection of dimerized receptor tyrosine kinases." *Bio Techniques* 2010, 48, 145-152.
Gao, X. & Hannoush, R.N., "Single-cell in situ imaging of palmitoylation in fatty-acylated proteins." *Nature Protocols* 2014, 9, 2607-2623.
Greenwood et al., "Proximity assays for sensitive quantification of proteins" Biomolecular Detection and Quantification 2015, 4, 10-16.
Gu, G.J., et al., "Protein tag-mediated conjugation of oligonucleotides to recombinant affinity binders for proximity ligation." *New Biotechnology* 2013, 30, 144-152.
International Search Report and Written Opinion issued in Corresponding PCT Application No. PCT/US2018/062231, dated Apr. 16, 2019.
Kim et al., "A DNA-assisted immunoassay for enzyme activity via a DNA-linked, activity-based probe" Chem. Commun. 2017, 53, 9474-9477.
Li et al., "An activity-dependent proximity ligation platform for spatially resolved quantification of active enzymes in single cells" Nature Communications 2017, 8(1775), 1-12.
Lundberg et al., "Multiplexed Homogeneous Proximity Ligation Assays for High-throughput Protein Biomarker Research in Serological Material" *Molecular& Cellular Proteomics* 2011, 10.4, 11 pages.
Nomura et al., "Activity-based protein profiling for biochemical pathway discovery in cancer" Nat Rev Cancer 2010, 10(9), 630-638.
Robinson et al., "Glyco-seek: Ultrasensitive Detection of Protein-Specific Glycosylation by Proximity Ligation Polymerase Chain Reaction." *Journal of the American Chemical Society* 2016, 138, 10722-10725.
Robinson et al., "Live-Cell Labeling of Specific Protein Glycoforms by Proximity-Enhanced Bioorthogonal Ligation." *Journal of the American Chemical Society* 2015, 137, 10452-10455.
Schedin-Weiss et al., "Visualizing Active Enzyme Complexes Using a Photoreactive Inhibitor for Proximity Ligation—Application on γ-Secretase" PloS One 2012, 8(5), e63962, 1-10.
Soderberg, O., et al., "Direct observation of individual endogenous protein complexes in situ by proximity ligation." *Nature Methods* 2006, 3, 995-1000.
Thompson et al., "SH2-PLA: a sensitive in-solution approach for quantification of modular domain binding by proximity ligation and real-time PCR" BMC Biotechnology 2015, 15(60), 1-13.

* cited by examiner

| Enzyme family with active group | General probe structure with warhead group |
|---|---|
|  Metalloproteases | 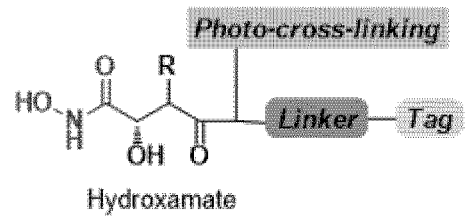 Hydroxamate |
|  β-retaining glycosidases | 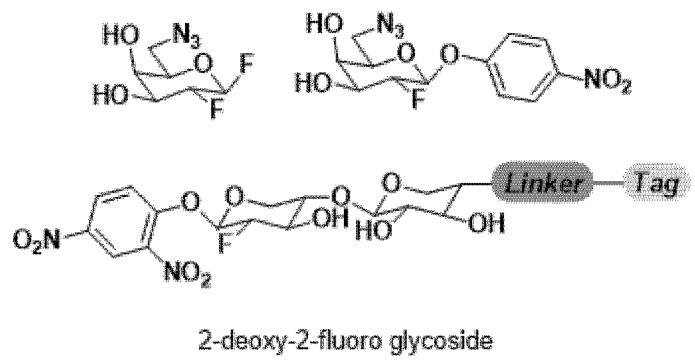 2-deoxy-2-fluoro glycoside |
|  Tyrosine phosphatases | 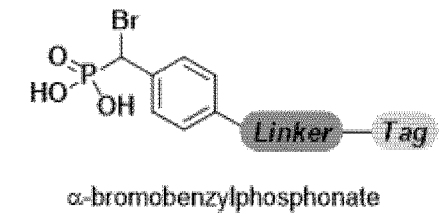 α-bromobenzylphosphonate |
|  Cytochrome P450s | 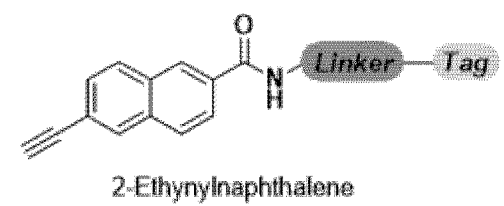 2-Ethynylnaphthalene |
FIG. 13B

| Retrieval tag structure | Retrieval partner |
|---|---|
| 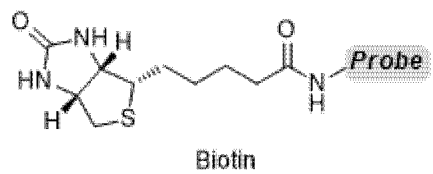 Biotin | 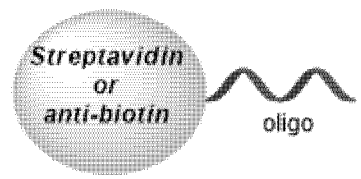 |
| 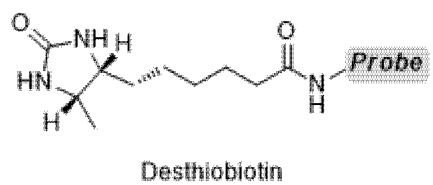 Desthiobiotin | 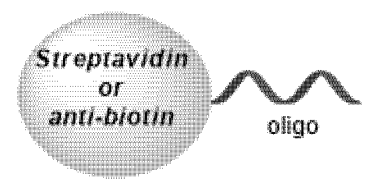 |
| 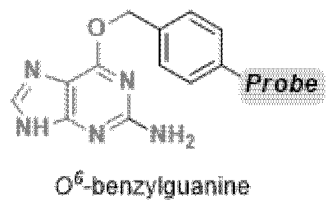 O$^6$-benzylguanine |  |
| 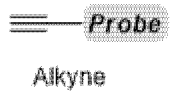 Alkyne |  |
| 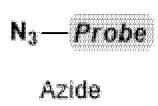 Azide | 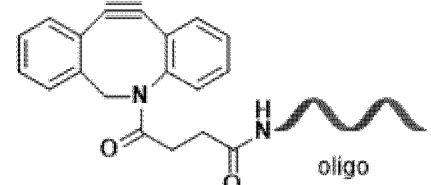 |
| 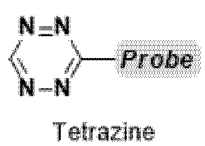 Tetrazine | 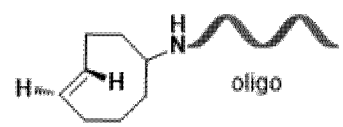 |
FIG. 14

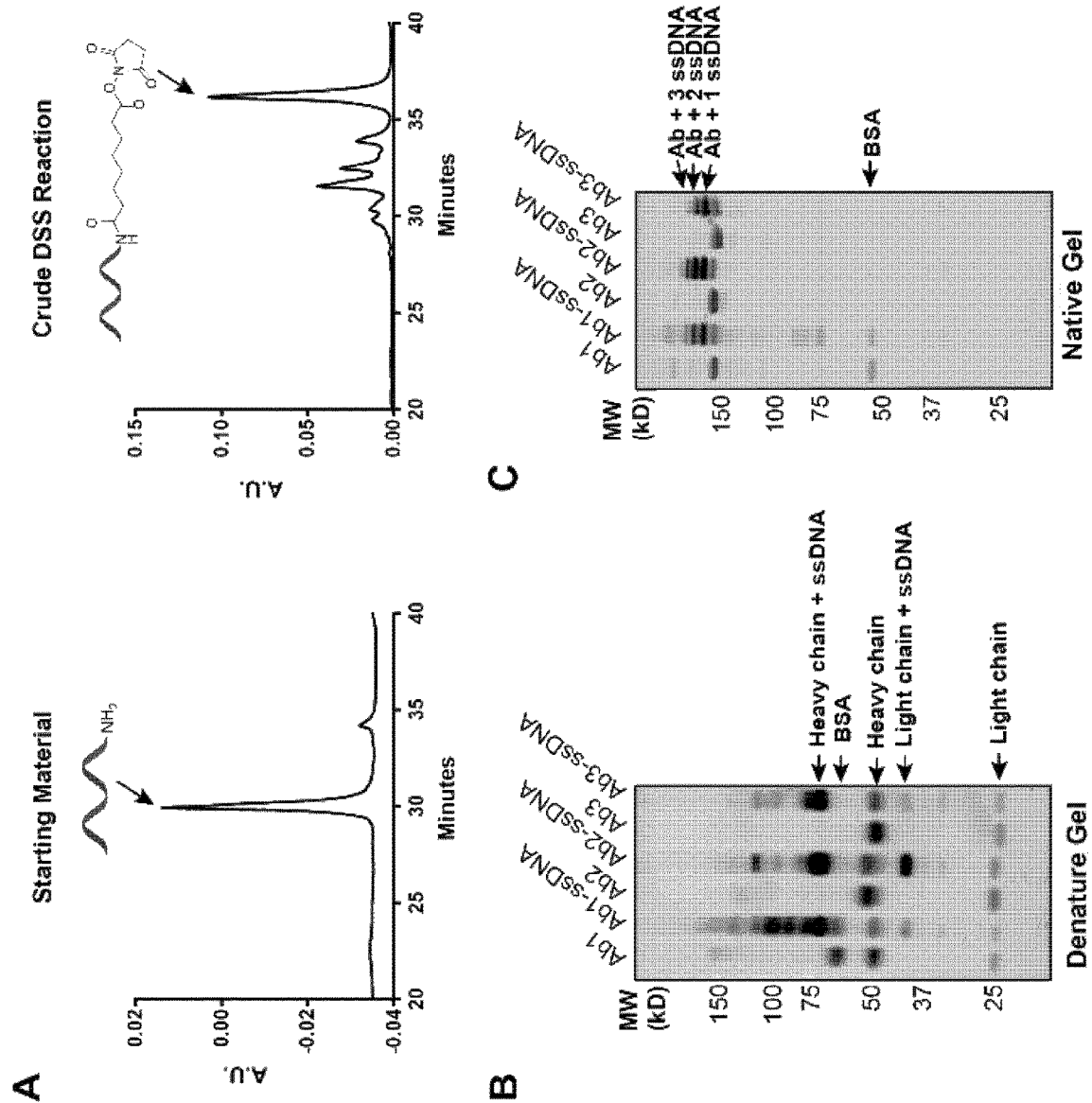
FIG. 16A-C

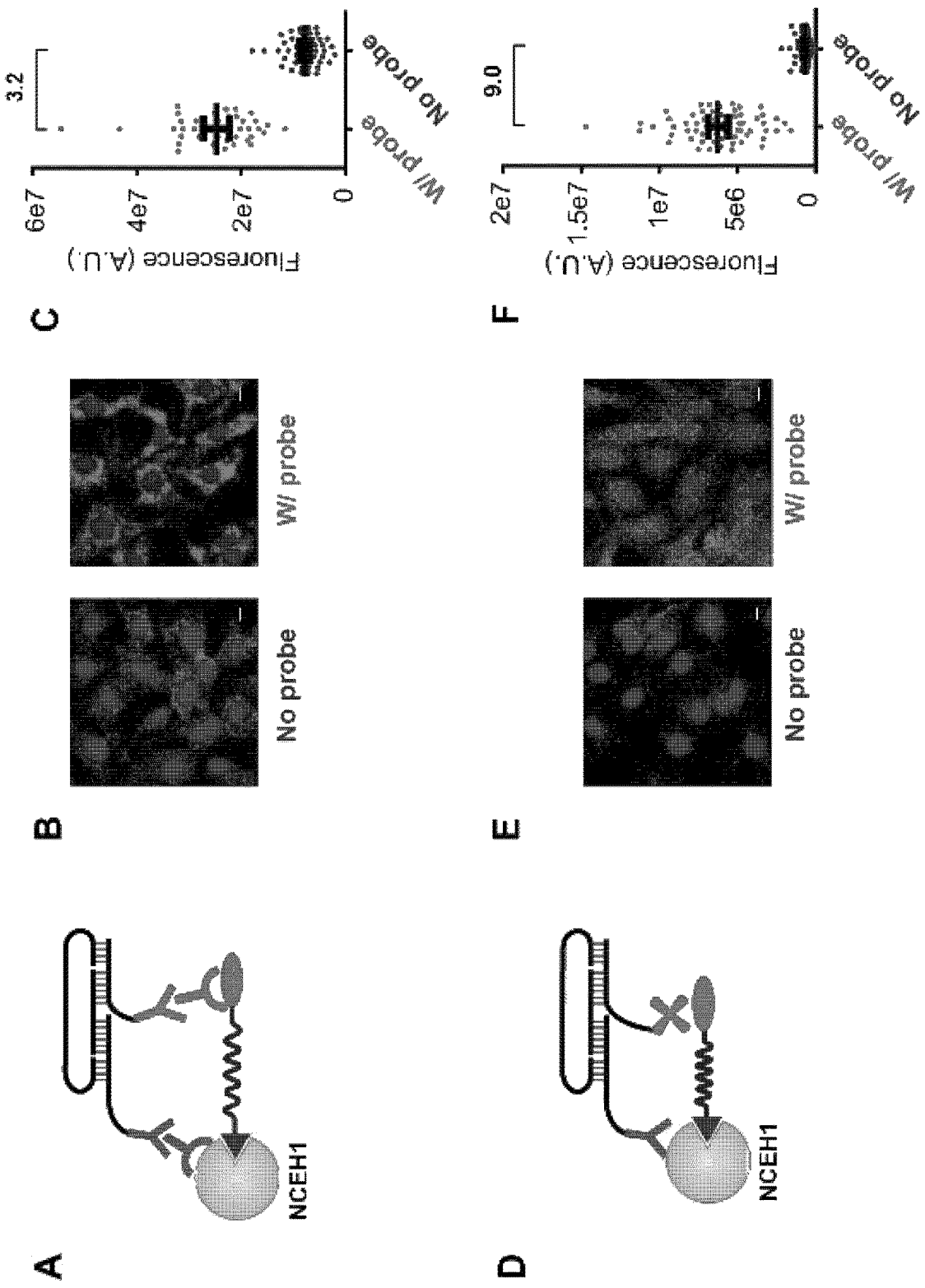
FIG. 17A-F

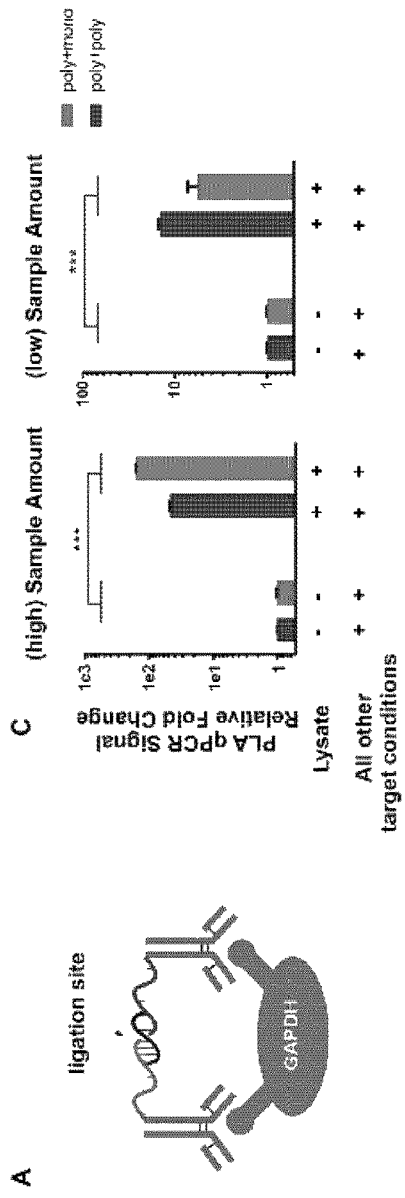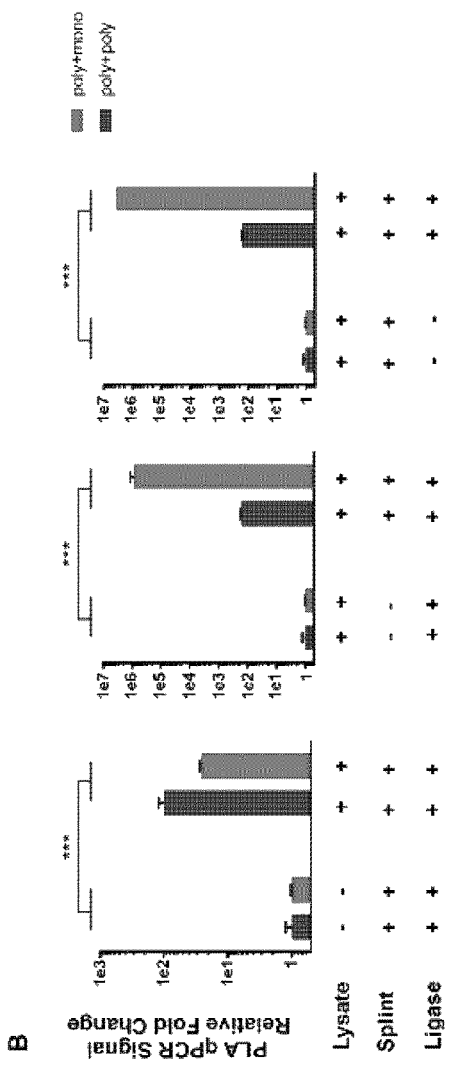
FIG. 18A-D

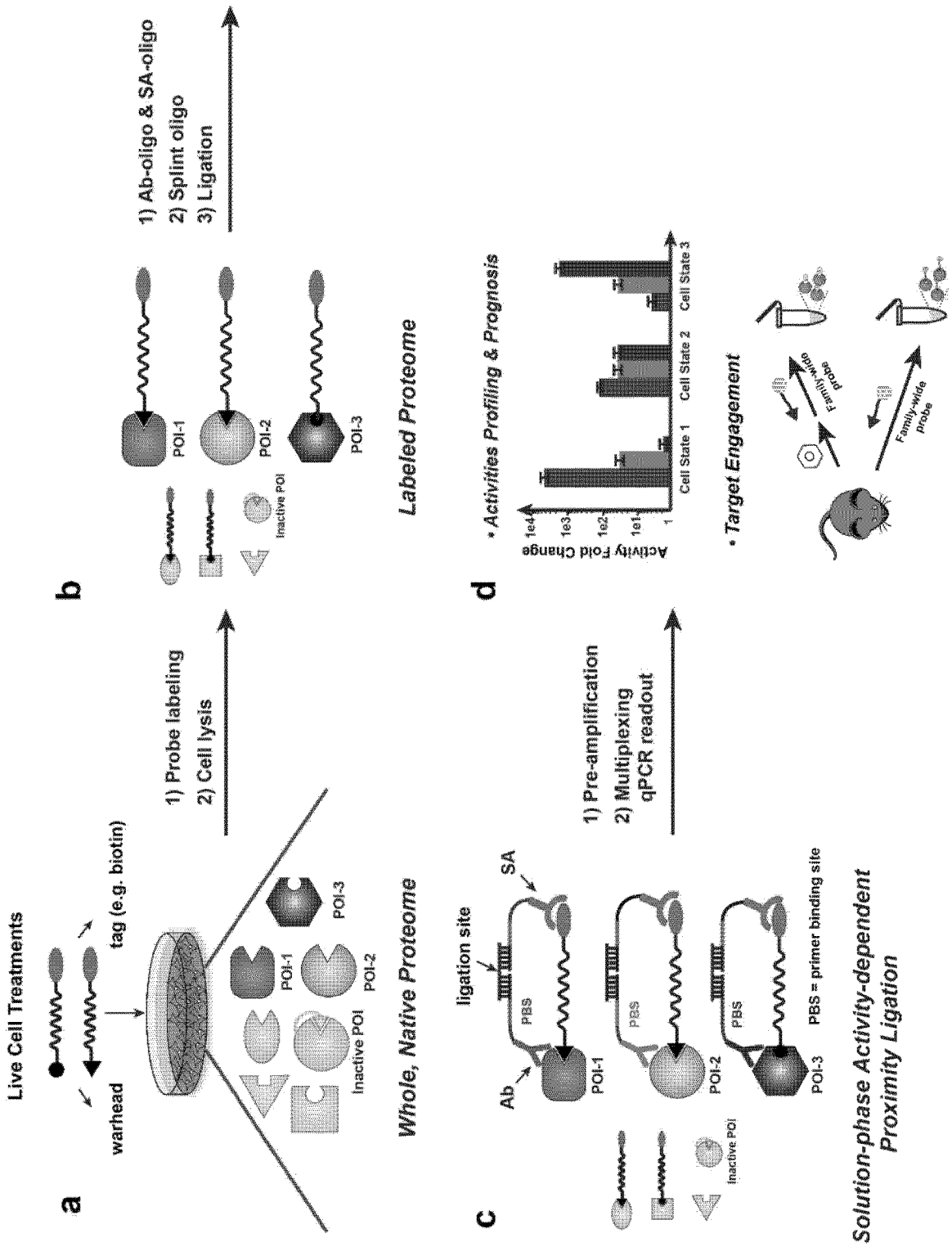
FIG. 19A-D

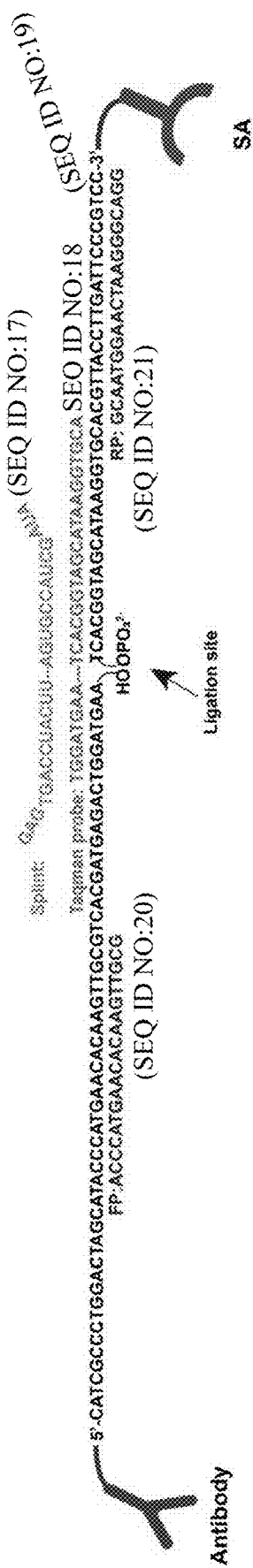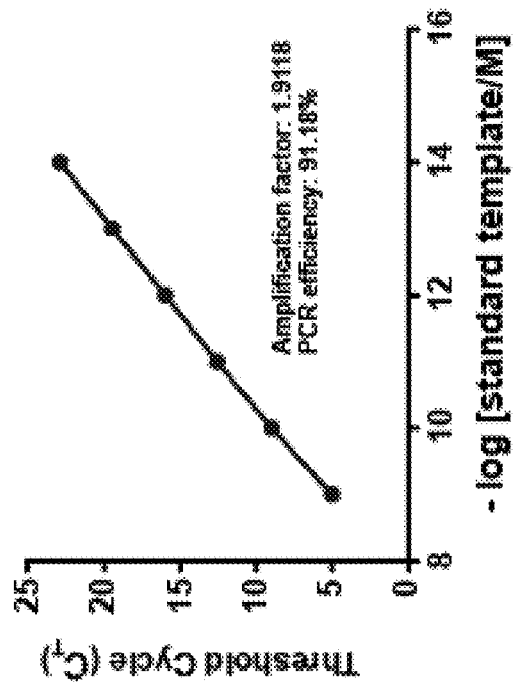
FIG. 20

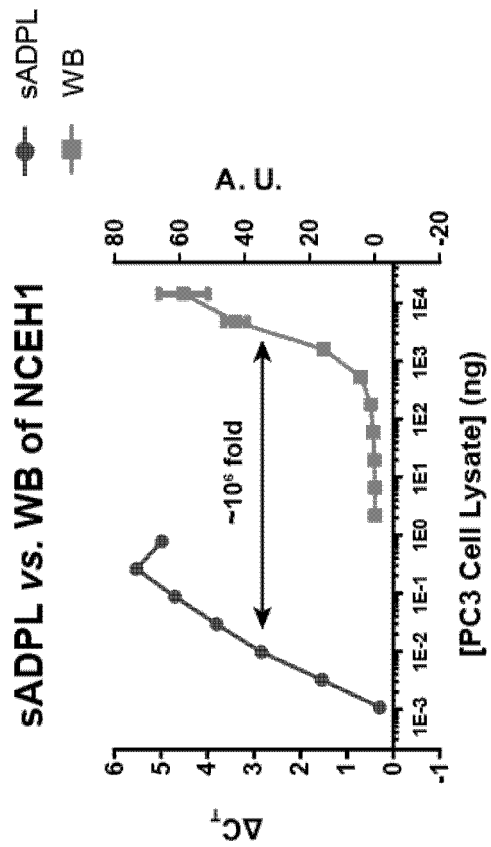
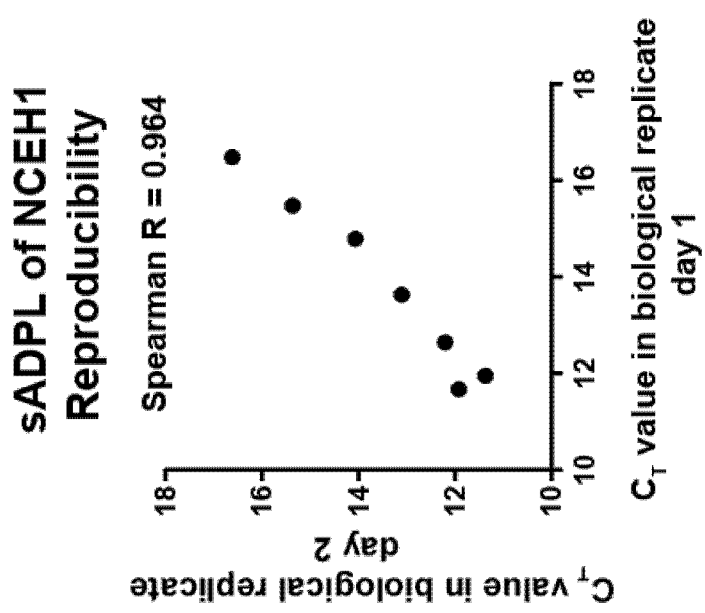
FIG. 22

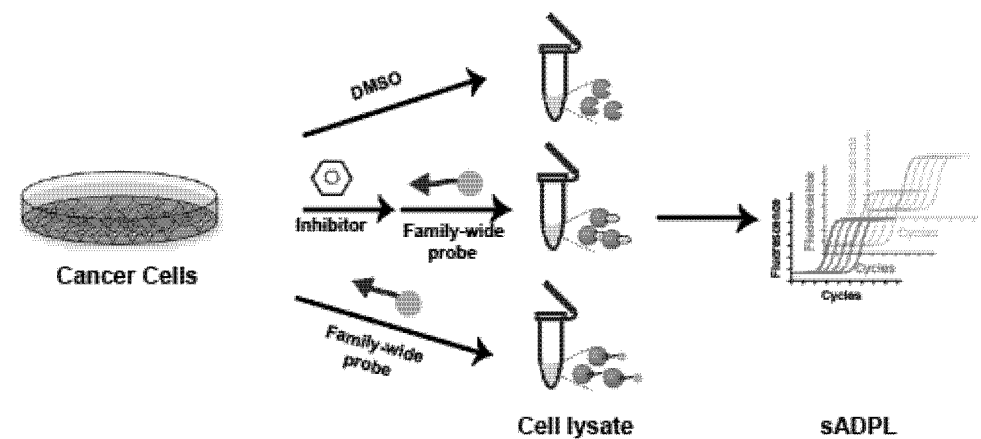
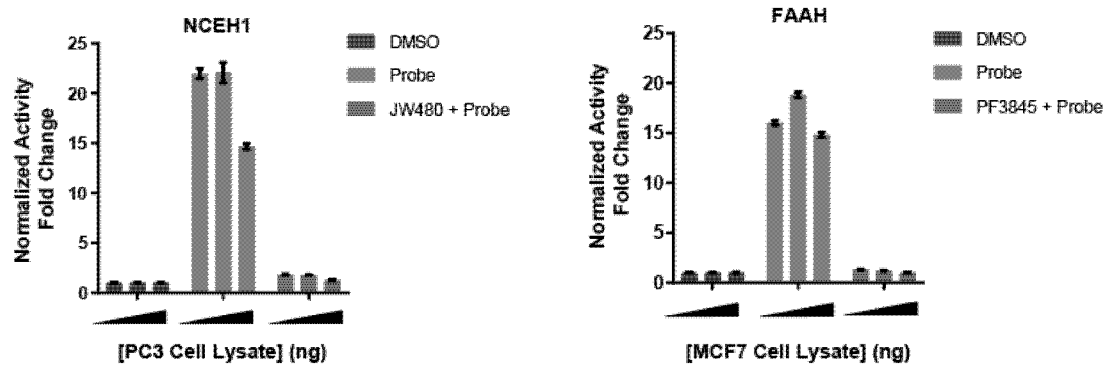
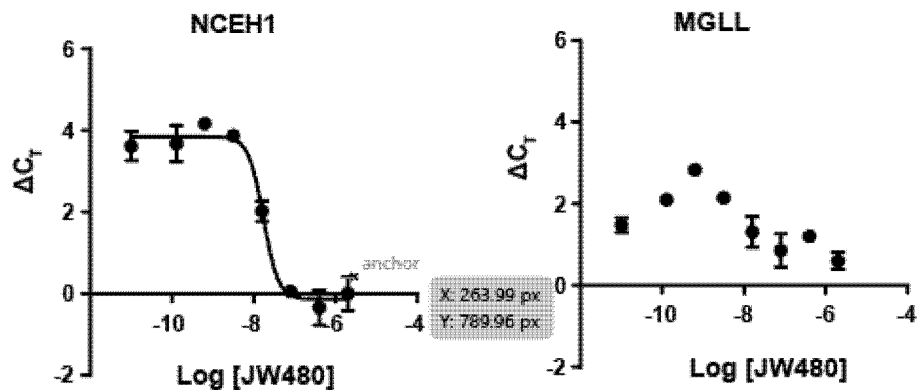
FIG. 23

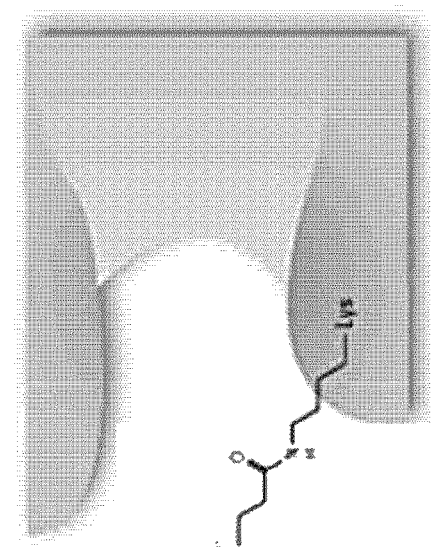
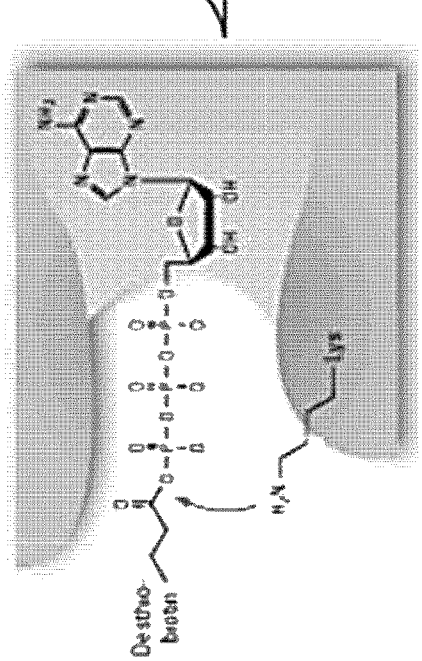
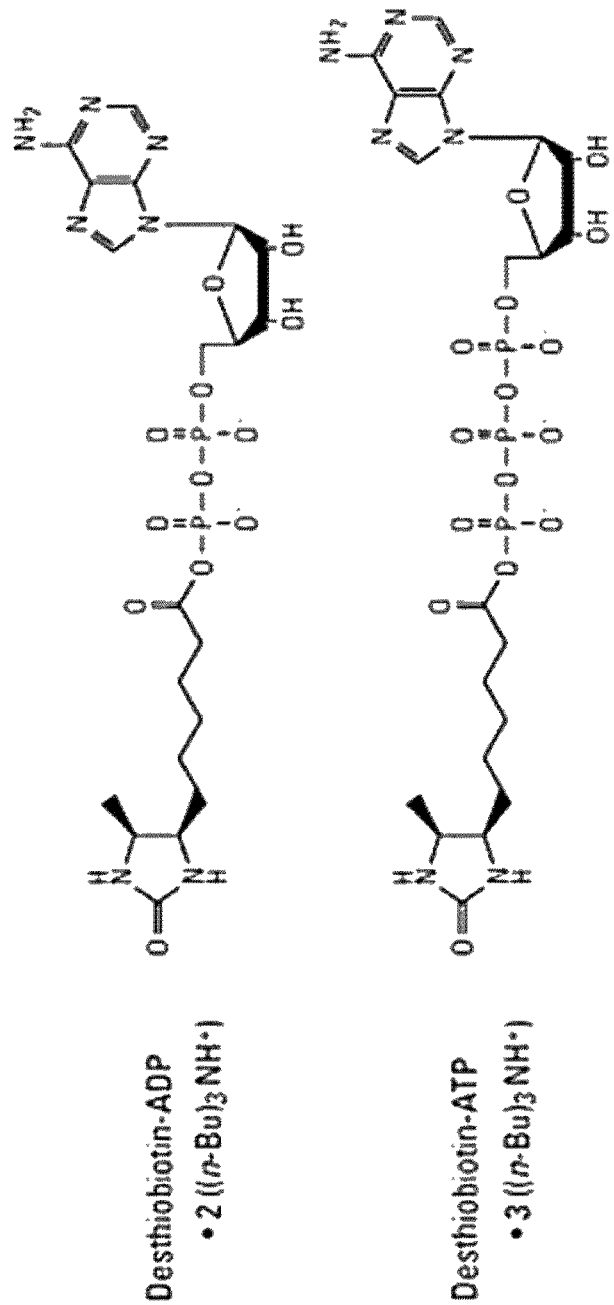
FIG. 35A-B

CHEMICAL PROBE-DEPENDENT EVALUATION OF PROTEIN ACTIVITY AND USES THEREOF

CROSS-REFERENCE TO RELATED APPLICATIONS

This application is a national phase application under 35 U.S.C. § 371 of International Application No. PCT/US2018/062231 filed Nov. 21, 2018, which claims the benefit of priority of U.S. Provisional Patent Application No. 62/589,946 filed Nov. 22, 2017, all of which are hereby incorporated by reference in their entirety.

This invention was made with government support under grant numbers CA175399 and GM128199 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 30, 2024, is named ARCDP0646US_ST25.txt and is 4,864 bytes in size.

BACKGROUND

1. Field of the Invention

The current disclosure relates to the field of molecular biology, therapeutic methods, and diagnostics.

2. Description of Related Art

The study of protein function has traditionally been a reductionist endeavor, where proteins are expressed and purified from orthogonal hosts and then studied in isolation. However, the functional properties of a protein are imparted by the complexity of the surrounding environment, including participation in protein-protein complexes, spatial localization to distinct sub-cellular compartments, post-translational chemical modifications and even mechanical forces within or between cells. Despite our appreciation for these influences, traditional biophysical and biochemical techniques rarely capture the effects of these events. The field of proteomics aims to provide a comprehensive accounting of the complement of proteins in a biological sample. In the decade since orbitrap mass spectrometers and analysis algorithms have become commercially available, the field of proteomics has found mainstream applications in basic chemical, biological and clinical research. Despite the power of these technologies, standard proteomic platforms are typically limited to providing two pieces of information: whether a specific protein is present in a sample, and the relative abundance of a protein within a sample. While this information is important, it does not provide information on the functional state of the detected proteins. Activity-based proteomic technologies, on the other hand, integrate enzyme- or protein-family specific chemical probes with traditional mass spectrometry or gel-based profiling methods in order to detect and quantify protein activity, rather than abundance. These measurements can be made directly with complex samples such as lysate, tissues and biological fluids to measure changes in protein activity, often for entire families of proteins of a hundred or more, that result from endogenous biological signals or the action of exogenous molecules (e.g., therapeutics).

Activity-based profiling approaches and the mass spectrometry platforms upon which they rely have two major limitations. First, gel-based or mass spectrometry-based proteomic experiments impose significant limits on the amount of sample needed, which generally prevents the analysis of limited abundance samples (e.g., patient tissue) and single cell measurements. Even with ample input proteome, gel-based and data-dependent LC-MS/MS measurements are heavily biased toward high abundance proteins, often omitting a majority of the proteome in routine analyses. CyTOF and imaging mass spectrometry approaches can provide quantitative information on protein abundance with single-cell resolution, however these approaches require expensive mass spectrometry equipment and antibody conjugates, and do not report on protein function. Second, current proteomic methods require homogenization and manipulation of the biological sample, which results in the loss of spatial information about protein activity, both at intra- and intercellular levels. Expression of fluorescent protein-tagged proteins or the use of proximity ligation assays targeting complexes or modified forms of a protein of interest can provide information on sub-cellular localization, however these approaches often require genetic manipulation, availability of multiple proteoform-specific antibodies, and a priori information correlating functional state with specific proteoforms of a protein. Activity-based probes detect protein activity, but involve loss of spatial information and require significant input proteome. Small molecule "turn-on" probes typically lack the ability to provide precise spatial information due to signal diffusion, and sometimes do not reflect activity of a single protein but a protein family. Several recent studies have applied iterative medicinal chemistry and screening to transform non-selective family-wide probes into enzyme-specific reporter probes for lipid hydrolases and caspase-family cysteine proteases. Through the covalent tagging of active enzymes with a fluorescent reporter, these probes have enabled sub-cellular and inter-cellular visualization and quantification of active enzymes, in live cells and in vivo. While providing a step forward in chemical proteomics, like "turn-on" probes this approach is hardly general, as each enzyme requires de novo development of tailored chemical probes that exhibit extremely high target selectivity. Therefore, there is a need in the art for methods to study the activity profile of native proteins in their natural environment.

SUMMARY OF THE DISCLOSURE

The current disclosure overcomes the limitations of known assays by providing a novel platform that provides three features typically absent in proteomic profiling: 1) Quantification of protein activity and function, rather than abundance; 2) Direct visualization of localized enzyme activity at the sub-cellular and intercellular scale; and 3) Increased dynamic range through signal amplification to allow measurement of low abundance proteins and samples. Aspects of the disclosure relate to a method for evaluating two or more target proteins of interest from the same family in a specified functional form, the method comprising: (i) contacting a composition comprising or suspected of comprising the two or more proteins of interest with a molecular construct comprising: a targeting group operatively linked to a retrieval tag; wherein the targeting group specifically binds to the specialized functional form of the two or more target proteins of interest; (ii) contacting the composition with at least two antibody-oligo constructs, wherein at least one of the constructs comprises a first antibody operatively linked to a first oligo and at least a second construct comprises a second antibody operatively linked to a second oligo; wherein the first antibody specifically binds to one of the two or more target proteins of interest and the second antibody specifically binds to the other of the two or more target proteins of interest; (iii) contacting the composition with a second molecular construct comprising a retrieval tag binder operatively linked to a retrieval oligo; (iv) incubating the composition under conditions sufficient for the ligation or annealing of the first oligo to the retrieval oligo when the first and retrieval oligos are in close proximity to each other and ligation or annealing of the second oligo to the retrieval oligo when the second and retrieval oligos are in close proximity to each other; and (v) detecting the ligated or annealed first and retrieval oligo and the ligated or annealed second and retrieval oligo.

Further aspects of the disclosure relate to a method for evaluating two or more target proteins of interest from the same family in a specified functional form, the method comprising: (i) contacting a composition comprising or suspected of comprising the two or more proteins of interest with a molecular construct comprising: a targeting group operatively linked to a retrieval tag; wherein the targeting group specifically binds to the specialized functional form of the two or more target proteins of interest; (ii) contacting the composition with a second molecular construct comprising a retrieval tag binder operatively linked to a solid support; wherein the retrieval tag binder and retrieval tag association operatively links the specialized functional form of the two or more target proteins of interest to the solid support; (iii) washing the solid support to remove unlinked proteins; (iv) contacting the composition with at least two antibody-oligo constructs, wherein at least one of the constructs comprises a first antibody operatively linked to a first oligo and at least a second construct comprises a second antibody operatively linked to a second oligo; wherein the first antibody specifically binds to one of the two or more target proteins of interest and the second antibody specifically binds to the other of the two or more target proteins of interest; and (v) detecting the first and second oligo.

In some embodiments, the solid support comprises a polymer, a bead, a microplate, a chip, glass, or plastic. In some embodiments, washing the solid support comprises contacting the solid support with an aqueous solution, followed by separation of aqueous components from the solid support. In some embodiments, step (iii), washing the solid support to remove unlinked proteins is performed more than one time, such as at least 2, 3, 4, or 5 times. In some embodiments, step (iii), washing the solid support to remove unlinked proteins is after step (iv), contacting the composition with at least two antibody-oligo constructs, wherein at least one of the constructs comprises a first antibody operatively linked to a first oligo and at least a second construct comprises a second antibody operatively linked to a second oligo; wherein the first antibody specifically binds to one of the two or more target proteins of interest and the second antibody specifically binds to the other of the two or more target proteins of interest.

The term family can refer to proteins that harbor the same potential for a specific catalytic mechanism and/or proteins that share unique chemical reactivity imparted by shared structural features.

The term "specified functional form" refers to a form or state of the protein that performs a particular function and/or is considered an active state. In some embodiments, the specified functional form is an active form of the protein. In some embodiments, the specified functional form is an active form of the protein that can/is capable of acting as a catalyst in an enzymatic reaction.

Further aspects of the disclosure relate to a method of evaluating a protein of interest in a patient in a specified functional form, said method comprising: (i) contacting a biological sample from the patient with a molecular construct comprising: a targeting group operatively linked to a retrieval tag; wherein the targeting group specifically binds to the specified functional form of the protein of interest; (ii) contacting the composition with an antibody operatively linked to a first oligo; wherein the antibody specifically binds to the protein of interest; (iii) contacting the composition with a second molecular construct comprising a retrieval tag binder operatively linked to a retrieval oligo; (iv) incubating the composition under conditions sufficient for the ligation or annealing of the first oligo to the retrieval oligo when the first and retrieval oligos are in close proximity to each other; (v) detecting the ligated or annealed first and retrieval oligos. In specific embodiments, the protein of interest comprises NCEH1. In further embodiments, the protein of interest comprises FAAH and/or CTSB. In certain embodiments, the specified functional form is an active form of the protein, such as one that can catalyze an enzymatic reaction.

Further aspects relate to a molecular construct comprising: a targeting group operatively linked to a retrieval tag.

In further embodiments, the activity of more than two proteins may be evaluated, such as n proteins of interest. Such methods further include; contacting the composition with an nth antibody operatively linked to an nth oligo, wherein n is any integer greater than 1, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 220, 230, 240, 250, 260, 270, 280, 290, 300, 325, 350, 375, 400, 450, 500, 550, 600 (or any derivable range therein). In this case, step (iv) includes ligation or annealing of the nth oligo to the retrieval oligo when the nth oligo and retrieval oligos are in close proximity to each other and ligation or annealing of the second oligo to the retrieval oligo when the second and retrieval oligos are in close proximity to each other; and (v) detecting each ligated or annealed nth and retrieval oligo. In some embodiments the two (or n number of proteins) or more target proteins of interest are enzymes.

In the embodiments of the disclosure, particularly those relating to a first or second oligo, antibody, primer, or probe, first or second may be further extended to nth, wherein n is an integer greater than two. Therefore, when nth=$8^{th}$, the methods include a first, second, third, fourth, fifth, sixth, seventh, and eighth antibody, oligo, primer, probe, etc. . . .

In some embodiments, the method further comprises determining the abundance of each of the two or more target proteins of interest in the specialized functional form. In some embodiments, determining the abundance of protein in a specialized functional form comprises PCR amplification of the ligated first and retrieval oligo and of the ligated second and retrieval oligo. In some embodiments, determining the abundance of protein in a specialized functional form comprises primer extension and/or PCR amplification of the annealed first and retrieval oligo and of the annealed second and retrieval oligo. For example, when the first, second, or nth oligo is in close proximity with the retrieval oligo, they may be constructed so that a proximity extension assay can be performed. The proximity of the two oligos creates a real-time PCR amplicon in a proximity-dependent manner enabled by the action of a DNA polymerase (eg. 3'Exonuclease-capable polymerase). In some embodiments, (i)-(v) are performed in chronological order. In some embodiments, the retrieval tag is covalently linked to the targeting group. In some embodiments, the retrieval tag is covalently linked to the targeting group through a linker. In some embodiments, the linker is an organic linker. In some embodiments, the linker comprises an aliphatic linker. In some embodiments, the linker comprises a hydrocarbon chain of 3-20 carbon atoms. In some embodiments, the linker comprises a hydrocarbon chain of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) carbon atoms. In some embodiments, the first antibody is covalently linked to a first oligo and/or the second antibody is covalently linked to a second oligo.

In some embodiments, the first antibody and/or second antibody is operatively linked to a first and/or second oligo, respectively, through a non-covalently bound secondary antibody, wherein the non-covalently bound secondary antibody is covalently linked to the first or second oligo. In some embodiments, the first antibody operatively linked to the first oligo and/or the second antibody operatively linked to the second oligo comprises a molecular label. In some embodiments, the molecular label comprises a fluorescent molecule. In some embodiments, the first, second, and/or retrieval oligos are single-stranded oligos.

In some embodiments, step (ii) further comprises contacting the composition with one or more bridging oligos, wherein at least one of the one or more bridging oligos comprises complementary regions to both the first oligo and the retrieval oligo and at least one of the one or more bridging oligos comprises complementary regions to both the second oligo and the retrieval oligo. In some embodiments, the method further comprises performing rolling circle amplification after step (iv). In some embodiments, the method further comprises hybridization chain reaction.

In some embodiments, the methods include a method step described herein. Such method step may be performed before or after step (i), (ii), (iii), (iv), and/or (iv).

In some embodiments, the first and/or second oligo comprises a barcode. In some embodiments, the method further comprises contacting the composition with a first labeled primer and/or second labeled primer, wherein the first labeled primer is specifically complementary to the first oligo and non-complementary to the second oligo and the second labeled primer is specifically complementary to the second oligo and non-complementary to the first oligo. In some embodiments, the first labeled primer and/or second labeled primer is complementary to a barcode. In some embodiments, the first labeled primer and second labeled primer are labeled with differentially detectable molecular labels. The term "differentially detectable" refers to two labels that can be quantitatively and/or qualitatively detected at the same time when the two labels are intermixed in the same composition and/or microscopically visualized within the same cells.

In some embodiments, the composition in (i) comprises cells or an extract or fraction thereof. In some embodiments, the composition in (i) comprises live cells. In some embodiments, the methods may further comprise fixation (e.g., by utilizing a fixative such as formalin) of the cells and/or lysis of the cells. In some embodiments, the fixation and or lysis is performed after method step (i). In some embodiments, the method further comprises spatially detecting the specialized functional form of the two or more target proteins of interest. In some embodiments, the proteins of interest are spatially detected within a cell and/or organelle of a cell. In some embodiments, the two or more target proteins of interest are non-modified proteins and/or are expressed from endogenous non-genetically modified genes. In some embodiments, the probe covalently modifies, or is capable of covalently modifying both or all of the two or more target proteins of interest.

In some embodiments, the composition comprises less than 5000 cells. In some embodiments, the composition comprises less than 1000000, 900000, 800000, 700000, 600000, 500000, 400000, 300000, 200000, 100000, 90000, 80000, 70000, 60000, 50000, 40000, 30000, 20000, 10000, 9000, 8000, 7000, 6000, 5000, 4000, 3000, 2000, 1000, 500, 400, 300, 200, or 100 cells (or any derivable range therein). In some embodiments, the composition comprises less than 1 µg of total protein. In some embodiments, the composition comprises less than 5, 4.5, 4, 3.5, 3, 2.5, 2, 1.5, 1, 0.5, 0.4, 0.3, 0.2, 0.1, or 0.01 µg (or any derivable range therein) of total protein.

In some embodiments, the method further comprises the detection of a cellular marker. Such methods may include one or more of the following steps: addition of a marker-specific antibody, detection of binding of the marker-specific antibody, detection of the binding of the marker-specific antibody by immunofluorescence, isolating cells comprising the detected binding by cell sorting (e.g., fluorescence activated cell sorting, FACS), flow cytometry of the cells, and/or culturing of the isolated cells.

In some embodiments, the method further comprises determining the total amount of target protein of interest. In some embodiments, determining the total amount of target protein of interest comprises directly or indirectly detecting the mRNA transcript of the target protein of interest. In some embodiments, determining the total amount of target protein of interest comprises directly or indirectly detecting the specified functional and non-specified functional forms of the protein.

In some embodiments, the method further comprises adding a suspected target protein modifier. In some embodiments, the target protein modifier comprises a small molecule, a polypeptide, or an antibody. "Small molecule" compounds are typically organic, non-peptide molecules, having a molecular weight less than 10,000 Da. In some embodiments, they are less than 5,000 Da, less than 1,000 Da, or less than 500 Da (and any range derivable therein). This class of modifiers includes chemically synthesized molecules, for example, compounds from combinatorial chemical libraries. Synthetic compounds may be rationally designed or identified from screening methods described herein. Methods for generating and obtaining small molecules are well known in the art (Schreiber, Science 2000; 151:1964-1969; Radmann et al., Science 2000; 151:1947-1948, which are hereby incorporated by reference).

In some embodiments, the method further comprises one or more of liquid chromatography-mass spectrometry, mass cytometry, imaging mass spectrometry, and mass spectrometry. In some embodiments, the method specifically excludes one or more of liquid chromatography-mass spectrometry, mass cytometry, imaging mass spectrometry, and mass spectrometry. In some embodiments, the composition of (i) is heterogenous. In some embodiments, the two or more target enzymes of interest comprise serine hydrolases, cysteine proteases, kinases, metalloproteases, β-retaining glycosidases, tyrosine phosphatases, or chtochrome P450s. In some embodiments, the retrieval tag and/or retrieval tag binder are selected from one or more of the following retrieval tag and retrieval tag binder pairs: biotin and streptavidin, biotin and avidin, biotin and anti-biotin, desthiobiotin and streptavidin, desthiobiotin and avidin, desthiobiotin and anti-biotin, $O^6$-benzylguanine and SNAP protein, an alkyne and an azide, an azide and a cyclooctyne such as

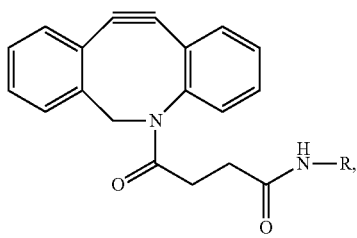

a tetrazine and a trans-cyclooctene such as

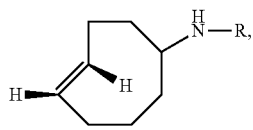

other "click chemistry" pairs, and an epitope and epitope-specific antibody.

In some embodiments, the targeting group comprises targeting group comprises a flourophosphonate, diphenylphosphonate, sulfonyl fluoride, acyloxymethyl ketone, phenoxymethylketone, vinyl sulfone, epoxide, halomethylketone, alpha-haloester, alpha-haloamide, α, β-unsaturated ester, α, β-unsaturated ketone, diazomethylketone, acyl phosphate, acylphosphonate, hydroxamate, carbamate, ester, thioester, 2-deoxy-2-fluoro glycoside, α-bromobenzylphosphonate, or 2-ethynylnaphthalene.

In some embodiments, the method further comprises obtaining a biological sample from a patient. In some embodiments, the biological sample comprises blood, serum, or tissue. In some embodiments, the biological sample comprises cancerous cells. In some embodiments, the cancerous cells comprise ovarian or prostate cancerous cells. In some embodiments, the cancerous cells are from a cancer described herein. In some embodiments, the method further comprises determining the level or abundance of the protein of interest in the specified functional form in the biological sample.

In some embodiments, the method further comprises comparing the level or abundance of a protein of interest in the specified functional form in the biological sample compared to a control. In some embodiments, the control comprises the level of the protein of interest in a specified functional form in a biological sample from a patient having non-aggressive cancer or a non-cancerous sample. In some embodiments, the control comprises the level of the protein of interest in the specified functional form in a biological sample from a patient having non-aggressive ovarian or prostate cancer or a non-cancerous sample. In some embodiments, the non-aggressive cancer comprises stage I or stage II cancer. In some embodiments, the non-aggressive ovarian or prostate cancer comprises stage I or stage II ovarian or prostate cancer. In some embodiments, diagnosing the patient based on the determined level of protein of interest in the specified functional form. In some embodiments, the method further includes diagnosing the patient with aggressive or non-aggressive cancer based on the level or abundance of the protein of interest in the specified functional form in the biological sample from the patient. In some embodiments, the method further includes diagnosing the patient with aggressive or non-aggressive prostate or ovarian cancer based on the level or abundance of the protein of interest in the specified functional form in the biological sample from the patient. In some embodiments, the method further comprises treating the patient diagnosed with aggressive cancer with a stage 3 or 4 cancer therapeutic treatment regimen or treating the patient diagnosed with non-aggressive cancer with a stage 1 or 2 cancer therapeutic treatment regimen. In some embodiments, the method further comprises treating the patient diagnosed with aggressive ovarian or prostate cancer with a stage 3 or 4 ovarian or prostate cancer therapeutic treatment regimen or treating the patient diagnosed with non-aggressive ovarian or prostate cancer with a stage 1 or 2 ovarian or prostate cancer therapeutic treatment regimen.

In some embodiments, the retrieval tag comprises biotin, streptavidin, avidin, anti-biotin, desthiobiotin, $O^6$-benzylguanine, SNAP protein, alkyne, azide,

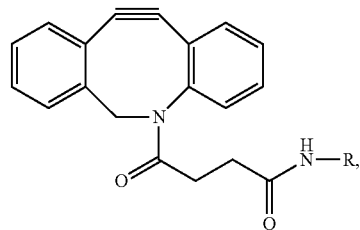

tetrazine,

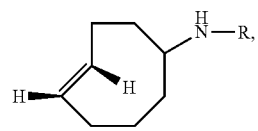

a peptide epitope or a peptide epitope-specific antibody. In some embodiments, the retrieval tag binder comprises biotin, streptavidin, avidin, anti-biotin, desthiobiotin, $O^6$-benzylguanine, SNAP protein, alkyne, azide,

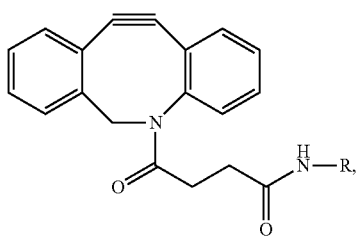

tetrazine,

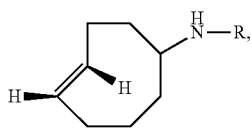

a peptide epitope or a peptide epitope-specific antibody.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that a numerical value discussed herein may be used with the term "about" or "approximately."

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The terms "protein", "polypeptide" and "peptide" are used interchangeably herein when referring to a gene product or functional protein.

The terms "contacted" and "exposed," when applied to a cell or composition, are used herein to describe the process by which an agent is delivered to a target cell or are placed in direct juxtaposition with the target cell, composition, or target molecule.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives as well as "and/or." As used herein "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment set forth with the term "comprising" may also be substituted with the word "consisting of" for "comprising."

It is contemplated that any method or composition described herein can be implemented with respect to any other method or composition described herein and that different embodiments may be combined.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13A-B exemplifies family-wide targeting groups (warhead groups) that can be used in the methods of the disclosure.

FIG. 14 shows exemplary retrieval tags and retrieval tag binder (partner) pairs.

FIG. 16A-C. (A) HPLC chromatograms of precursor amine-modified ssDNA (left) and crude succinimidyl-ssDNA (right) after reaction with DSS. (B) Reducing SDS-PAGE gel analysis of three commercial antibodies before and after reaction with succinimidyl-ssDNA. Protein bands were visualized by Sybr-gold staining, revealing ssDNA-modification predominantly on heavy chains. (C) Native PAGE gel analysis of commercial antibodies before and after reaction with succinimidyl-ssDNA reveals high labeling efficiency to mono-, di, and tri-oligonucleotide conjugates for all three antibodies.

FIG. 17A-F. (A) Schematic depiction of the secondary-linked, "sandwich-like" activity dependent proximity ligation arrangement. (B-C) ADPL imaging (B) and quantification (C) of NCEH1 activity in SKOV3 ovarian cancer cells with or without fluorophosphonate-biotin (FP-Bio) probe treatment using secondary-linked conjugates. (D) Schematic depiction of direct ADPL detection of NCEH1 activity using antibody- and streptavidin-oligonucleotide conjugates synthesized by DSS chemistry. (E-F) ADPL imaging (E) and quantification (F) of NCEH1 activity in SKOV3 ovarian cancer cells with or without fluorophosphonate-biotin (FP-Bio) probe treatment using the direct oligonucleotide conjugates. Scale bar: 10 μm.

FIG. 18A-D. (A) Schematic depiction of dual-antibody detection of a model protein, GAPDH, for PLA-qPCR quantification. (B) PLA-qPCR detection of GAPDH protein in whole cell lysate from PC3 cells (60 ng of sample input) is completely dependent proximity ligation components. (C) PLA-qPCR detection of GAPDH across a high dynamic range below pg levels of whole proteome using both polyclonal and monoclonal oligonucleotide-antibody conjugates synthesized by DSS chemistry. The X-axis displays the concentration of the cell lysate, while the Y-axis is the delta Ct value normalized by 'PBS' blank control. (D) Limit of detection values of whole proteome amount for GAPDH detection by PLA-qPCR. Sample LOD denotes the LOD of original sample input amount, whereas the assay LOD accounts for the 680-fold dilution introduced during the PLA workflow.

FIG. 19A-D. Solution-phase Activity-dependent Proximity Ligation.

FIG. 20. Overall Structure in sADPL Design. Two amine modified oligos were conjugated to antibody and streptavidin, respectively. Forward primer (FP) and reverse primer (RP) were utilized in real time PCR step. The splint were complementary to the two probes to facilitate the ligation of the hydroxyl group and phosphate group at the two termini. The 3-base overhand at two ends were designed to prevent the connector oligonucleotide from giving rise to ligation independent products by acting as a primer and/or template for amplification. A Taqman probe was designed for real time PCR quantification. A standard curve for Taqman probe qPCR were generated with a series dilution of the ligation product. The amplification factor and PCR efficiency were obtained from the curve so that one could transform the CT difference into activity fold change.

FIG. 22. sADPL Reproducibility and Sensitivity. The reproducibility of sADPL is tested by the raw Ct values in biological replicates performed at different days. The dot represents the Ct value for different dilution fold (previous 3-fold dilution series). The sensitivity and dynamic range were compared with western blot (WB). sADPL requires ~10^6 fold less proteome than WB with broader dynamic range. The LODs for 6 biomarkers were determined including the sample LOD and assay LOD. Sample LOD is the amount of the proteome required to generate the signal which is 3-fold of standard deviation above background. As 680-fold dilution were performed in the workflow, the sample LOD divided by the dilution fold is the assay LOD.

FIG. 23. In situ Target Engagement. Cancer cells were treated with DMSO as the control, with inhibitor prior to family wide probe to pre-block the active site, or with family-wide probe directly. Then sADPL workflow was applied to read out the CT difference. Serine hydrolase NCEH1 and its specific inhibitor JW480, or FAAH and inhibitor PF3845 were applied. The activity fold change was transformed from CT value with PCR amplification factor 1.91 determined by a standard qPCR curve and the activities were normalized to DMSO control at different cell lysate concentrations. It was found that the activities in inhibitor competition groups will bring the activities down to the levels of DMSO controls to indicate the target engagements at both cases. To quantitatively measure the target engagement, different dose of JW480 was applied to either its target NCEH1, or off-target MGLL. Dose-dependent inhibition of NCEH1, with apparent IC50=17.8 nM, similar to those previously reported by gel-based profiling (12 nM).

FIG. 35. A. Nucleotide analogues bind to the active sites of ATPases and the biotin affinity tag is irreversibly transferred to highly conserved lysine residues in the active site. B. Structures of desthiobiotin nucleotide analogues. Desthiobiotin binding to streptavidin is easily reversible under acidic elution conditions, allowing high recovery of labeled proteins and peptides. Desthiobiotin is attached to the nucleotide through a labile acyl phosphate linkage, allowing efficient desthiobiotin label transfer to amines near the active site. ATP and ADP nucleotide analogues label a complementary set of ATPases, which is likely due to differences in the proximity of the acyl phosphate linkage to conserved lysines near the active site.

Description of Illustrative Embodiments

Figure 1:
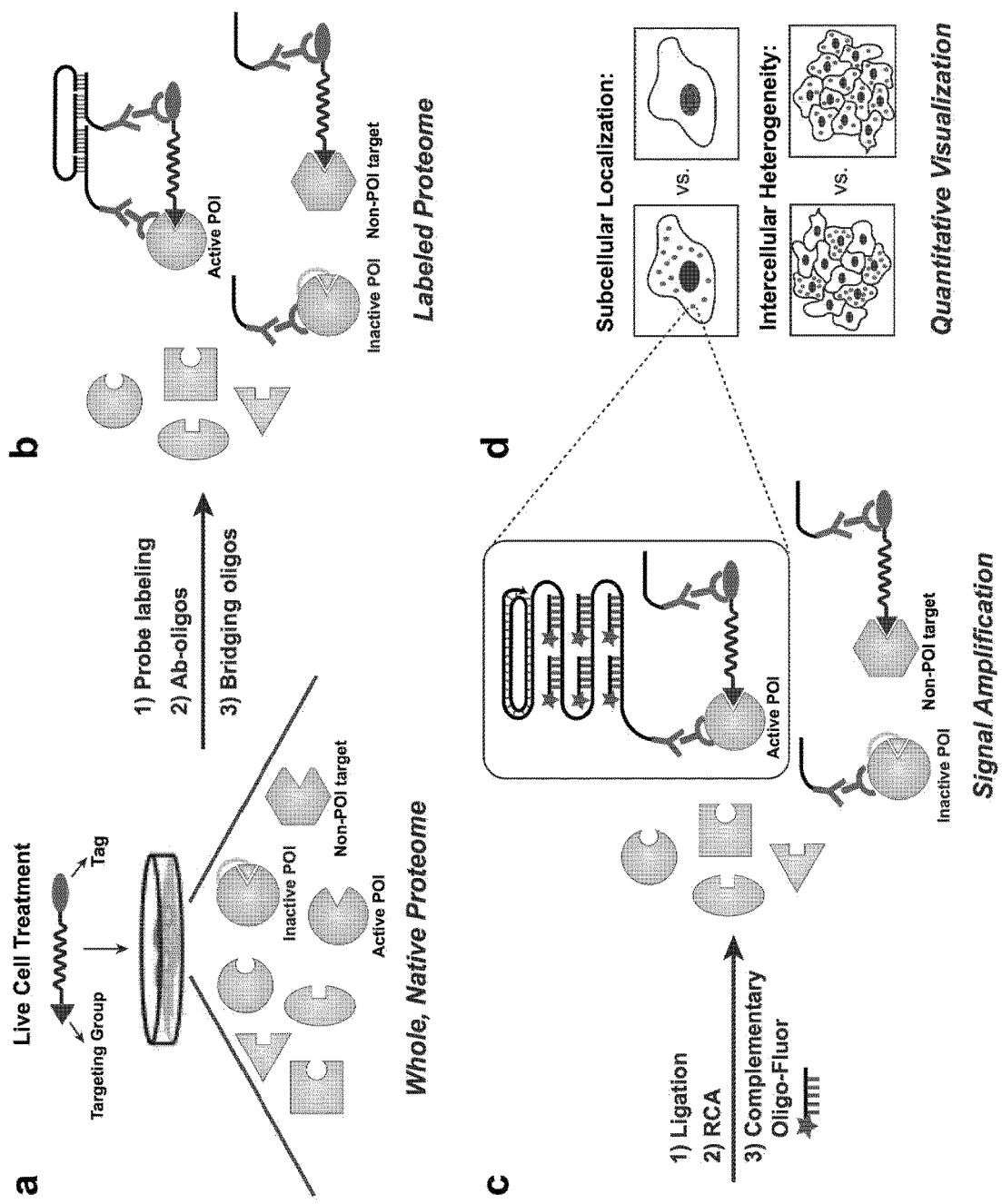
FIG. 1A-D. Schematic depicting the activity-dependent proximity ligation (ADPL) workflow. (a) Live-cells pulsed with a family-wide chemical probe (an example of a molecular construct comprising: a targeting group operatively linked to a retrieval tag) labels active proteins within their native environment. (b) Detection of probe-labeled protein-of-interest (POI) is accomplished by incubation of fixed cells with primary antibodies directed to the POI, and probe detection handle (biotin). Subsequent incubation with secondary antibody-oligonucleotide conjugates directed against each primary antibody (e.g., to form an antibody-oligo construct) enables hybridization and ligation of two bridging complementary oligonucleotides only when the probe and POI are in high proximity (i.e., on the same protein). (c) Signal amplification and detection is achieved through ligation, rolling circle amplification and subsequent hybridization of fluorophore conjugated complementary oligonucleotides. (d) Visualization and quantification of subcellular and intercellular enzyme activity is afforded by fluorescence microscopy.

The methods of the disclosure provide for a chemical proteomic platform to address several shortcomings that plague current proteomic profiling approaches. Chief among these were the inability to probe a wide dynamic range of sample abundance, provide information on the functional state of proteins, and the capacity to quantify this information with spatial resolution at the inter- and intracellular scale. Compared to existing activity-based proteomic approaches with gel- or LC-MS/MS as a readout, the incorporation of a specific and robust amplification scheme applied in native cell environments allows for significant expansion of the questions that can be addressed in biological, diagnostic, and therapeutic systems. First, the disclosed methods permit quantification of enzyme activity across a high dynamic range with respect to sample input as well as relative abundance within the proteome of a given cell. The examples of the disclosure demonstrate that the disclosed methods allow for single-cell resolution, as well as interrogation of low abundance or low activity protein targets, both of which represent important contexts in biology. Single-cell resolution and low sample requirements enable the detection and quantification of enzyme activity in heterogeneous cellular populations, including cellular co-culture and primary ovarian cancer spheroids. The fact that the methods of the disclosure do not require any genetic manipulation is also important to allow for direct compatibility with other types of primary tissues and fluids. Furthermore, readouts such as fluorescence imaging, qPCR, and sequencing can all be combined with the methods of the disclosure. Additionally, implementation of barcoded oligo-fluorophores or primers enable multiplexed readout of active enzymes within and between families, as well as integration with methods to simultaneously capture information on transcript and protein abundance. The use of cell permeable family-wide chemical probes permits tagging of active proteins in their native cellular context, which provides a better representation of their functional properties. The Examples of the application demonstrate the applicability of the disclosed methods to serine hydrolase enzymes under external (ESD and PAFAH2) or endogenous regulation (NCEH1 and fatty acid amide hydrolase, FAAH, FIG. 9B). Additionally, the examples also show that ADPL can be extended to other classes of chemical probes and corresponding enzyme families, such as the cysteine protease CTPB. Since this technique does not require sample homogenization it allows for retention of quantitative, activity-dependent information at the inter- and intracellular scale. These aspects of the disclosed methods are useful for the study of the relationship between protein abundance, localization and activity in a variety of biological contexts (e.g., cancer, inflammation, immune function, development).

Another powerful aspect of this platform is its ability to directly probe enzyme activity in living cells, obviating the need to develop specific activity assays and the process of overexpression and purification for a target protein of interest. Indeed, for many proteins, such as the glycosylated, integral membrane hydrolase NCEH1 studied here, this workflow may not be possible at all. The disclosed methods can be used to detect endogenous differences in enzyme activity among distinct cellular phenotypes, as well as to interrogate the action of small molecule inhibitors on enzyme function directly in live cells. This process only requires the knowledge that the enzyme is targeted by the family-wide probe, and the availability of a single antibody for the protein of interest. In the case of PAFAH2, genetic incorporation of a modular affinity tag allows for activity measurements in live cells, indicating that this approach is useful for the development of targeted assays for enzymes that are known to belong to a specific enzyme family, but do not have known endogenous substrates or are problematic for in vitro biochemistry. Additionally, this approach can be used to verify target engagement in cells without relying on downstream peripheral biomarkers, an important capability in both basic and translational research. In conclusion, the examples demonstrate the utilization of a single, family-wide probe to provide spatially resolved, target-specific information for several diverse serine hydrolases without any optimization. This modularity may be extended to other mechanism-driven or affinity-based probes, greatly expanding the information that can be captured on these proteins with spatial resolution, high dynamic range, and in native environments. This approach enables the interrogation of important basic and translational questions in biology and medicine and provides novel therapeutic and diagnostic approaches to treat and detect disease.

I. Assay Components

A. Molecular Construct

Embodiments of the disclosure relate to methods and compositions comprising a molecular construct comprising: a targeting group operatively linked to a retrieval tag; wherein the targeting group specifically binds to the specified functional form of the two or more target proteins of interest. Exemplary embodiments of the molecular construct and fragments thereof are described throughout the application.

The concentration of the molecular construct in the compositions and methods of the disclosure may be at least, at most, or exactly $1 \times 10^{-10}$, $1 \times 10^{-9}$, $1 \times 10^{-8}$, $1 \times 10^{-7}$, $1 \times 10^{-6}$, $1 \times 10^{-5}$, $1 \times 10^{-4}$, $1 \times 10^{-3}$, $1 \times 10^{-2}$, $1 \times 10^{1}$, 1, $1 \times 10^{2}$, $1 \times 10^{3}$, $1 \times 10^{4}$, $1 \times 10^{5}$, $1 \times 10^{6}$, $1 \times 10^{7}$, $1 \times 10^{8}$, $1 \times 10^{9}$, $1 \times 10^{10}$, $1 \times 10^{-2}$, $1 \times 10^{1}$, or 1, $1 \times 10^{10}$ (or any derivable range therein) pM, nM, μM, mM, M, cM, or dM.

In some embodiments, the molecular construct is cell permeable.

B. Targeting Groups

The targeting group is a moiety that specifically binds to a specified functional form of a protein of interest, or family of proteins, or group of enzymes having a similar or the same enzymatic activity and/or active site structure. The term "specifically binds to active specified functional form of a protein" refers to a binding that includes the specified functional form and excludes the non-specified functional form or wherein the targeting group binds to less than 30, 25, 20, 15, 10, 9, 8, 7, 6, 5, 4, 3, 2, 1, 0.5, or 0.1% (or any derivable range thereof) of the total non-specified functional form of the protein. In some embodiments, the interaction of the target protein with the specified or non-specified functional form of the protein of interest may be defined as being a $K_d$ or $K_m$ of at least, at most, or exactly $1 \times 10^{-10}$, $1 \times 10^{-9}$, $1 \times 10^{-8}$, $1 \times 10^{-7}$, $1 \times 10^{-6}$, $1 \times 10^{-5}$, $1 \times 10^{-4}$, $1 \times 10^{-3}$, $1 \times 10^{-2}$, $1 \times 10^{-1}$, 1, $1 \times 10^{2}$, $1 \times 10^{3}$, $1 \times 10^{4}$, $1 \times 10^{5}$, $1 \times 10^{6}$, $1 \times 10^{7}$, $1 \times 10^{8}$, $1 \times 10^{9}$, $1 \times 10^{10}$, $1 \times 10^{-2}$, $1 \times 10^{-1}$, or 1, $1 \times 10^{10}$ (or any derivable range therein) pM, nM, μM, mM, M, cM, or dM.

Figure 13A:

FIG. 13 exemplifies family-wide targeting groups (warhead groups) that can be used in the methods of the disclosure. FIG. 13 further exemplifies which probes are useful for certain enzyme families. For example, fluorophosphonate, diphenylphosphonate, and sulfonyl fluoride are useful in methods wherein the protein of interest is a serine hydrolase/serine protease. Sulfonyl fluoride is also useful in methods wherein the protein of interest is a kinase. Acyloxymethyl ketone, phenoxymethylketone, vinyl sulfone, epoxide, halomethylketone, α, β-unsaturated ester, α, β-unsaturated ketone, and diazomethylketone are useful when the protein of interest is a cysteine protease. Nucleotide acyl phosphate is useful when the protein of interest is a kinase. Hydroxamate is useful when the protein of interest is a metalloprotease. 2-deoxy-2-fluoro glycoside is useful when the protein of interest is a β-retaining glycosidase. α-bromobenzylphosphonate is useful when the protein of interest is a tyrosine phosphatase, and 2-ethynylnaphthalene is useful when the protein of interest is a cytochrome P450.

| Targeting Group/Warhead | Target Proteins |
| --- | --- |
| fluorophosphonate, diphenylphosphonate, and sulfonyl fluoride | serine hydrolase/serine protease |
| Sulfonyl fluoride | kinase |
| Acyloxymethyl ketone, phenoxymethylketone, vinyl sulfone, epoxide, halomethylketone, α, β-unsaturated ester, α, β-unsaturated ketone, and diazomethylketone | cysteine protease |
| Nucleotide acyl phosphate | kinase |
| Hydroxamate | metalloprotease |
| 2-deoxy-2-fluoro glycoside | tyrosine phosphatase |
| 2-ethynylnaphthalene | cytochrome P450 |
| Acyloxymethylketone (AOMK) | Cathepsin family of cysteine proteases |
| Epoxyketone | Cathepsin family of cysteine proteases |
| Fluoromethylketone (FMK) | Caspase family of cysteine proteases |
| Phosphonate | Serine hydrolases |
| Acylphosphate | Kinases |

In some embodiments, the targeting group and retrieval tag comprises desthiobiotin-ADP or desthiobiotin-ADP, as shown in FIG. 35. As shown in FIG. 35, binding to active kinase results in acylation of conserved, proximal lysine epsilon-amine(s), tagging the protein with a biotin or desthiobiotin. All kinases have active site proximal lysines, and therefore all kinases and ATP-binding proteins can be profiled using this and similar probes. The treated cellular sample can be processed for ADPL as with other probe classes for in situ cellular imaging, or in lysate and homogenized digital quantitation by qPCR, digital PCR or next-generation sequencing readout. Other kinase probes with diverse electrophilic warheads including sulfonylfluoride-containing, acylphosphate, acylphosphonate, N-hydroxysuccinimide, ester and others can be appended onto kinase-binding small molecule scaffolds and used for ADPL kinase profiling as well.

Further examples of family-wide probes useful in the methods and compositions of the disclosure include:

Cell permeable kinases probe (further described in J. Am. Chem. Soc. 2017, 139, 680, which is incorporated by reference).

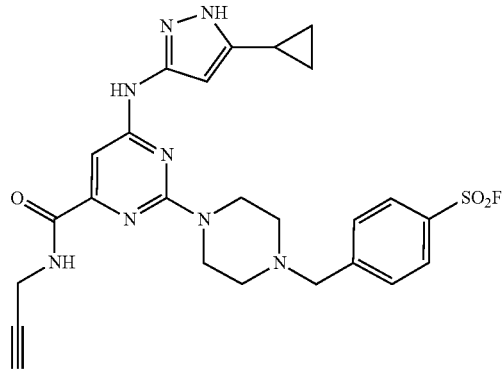 [SMILES: C#CCNC(=O)c1cc(Nc2cc(C3CC3)[nH]n2)nc(N2CCN(Cc3ccc(S(=O)(=O)F)cc3)CC2)n1]

wherein the SO$_2$F comprises the targeting group and the alkyne comprises the retrieval tag moiety or a functional group on which a retrieval tag can be attached.

Methyltransferases probe (further described in, J. Am. Chem. Soc. 2016, 138, 13335, which is incorporated by reference).

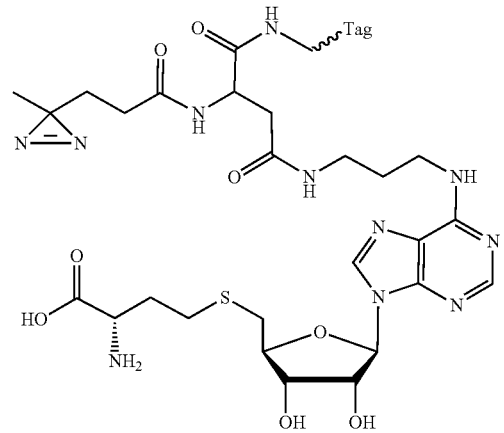

wherein

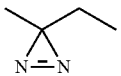

comprises the targeting group.

Phosphoaspartate modification probe (further described in, Angew. Chem. Int. Ed. 2018, 57, 15712, which is incorporated by reference).

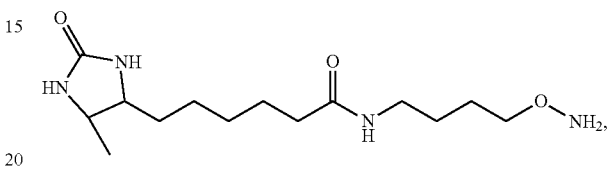

wherein

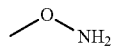

comprises the targeting group and

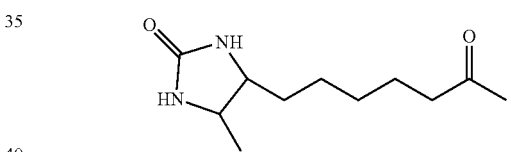

comprises the retrieval tag moiety.

Methyl transferases probe (further described in, J. Am. Chem. Soc. 2014, 136, 8669, which is incorporated by reference).

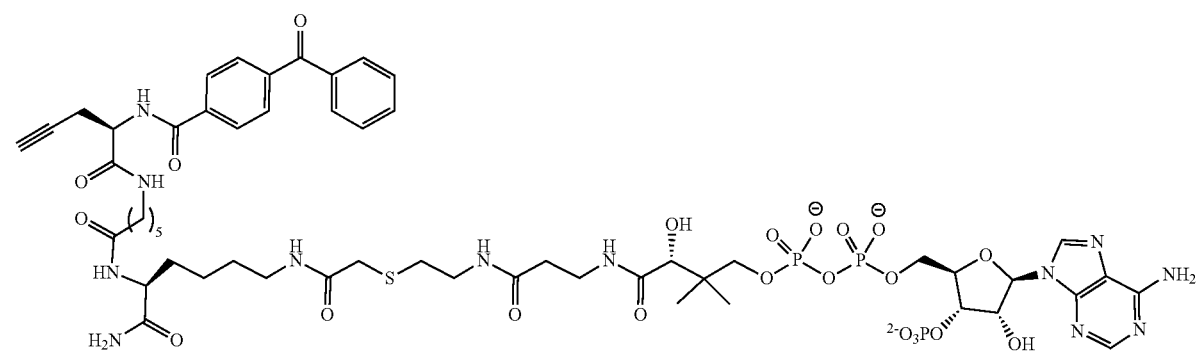

wherein

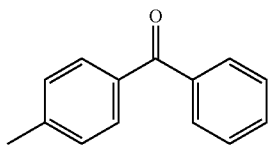

comprises the targeting group and

comprises the retrieval tag moiety.

Caspases probe (further described in, Nature Med. 2009, 15, 967, which is incorporated by reference).

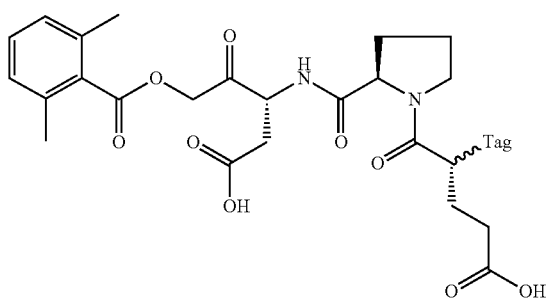

wherein

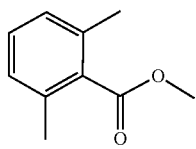

comprises the targeting group.

Metalloproteases probe (further described in, Proc. Natl. Acad. Sci. 2004, 101, 10000, which is incorporated by reference).

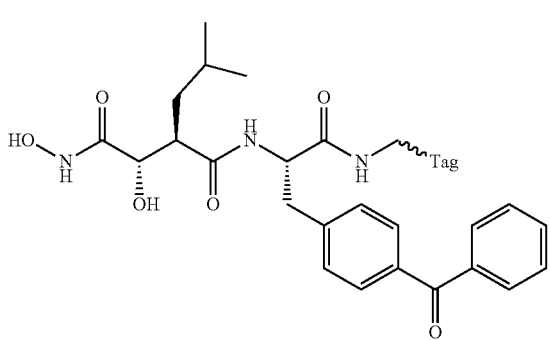

wherein

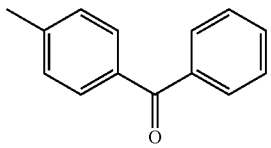

comprises the targeting group.

Cathepsins probe (further described in. Cancer Cell 2004, 5, 443, which is incorporated by reference).

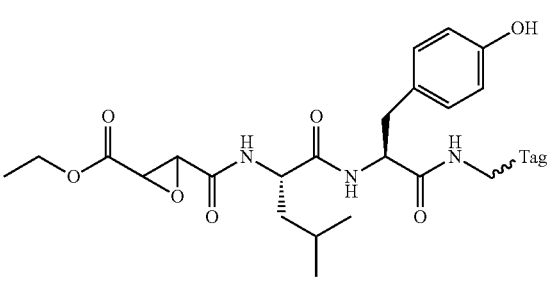

wherein

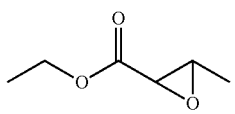

comprises the targeting group.

Deubiquitylases probe (further described in, Mol. Carcinog. 2006, 45, 260, which is incorporated by reference).

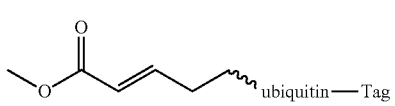

wherein

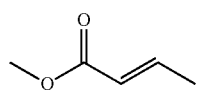

comprises the targeting group.

Cytochrome P450s probe (further described in. J. Am Chem Soc. 2009, 131, 10692, which is incorporated by reference).
group.

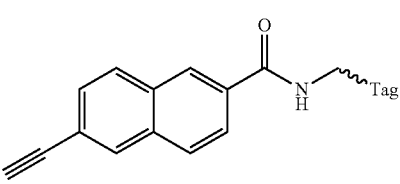

wherein

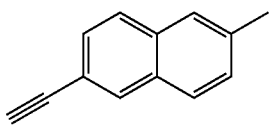

comprises the targeting group.

Tyrosine phosphatases probe (further described in, J. Am. Chem. Soc. 2009, 131, 10692, which is incorporated by reference).

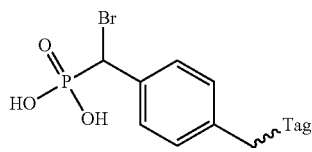

wherein

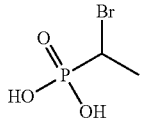

comprises the targeting group

Non-cell permeable kinases probe (further described in. Biochemistry, 2007, 46, 350, which is incorporated by reference).

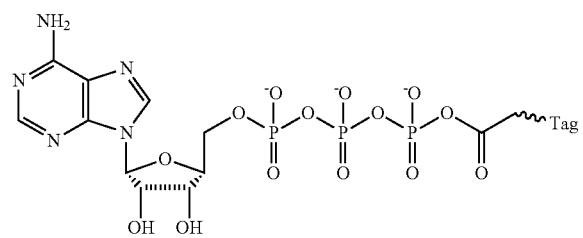

wherein

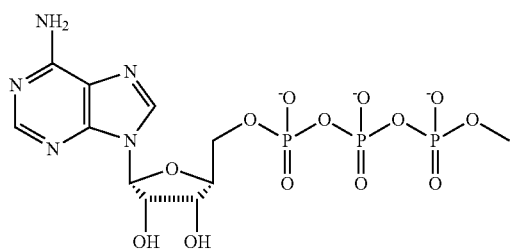

comprises the targeting group.

Proteasome probe (further described in, Nat. Methods, 2005, 2, 357, which is incorporated by reference).

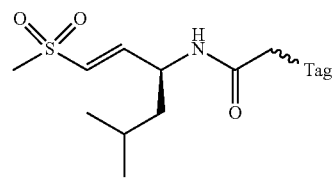

wherein

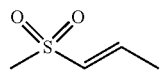

comprises the targeting group

Glycosidase probe (further described in, Angew. Chem. Int. Ed. 2004, 43, 5338, which is incorporated by reference)

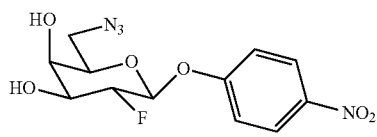 [SMILES: [N-]=[N+]=NCC1OC(Oc2ccc([N+](=O)[O-])cc2)C(F)C(O)C1O]

wherein

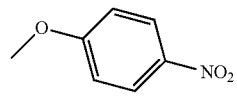

comprises the targeting group and $N_3$ comprises the retrieval tag or functional group to which a retrieval tag can be attached.

Serine hydrolase probe (further described in, Biochemistry, 2001, 40, 4005, which is incorporated by reference)

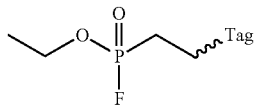

wherein F comprises the targeting group.

2. Retrieval Tags and Retrieval Tag Binder Pairs

Exemplary retrieval tags and retrieval tag binder (partner) pairs are shown in FIG. 14.

It is contemplated that the retrieval tag and retrieval tag binder/partner may be interchangeable. For example, a compound identified herein as a retrieval tag may be used as a retrieval tag binder/partner, and the compound described as the retrieval tag binder/partner may be used as a retrieval tag.

Further exemplary retrieval tag and retrieval tag binder pairs include:

| Retrieval Tag | Retrieval Tag Binder |
|---|---|
| E-tag (GAPVPYPDPLEPR) | Anti-E antibody |
| Flag-tag (DYKDDDDK) | Anti-FLAG antibody |
| HA-tag (YPYDVPDYA) | anti-HA antibody |
| myc-tag (EQKLISEEDL) | anti-myc antibody |
| NE-tag (TKENPRSNQEESYDDNES) | monoclonal IgG1 antibody |
| SBP-tag (MDEKTTGWRGGHVVEGLAGELE QLRARLEHHPQGQREP) | streptavidin |
| TC tag, a tetracysteine tag (CCPGCC) | FlAsH and ReAsH biarsenical compounds |
| V5 tag (GKPIPNPLLGLDST) | Anti-V5 antibody |
| VSV-tag (YTDIEMNRLGK) | Anti-VSV antibody |
| SpyTag (AHIVMVDAYKPTK) | SpyCatcher protein |
| SnoopTag (KLGDIEFIKVNK) | SnoopCatcher protein |

In some embodiments, the retrieval tag and/or retrieval tag binder has an atomic mass of at least, at most, or exactly 200, 175, 150, 125, 100, 75, 50, 40, 30, 20, 10, 5, 1, 0.5, 0.1, 0.05, or 0.01 kDa (or any range derivable therein). In some embodiments, the retrieval tag and/or retrieval tag binder has a molar mass of at least, at most, or exactly 10000, 9000, 8000, 7000, 6000, 5000, 4000, 3000, 2000, 1000, 900, 800, 700, 600, 500, 400, 300, 250, 225, 200, 175, 150, 125, 100, 75, 50, or 25 g/mol (or any derivable range therein).

3. Linker

In order to conjugate two molecules, such as a retrieval tag to a targeting group or an oligo to an antibody or to a retrieval tag binder, the following exemplary techniques and linking reagents can be applied.

Functional groups and reactive groups may be used to link two molecules together. The term "functional groups" as used herein is not restricted to reactive chemical groups forming covalent bonds, but also includes chemical groups leading to an ionic interaction or hydrogen bonds with one or more components of the assay.

The functional groups or the linking molecules bearing them may be selected from amino groups, carbonic acid groups, thiols, thioethers, disulfides, guanidino, hydroxyl groups, amine groups, vicinal dioles, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or nanosphere. Nucleic acids can provide a link to affinity molecules containing themselves nucleic acid molecules, though with a complementary sequence with respect to the linking molecule.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

The molecule can be chemically modified, for instance by the binding of a phosphonic acid derivative having a functional reactive group. One example of these phosphonic acid or phosphonic acid ester derivates is imino-bis(methylenphosphono) carbonic acid which can be synthesized according to the "Mannich-Moedritzer" reaction. The phosphonic acid (ester) derivative, or linking molecules bound thereto, may display the same functional groups as given above.

For non-covalent linking techniques, chain-type molecules having a polarity or charge opposite to that of the substrate or nanosphere surface are particularly suitable. Examples for linking molecules which can be non-covalently linked to core/shell nanospheres involve anionic, cationic or zwitter-ionic surfactants, acid or basic proteins, polyamines, polyamides, polysulfone or polycarboxylic acid. The hydrophobic interaction between a molecule and amphiphilic reagent having a functional reactive group can generate the necessary link. In particular, chain-type molecules with amphiphilic character, such as phospholipids or derivatised polysaccharides, which can be crosslinked with each other, are useful.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or nanosphere or thereafter. Further, it is possible, by means of incubation, to effect a direct binding of molecules to correspondingly pre-treated substrate or nanospheres (for instance by trimethylsilyl bromide), which display a modified surface due to this pre-treatment (for instance a higher charge or polar surface).

C. Oligos

1. Nucleic Acids

The current disclosure includes embodiments of nucleic acids comprising one or more of a heterologous receptor gene and an inducible reporter. The terms "oligonucleotide," "polynucleotide," and "nucleic acid are used interchangeable and include linear oligomers of natural or modified monomers or linkages, including deoxyribonucleosides, ribonucleosides, α-anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 3-4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when oligonucleotides having natural or non-natural nucleotides may be employed, e.g., where processing by enzymes is called for, usually oligonucleotides consisting of natural nucleotides are required.

The nucleic acid may be an "unmodified oligonucleotide" or "unmodified nucleic acid," which refers generally to an oligomer or polymer of ribonucleic acid (RNA) or deoxyribonucleic acid (DNA). In some embodiments a nucleic acid molecule is an unmodified oligonucleotide. This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases. The term "oligonucleotide" can be used to refer to unmodified oligonucleotides or oligonucleotide analogs.

Specific examples of nucleic acid molecules include nucleic acid molecules containing modified, i.e., non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases. In a specific embodiment, the modification comprises a methyl group.

Nucleic acid molecules can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Modifications to nucleic acid molecules can include modifications wherein one or both terminal nucleotides is modified.

One suitable phosphorus-containing modified internucleoside linkage is the phosphorothioate internucleoside linkage. A number of other modified oligonucleotide backbones (internucleoside linkages) are known in the art and may be useful in the context of this embodiment.

Representative U.S. patents that teach the preparation of phosphorus-containing internucleoside linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 5,625,050, 5,489,677, and 5,602,240 each of which is herein incorporated by reference.

Modified oligonucleoside backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having amide backbones; and others, including those having mixed N, O, S and CH2 component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Nucleic acid molecules can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds.

Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this embodiment. Examples of sugar modifications useful in this embodiment include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted C1 to C10 alkyl or C2 to C10 alkenyl and alkynyl. Particularly suitable are: 2-methoxyethoxy (also known as 2'-O-methoxyethyl, 2'-MOE, or 2'-OCH2CH2OCH3), 2'-O-methyl (2'-O—CH3), 2'-fluoro (2'-F), or bicyclic sugar modified nucleosides having a bridging group connecting the 4' carbon atom to the 2' carbon atom wherein example bridge groups include —CH2-O—, —(CH2)2-O— or —CH2-N(R3)-O wherein R3 is H or C1-C12 alkyl.

One modification that imparts increased nuclease resistance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265;

5,658,873; 5,670,633; 5,792,747; and 5,700,920, each of which is herein incorporated by reference in its entirety.

Nucleic acid molecules can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Additional modifications to nucleic acid molecules are disclosed in U.S. Patent Publication 2009/0221685, which is hereby incorporated by reference. Also disclosed herein are additional suitable conjugates to the nucleic acid molecules.

2. Barcodes

In some embodiments, the oligos used in the methods described herein (either first, second, third, fourth, etc . . . , retrieval, or further) may comprise a barcode. The barcode region can be specific to a particular protein or to a particular family member of a family of proteins/enzymes.

The barcoded region may be used to specifically identify one protein of interest. The barcode region can be a polynucleotide of at least, at most, or exactly 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200 or more (or any range derivable therein) nucleotides in length. The barcode may comprise or further comprise one or more universal PCR regions, adaptors, linkers, or a combination thereof.

The barcode region or at least a portion thereof is a polynucleotide sequence that can be used to identify the specific activated protein of interest. In embodiments relating to a population of cells, determining the identity of the barcode is done by determining the nucleotide sequence of the barcode. As discussed herein, methods may involve sequencing one or more barcode regions or nucleic acid regions or having such regions sequenced.

The unique portions of the barcodes may be continuous along the length of the barcode sequence or the barcode may include stretches of nucleic acid sequence that are not unique to any one barcode. The barcodes and/or index regions are quantified or determined by methods known in the art, including quantitative sequencing (e.g., using an Illumina® sequencer) or quantitative hybridization techniques (e.g., microarray hybridization technology or using a Luminex® bead system). Sequencing methods are further described herein.

D. Molecular Labels

The oligonucleotides, nucleic acid molecules, primers, probes, antibodies, and retrieval tag/binder molecules in the compositions and methods described herein may include one or more labels. Nucleic acid molecules can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labels" are chemical or biochemical moieties useful for labeling a nucleic acid. "Labels" include, for example, fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In some embodiments, the molecules may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH);

DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The nucleic acid molecules of the disclosed compositions and methods may be labeled with a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

The labels can be conjugated to molecules directly or indirectly by a variety of techniques. Depending upon the precise type of label used, the label can be located at the 5' or 3' end of the oligonucleotide or N or C-terminus of a peptide/polypeptide or located internally in the oligonucleotide's nucleotide sequence. Using commercially available phosphoramidite reagents, one can produce nucleic acid molecules containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Molecules may also incorporate functionalizing reagents having one or more sulfhydryl, amino or hydroxyl moieties into the nucleic acid sequence. For example, a 5' phosphate group can be incorporated as a radioisotope by using polynucleotide kinase and [γ32P]ATP to provide a reporter group. Biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, 35S-dATP, and biotinylated dUTP.

Oligonucleotide derivatives are also available as labels. For example, etheno-dA and etheno-A are known fluorescent adenine nucleotides which can be incorporated into a reporter. Similarly, etheno-dC is another analog that can be used in reporter synthesis. The reporters containing such nucleotide derivatives can be hydrolyzed to release much more strongly fluorescent mononucleotides by the polymerase's 5' to 3' nuclease activity as nucleic acid polymerase extends a primer during PCR.

II. Assay Methods

A. Ligation Methods

Aspects of the disclosure include the ligation of nucleic acids. In some embodiments, the methods include ligating the first oligo to the retrieval oligo when the first and retrieval oligos are in close proximity to each other and ligating the second oligo to the retrieval oligo when the second and retrieval oligos are in close proximity to each other. In some embodiments, the methods include incubating the composition under conditions sufficient for the ligation of the first oligo to the retrieval oligo when the first and retrieval oligos are in close proximity to each other and ligation of the second oligo to the retrieval oligo when the second and retrieval oligos are in close proximity to each other.

In some embodiments, the ligation of the oligos utilizes splint ligation. Splint ligation includes the addition of one or more splint or bridging oligos, which may be RNA or DNA, that can base-pair with the oligo of the antibody-oligo construct and the oligo linked to the retrieval tag binder. It is contemplated that many different ligases can be used in the methods of the disclosure, depending on the end composition of the oligos to be ligated. For example, the antibody-linked oligo and the retrieval tag binder-linked oligo may have a 3' hydroxyl and a 5'phosphate that are in close proximity together due to the association of the molecular construct and the protein of interest. A ligase can then be added to ligate the free 3'OH and 5'phosphate to form a single strand that can then be primed for amplification and/or probed with a fluorescent probe.

It is contemplated that any suitable ligase may be used and easily selected by one skilled in the art. Exemplary ligases include *E. coli* DNA ligase, T4 DNA ligase, mammalian ligases, and thermostable ligases. Embodiments of the disclosure may also include incubation of one or more assay components with a phosphatase. For example, embodiments include incubation of one or more of the molecular construct, the antibody-oligo construct, the retrieval tag binder-oligo construct, a primer, or probe with a phosphatase. The incubation may be a pre-incubation, meaning that it takes place prior to contact with the composition.

In some embodiments, the methods further comprises the addition of a uracil-specific excision reagent (USER) enzyme that generates a single nucleotide gap at the location of a uracil and can be utilized for breading down the splint/bridging oligos.

After ligation of the oligos, the double-stranded nucleic acid can then undergo a pre-amplification step, followed by a further amplification technique. In some embodiments, the one or more bridging oligos may form a circle that can then be used in rolling circle amplification (see, for example, FIG. 1B). In some embodiments, the pre-amplification step and further amplification technique comprises polymerase chain reaction. Accordingly, methods of the disclosure may include one or more of the following steps: contacting the composition with a polymerase (e.g., DNA or RNA polymerase), contacting the composition with one or more primers, contacting the composition with a buffer solution, contacting the composition with bivalent cations such as magnesium or manganese, and/or contacting the composition with deoxynucleoside triphosphates.

B. Sequencing

Aspects of the disclosure may include sequencing nucleic acids to determine the expression level of total protein or to determine/quantify the amount of an amplified region of an oligo of the disclosure, such as a first or second (or further oligo) or barcode region thereof. Described below are exemplary methods for performing such sequencing reactions.

Massively Parallel Signature Sequencing (MPSS).

The first of the next-generation sequencing technologies, massively parallel signature sequencing (or MPSS), was developed in the 1990s at Lynx Therapeutics. MPSS was a bead-based method that used a complex approach of adapter ligation followed by adapter decoding, reading the sequence in increments of four nucleotides. This method made it susceptible to sequence-specific bias or loss of specific sequences. Because the technology was so complex, MPSS was only performed 'in-house' by Lynx Therapeutics and no DNA sequencing machines were sold to independent laboratories. Lynx Therapeutics merged with Solexa (later acquired by Illumina) in 2004, leading to the development of sequencing-by-synthesis, a simpler approach acquired from Manteia Predictive Medicine, which rendered MPSS obsolete. However, the essential properties of the MPSS output were typical of later "next-generation" data types, including hundreds of thousands of short DNA sequences. In the case of MPSS, these were typically used for sequencing cDNA for measurements of gene expression levels. Indeed, the powerful Illumina HiSeq2000, HiSeq2500 and MiSeq systems are based on MPSS.

2. Polony Sequencing.

The Polony sequencing method, developed in the laboratory of George M. Church at Harvard, was among the first next-generation sequencing systems and was used to sequence a full genome in 2005. It combined an in vitro paired-tag library with emulsion PCR, an automated microscope, and ligation-based sequencing chemistry to sequence an *E. coli* genome at an accuracy of >99.9999% and a cost approximately ⅑ that of Sanger sequencing. The technology was licensed to Agencourt Biosciences, subsequently spun out into Agencourt Personal Genomics, and eventually incorporated into the Applied Biosystems SOLiD platform, which is now owned by Life Technologies.

3. 454 Pyrosequencing.

A parallelized version of pyrosequencing was developed by 454 Life Sciences, which has since been acquired by Roche Diagnostics. The method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence readouts. This technology provides intermediate read length and price per base compared to Sanger sequencing on one end and Solexa and SOLiD on the other.

4. Illumina (Solexa) Sequencing.

Solexa, now part of Illumina, developed a sequencing method based on reversible dye-terminators technology, and engineered polymerases, that it developed internally. The terminated chemistry was developed internally at Solexa and the concept of the Solexa system was invented by Balasubramanian and Klennerman from Cambridge University's chemistry department. In 2004, Solexa acquired the company Manteia Predictive Medicine in order to gain a massively parallel sequencing technology based on "DNA Clusters", which involves the clonal amplification of DNA on a surface. The cluster technology was co-acquired with Lynx Therapeutics of California. Solexa Ltd. later merged with Lynx to form Solexa Inc.

In this method, DNA molecules and primers are first attached on a slide and amplified with polymerase so that local clonal DNA colonies, later coined "DNA clusters", are formed. To determine the sequence, four types of reversible terminator bases (RT-bases) are added and non-incorporated nucleotides are washed away. A camera takes images of the fluorescently labeled nucleotides, then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to one human genome equivalent at 1× coverage per hour per instrument, and one human genome re-sequenced (at approx. 30×) per day per instrument (equipped with a single camera).

5. SOLiD Sequencing.

Applied Biosystems' (now a Thermo Fisher Scientific brand) SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

6. Ion Torrent Semiconductor Sequencing.

Ion Torrent Systems Inc. (now owned by Thermo Fisher Scientific) developed a system based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

7. DNA Nanoball Sequencing.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects.

8. Heliscope Single Molecule Sequencing.

Heliscope sequencing is a method of single-molecule sequencing developed by Helicos Biosciences. It uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, up to 55 bases per run, but recent improvements allow for more accurate reads of stretches of one type of nucleotides. This sequencing method and equipment were used to sequence the genome of the M13 bacteriophage.

9. Single Molecule Real Time (SMRT) Sequencing.

SMRT sequencing is based on the sequencing by synthesis approach. The DNA is synthesized in zero-mode waveguides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide at its incorporation into the DNA strand, leaving an unmodified DNA strand. According to Pacific Biosciences, the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases.]

C. Protein Assays

In some embodiments, the gene or protein expression of a protein of interest is measured. Methods for measuring transcription and/or translation of a particular gene sequence or biomarker are well known in the art. See, for example, Ausubel, Current Protocols in Molecular Biology, 1987-2006, John Wiley & Sons; and Sambrook and Russell, Molecular Cloning: A Laboratory Manual, 3rd Edition, 2000.

Polypeptides from the protein of interest encoded by a gene can be detected and/or quantified by any methods known to those of skill in the art from samples as described herein. In some embodiments, antibodies can also be used to detect polypeptides/proteins of interest. Antibodies to a protein of interest can be produced using well known techniques (see, e.g., Harlow & Lane, 1988 and Harlow & Lane, 1999; Coligan, 1991; Goding, 1986; and Kohler & Milstein, 1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989).

Once specific antibodies are available, the expression of a protein of interest can be detected by a variety of immunoassay methods. For a review of immunological and immunoassay procedures, see Basic and Clinical Immunology (1991). Moreover, the immunoassays of certain aspects can be performed in any of several configurations, which are reviewed extensively in Enzyme Immunoassay (1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., 1973; Akerstrom et al., 1985). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., 1986).

Any suitable method can be used to detect one or more of the markers described herein. Successful practice can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g., sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)11, atmospheric pressure photoionization mass spectrometry (APPI-MS), APPI-MS/MS, and APPI-(MS)n, quadrupole mass spectrometry, Fourier transform mass spectrometry (FTMS), and ion trap mass spectrometry, where n is an integer greater than zero.

Detection methods may include the use of a biochip array. Biochip arrays include protein and polynucleotide arrays. The protein of interest may be captured on the biochip array and subjected to analysis to detect the level of the protein in a sample.

D. Nucleic Acid Assays

Aspects of the methods include assaying nucleic acids to determine expression levels. Arrays can be used to detect differences between two samples. An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

In addition to the use of arrays and microarrays, it is contemplated that a number of difference assays could be employed to analyze expressed nucleic acids. Such assays include, but are not limited to, nucleic amplification, polymerase chain reaction, quantitative PCR, RT-PCR, in situ hybridization, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing), PAP (Pyrophosphorolysis-activation polymerization), next generation RNA sequencing, northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

Embodiments of the disclosure relate to determining the expression of a protein of interest or of a nucleic acid comprising a barcode or protein of interest-specific region. The expression or abundance level can be determined by measuring the levels of RNA transcripts of a protein of interest or the abundance of amplified nucleic acids comprising a barcode. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from cells can be amplified to cDNA or cRNA before detection and/or quantitation. The isolated RNA can be either total RNA or mRNA. The RNA amplification can be specific or non-specific. In some embodiments, the amplification is specific in that it specifically amplifies a gene for a protein of interest. In some embodiments, the amplification and/or reverse transcriptase step excludes or includes random priming. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes can be prepared to be complementary to a barcode region or oligo described herein. The term "primer" or "probe" as used herein, is meant to encompass any nucleic acid that is capable of priming the synthesis of a nascent nucleic acid in a template-dependent process and/or pairing with a single strand of an oligo of the disclosure, or portion thereof. Typically, primers are oligonucleotides from ten to twenty and/or thirty nucleic acids in length, but longer sequences can be employed. Primers may be provided in double-stranded and/or single-stranded form, although the single-stranded form is preferred.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used to increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene described herein. Particularly, each probe/primer has relatively high sequence complexity and does not have any ambiguous residue (undetermined "n" residues). The probes/primers can hybridize to the target gene, including its RNA transcripts, under stringent or highly stringent conditions. In some embodiments, because each of the biomarkers has more than one human sequence, it is contemplated that probes and primers may be designed for use with each of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In one embodiment, quantitative RT-PCR (such as TaqMan, ABI) is used for detecting and comparing the levels or abundance of nucleic acids in samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable cDNAs may be normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in some samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

Representative methods and apparatus for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,525,464; 5,503,980; 5,510, 270; 5,525,464; 5,527,681; 5,529,756; 5,532,128; 5,545, 531; 5,547,839; 5,554,501; 5,556,752; 5,561,071; 5,571, 639; 5,580,726; 5,580,732; 5,593,839; 5,599,695; 5,599, 672; 5,610,287; 5,624,711; 5,631,134; 5,639,603; 5,654, 413; 5,658,734; 5,661,028; 5,665,547; 5,667,972; 5,695, 940; 5,700,637; 5,744,305; 5,800,992; 5,807,522; 5,830, 645; 5,837,196; 5,871,928; 5,847,219; 5,876,932; 5,919, 626; 6,004,755; 6,087,102; 6,368,799; 6,383,749; 6,617, 112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

III. Exemplary Utilities

A. Diagnostic and Therapeutic Methods

Method aspects of the disclosure may be used in diagnostics to evaluate a protein of interest in a patient in a specified functional form. For example, methods of the disclosure provide for a method of evaluating a protein of interest in a patient in a specified functional form, said method comprising: (i) contacting a biological sample from the patient with a molecular construct comprising: a targeting group operatively linked to a retrieval tag; wherein the targeting group specifically binds to the specified functional form of the protein of interest; (ii) contacting the composition with an antibody operatively linked to a first oligo; wherein the antibody specifically binds to the protein of interest; (iii) contacting the composition with a second molecular construct comprising a retrieval tag binder operatively linked to a retrieval oligo; (iv) incubating the composition under conditions sufficient for the ligation or annealing of the first oligo to the retrieval oligo when the first and retrieval oligos are in close proximity to each other; (v) detecting the ligated or annealed first and retrieval oligos.

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from ovarian or prostate tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is ovarian or prostate. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g., rectal) and one or more samples from another tissue (e.g., cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

The cancers referred to in the methods of the disclosure include, but are not limited to, tumors of all types, locations, sizes, and characteristics. Exemplary cancer types include, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, specific breast cancers such as ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, paget's disease of the nipple, phyllodes tumors of the breast, recurrent and/or metastatic breast, cancer, luminal A or B breast cancer, triple-negative/basal-like breast cancer, and HER2-enriched breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/ multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

B. Drug Discovery and Spatial Detection of Specified Functional Forms of Proteins The current methods of the disclosure may also be used to evaluate activity modifiers. As described and demonstrated in Example 1 of the application, the methods of the disclosure allow for the quantification of small molecule target engagement in live cells. The disclosed methods allow for a way to detect and quantify target engagement in live cells, particularly for enzyme targets that are resistant to traditional in vitro approaches, such as post-translationally modified, insoluble enzymes (e.g., NCEH1). Example 1 of the application also demonstrates that the methods can be used to quantify active enzymes with high spatial resolution. The methods provide for spatially resolved information on active enzymes (FIG. 3E-H), and preservation of sub-cellular information preferably employs cell-permeable activity probes to tag enzymes in their native environments as well as the subsequent coupling of probe and enzyme in signal amplification and detection.

IV. Kits

Certain aspects of the present disclosure also concern kits containing nucleic acids (e.g., oligos), vectors, molecular constructs, antibodies, ligation, primer extension, and amplification reagents, and/or retrieval tag/retrieval tag binder pairs of the disclosure. The kits may be used to implement the methods of the disclosure. In some embodiments, kits can be used to evaluate a specified functional form of a protein in a composition, such as a composition of cells or extracts thereof. In some embodiments, the kits can be used to evaluate proteins in live cells, according to methods of the disclosure. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, primers, or synthetic RNA molecules, or any value or range and combination derivable therein. In some embodiments, there are kits for evaluating the activation of or engagement of a receptor by a ligand. In some embodiments, universal probes or primers are included for amplifying, identifying, or sequencing a barcode or receptor. Such reagents may also be used to generate or test host cells that can be used in screens.

In certain embodiments, the kits may comprise materials for analyzing cell morphology and/or phenotype, such as histology slides and reagents, histological stains, alcohol, buffers, tissue embedding mediums, paraffin, formaldehyde, and tissue dehydrant.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide or polynucleotide detecting agents of the disclosure for drug discovery are contemplated.

In certain aspects, negative and/or positive control agents are included in some kit embodiments. The control molecules can be used to verify specific binding of a molecular construct or antibody to a protein of interest, or an amplification or ligation control, for example.

Embodiments of the disclosure include kits for analysis of a pathological sample by assessing a nucleic acid or polypeptide profile for a sample comprising, in suitable container means, two or more RNA probes or primers for detecting expressed polynucleotides. Furthermore, the probes or primers may be labeled. Labels are known in the art and also described herein. In some embodiments, the kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye. Kits can comprise any one or more of the following materials: enzymes, reaction tubes, buffers, detergent, primers, probes, antibodies. In some embodiments, these kits include the needed apparatus for performing RNA extraction, RT-PCR, and gel electrophoresis. Instructions for performing the assays can also be included in the kits.

The kits may further comprise instructions for using the kit for assessing expression, means for converting the expression data into expression values and/or means for analyzing the expression values to generate ligand/receptor interaction data.

Kits may comprise a container with a label. Suitable containers include, for example, bottles, vials, and test tubes. The containers may be formed from a variety of materials such as glass or plastic. The container may hold a composition which includes a probe that is useful for the methods of the disclosure. The kit may comprise the container described above and one or more other containers comprising materials desirable from a commercial and user standpoint, including buffers, diluents, filters, needles, syringes, and package inserts with instructions for use.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—an Activity-Dependent Proximity Ligation Platform for Spatially Resolved Quantification of Active Enzymes in Single Cells Integration of chemical probes into proteomic workflows enables the interrogation of protein activity, rather than abundance. Current methods limit the biological contexts that can be addressed due to sample homogenization, signal-averaging, and bias toward abundant proteins. This example describes a platform that integrates family-wide chemical probes with proximity-dependent oligonucleotide amplification and imaging to quantify enzyme activity in native contexts with high spatial resolution. Application of this method, activity-dependent proximity ligation (ADPL), to serine hydrolase and cysteine protease enzymes enables quantification of differential enzyme activity resulting from endogenous changes in localization and expression. In a competitive format, small molecule target engagement with endogenous proteins in live cells can be quantified. Finally, retention of sample architecture enables interrogation of complex environments such as cellular co-culture and patient samples. ADPL should be amenable to diverse probe and protein families to detect active enzymes at scale and resolution out of reach with current methods.

A. Results
1. ADPL Quantifies Active Enzymes with High Spatial Resolution ADPL integrates the activity-dependent and family-wide tagging of endogenous, active enzymes afforded by chemical probes, with the specific and robust signal amplification afforded by barcoded oligonucleotide proximity ligation and amplification (FIG. 1). In contrast to the majority of studies that only use chemical probes in homogenized cell lysate, the inventors sought to tag active enzymes in their native environment, and thus they performed ADPL by pulsing live cells with a family-wide probe (FIG. 1A). Whole fixed cells are then labeled with probe-specific and protein-of-interest (POI)-specific antibodies, and subsequently secondary antibodies conjugated to barcoded, single stranded oligonucleotide sequences (FIG. 1B). In this way the chemical probe provides a significant narrowing of the proteome under study, and the POI antibody allows for deconvolution of signal from a family-wide probe, which may have tagged hundreds of proteins, to that from just one protein. Subsequent incubation with sequence-specific bridging oligonucleotides allows for ligation and rolling circle amplification of probe-labeled target proteins (FIG. 1C). Finally, ADPL signal is detected by incubating with a complementary, fluorophore-labeled oligonucleotide and fluorescence microscopy (FIG. 1C, D). In summary, ADPL seeks to provide a highly specific, selective, amplified fluorescent signal for an active protein-of-interest within the preserved complex cellular environment.

Figure 2:
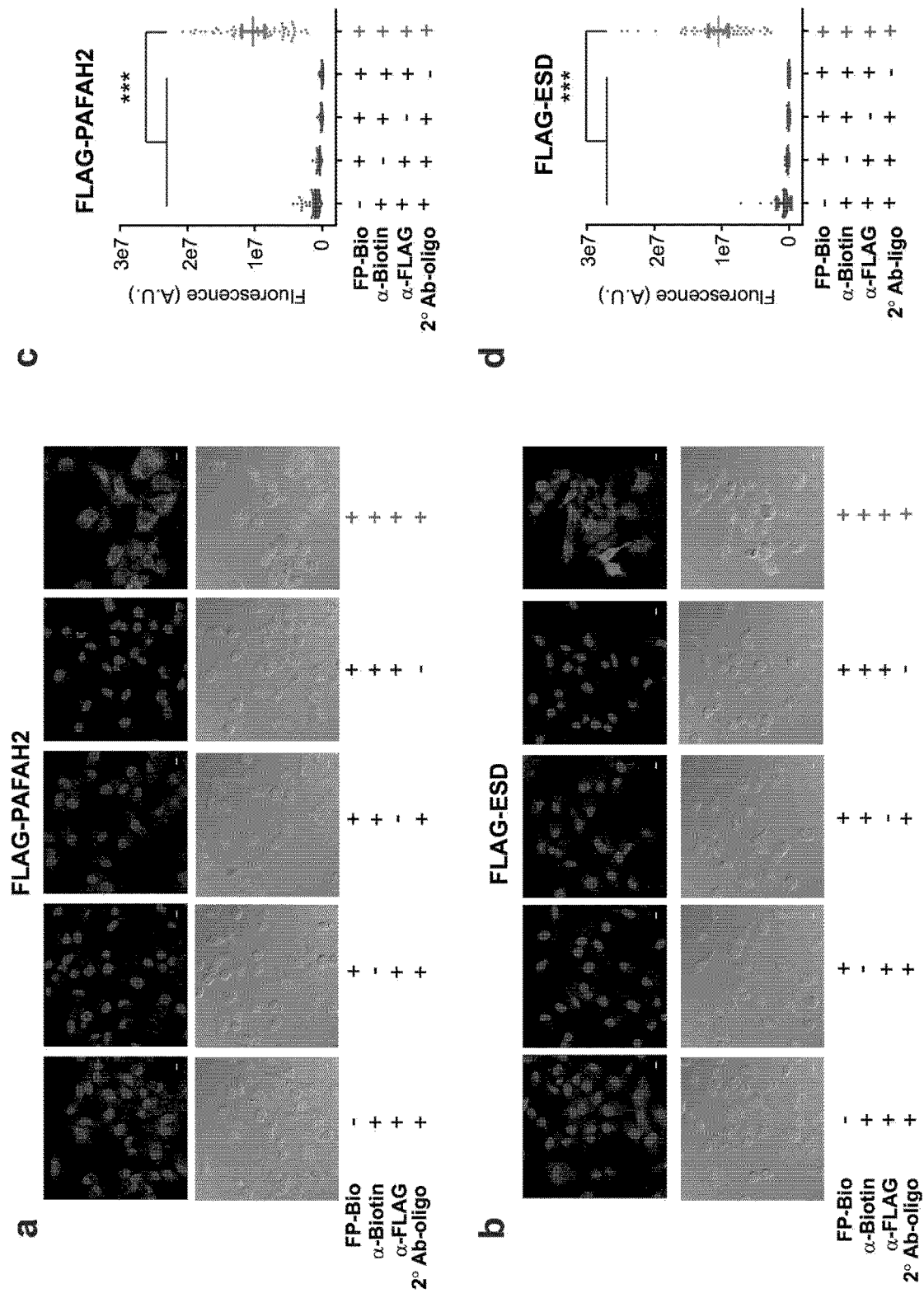
FIG. 2A-D. Modular, specific detection of active serine hydrolases by ADPL imaging. (a, b) Representative ADPL detection and visualization of active FLAG-PAFAH2 (a) and FLAG-ESD (b) in PC3 cells in the presence or absence of the indicated ADPL components. Channels shown are DAPI nuclear stain (blue), ADPL signal (red) and overlayed signal on light field images. (c, d) Quantified single cell ADPL fluorescent signal from active FLAG-PAFAH2 (c) and FLAG-ESD (d) in the presence or absence of indicated ADPL components, demonstrating the probe- and POI-dependent nature of a robust ADPL signal. Quantification of signal in c: minus FP-Bio (n=76), minus α-biotin (n=73), minus α-FLAG (n=89), minus 2° antibody-oligo (n=87), positive ADPL (n=53). Quantification in d: minus FP-Bio (n=64), minus α-biotin (n=68), minus α-FLAG (n=63), minus 2° antibody-oligo (n=63), positive ADPL (n=50). Unpaired t-test results in c, d are between individual ADPL conditions in the absence of one component and the positive ADPL condition containing all components. ***$P<0.001$, Student's t-test. Representative images are from triplicate technical replicates of two or more independent biological experiments. Each dot represents a single cell fluorescence measurement, center line and whiskers denote the mean and 95% C.I. of the population, respectively. Scale bars=10 μm.
Figure 7:
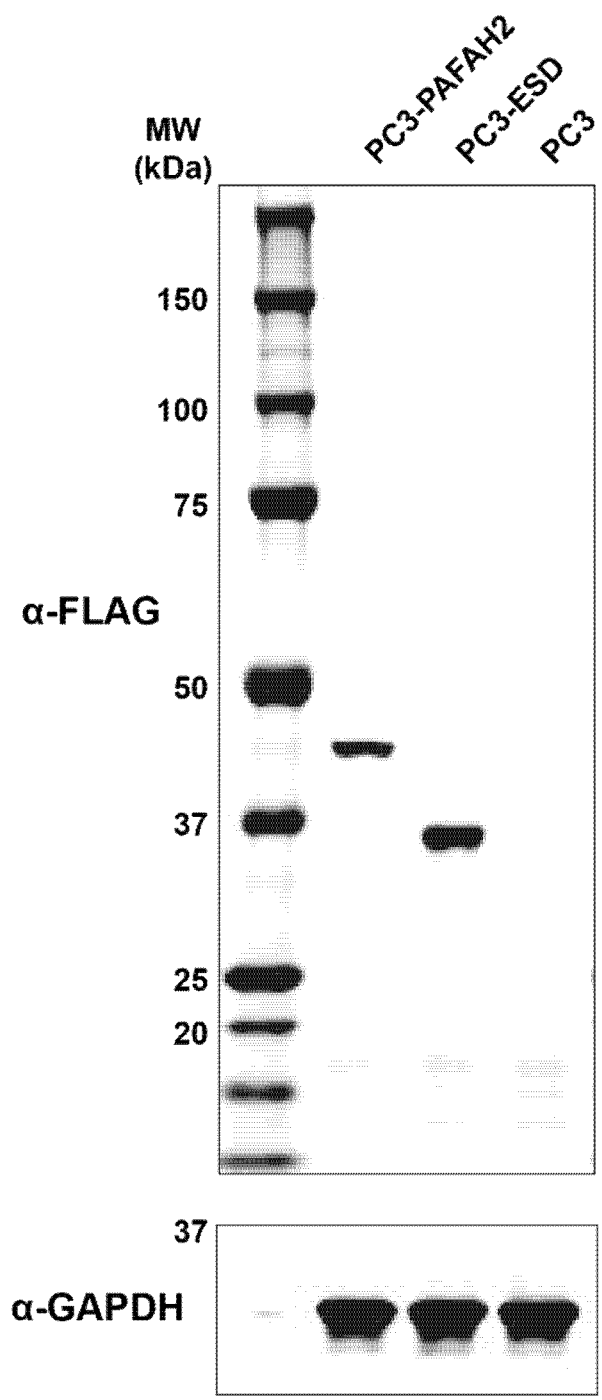
FIG. 7. Characterization of serine hydrolase expressing stable cell lines. α-FLAG and α-GAPDH Western blots of FLAG-PAFAH2 expressing, FLAG-ESD expressing, and wild-type PC3 stable cells. Data are representative of two technical replicates in duplicate biological experiments.
Figure 8:
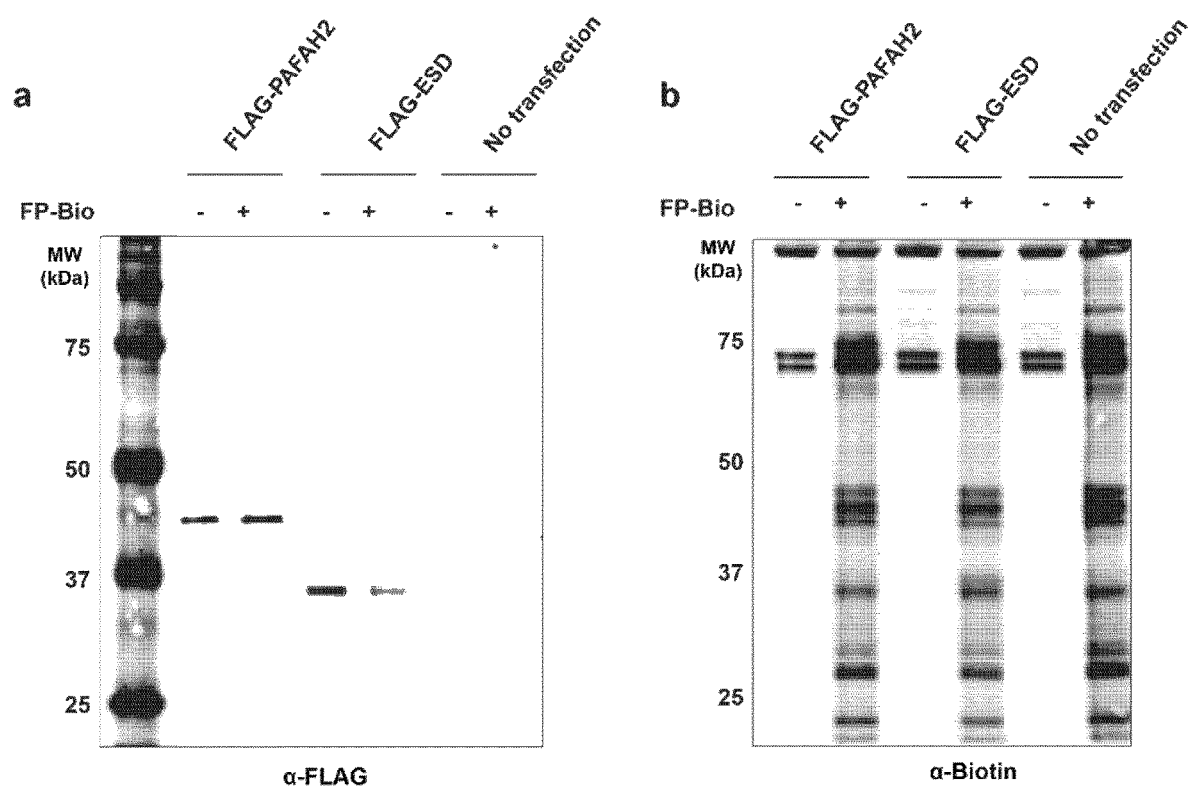
FIG. 8A-B. Detection of transfected active serine hydrolases in cell lysate by gel-based chemical proteomics. (a) α-FLAG western blot for cell lysates of FLAG-PAFAH2 transfected, FLAG-ESD transfected, and negative transfected HeLa cell lysates which were compared in pair between without probe pulsed and with probe pulsed. (b) α-Biotin western blot "gel-based" profiling of serine hydrolase activity in the FLAG-PAFAH2 transfected, FLAG-ESD transfected, negative transfected HeLa cell lysates which were compared in pair between without probe pulsed and with probe pulsed. Representative data are from two technical replicates of two biological experiments.

To test this approach within a well-characterized enzyme family, the inventors employed a fluorophosphonate-biotin (FP-Bio) chemical probe that covalently modifies active serine hydrolase enzymes, of which there are approximately 200 in mammalian cells. The inventors first tested whether the ADPL platform could specifically detect the activity of two soluble serine hydrolase enzymes, platelet-activating factor acetylhydrolase 2 (PAFAH2) and esterase D (ESD). PC3 prostate cancer cells stably expressing FLAG-tagged PAFAH2 and ESD were pulsed with FP-Bio and processed for ADPL with an anti-FLAG antibody (FIG. 2A; FIG. 7). Cells treated with FP-Bio and fully processed for ADPL exhibited intense fluorescence signal throughout the cytosol, consistent with predicted PAFAH2 and ESD localization (data not shown). Omission of any component or step in the ADPL protocol resulted in significant reversion of signal to background. Relative quantification of the ADPL signal for these enzyme targets yielded highly significant signal increases of ~10-to-250-fold for both PAFAH2 and ESD, relative to background (data not shown). To determine whether ADPL could identify and detect distinct cellular phenotypes within a heterogeneous cellular population, PAFAH2 and ESD were expressed in HeLa cells via transient transfection, resulting in mixtures of positive (transfected) and negative expressing (untransfected) cells. ADPL imaging was able to differentiate both PAFAH2-expressing and ESD-expressing cells that, between or within an experiment, exhibited significant increases in signal of ~12-to-900-fold over negative cells (FIG. 3A-D). Notably, gel-based profiling, which relies on averaging over many thousands of cells, was unable to detect the presence of these outlier cells when a heterogeneous cell population was present (FIG. 8A, B), highlighting the ability of ADPL to provide quantitative enzyme activity information at single-cell resolution.

Figure 3:
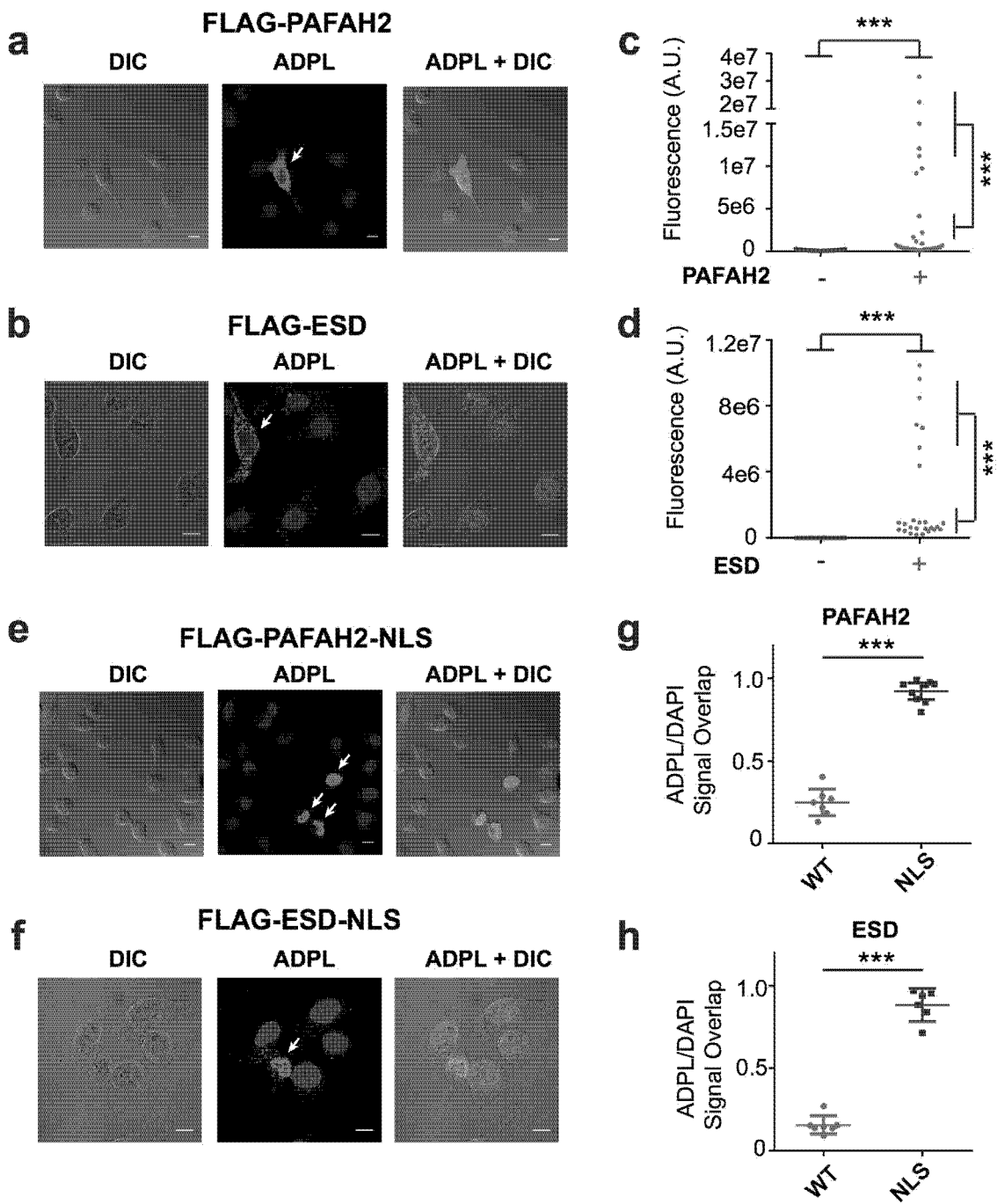
FIG. 3A-H. ADPL imaging detects intercellular and intracellular localization of active enzymes. (a, b) Representative ADPL images of HeLa cells transiently transfected with FLAG-PAFAH2 (a) or FLAG-ESD (b); representative outlier cells exhibiting strong ADPL signal and used for quantification of positive cells are denoted by white arrows. (c, d) Quantified single cell ADPL fluorescent signals from representative fields of non-transfected cells and the entire population of cells transfected with FLAG-PAFAH2 (c) and FLAG-ESD (d). Statistical evaluations shown are comparing mean ADPL signal from positive, transfected cells to the entire field of non-transfected cells (top comparison in both c and d) and negative cells within the same experiment (right in c and d). Quantification of signal in c: negative transfection (n=31), positive transfection (n=33). Quantification of signal in d: negative transfection (n=28), positive transfection (n=26). Denoted 'n' values indicate total number of cells in each analysis group. (e, f) Representative ADPL images of HeLa cells transiently transfected with hydrolases tagged with a nuclear localization sequences: NLS-PAFAH2 (e) and NLS-ESD (f); representative outlier cells exhibiting strong ADPL signal and used for quantification of positive cells are denoted by white arrows. (g, h) Quantification of the ADPL/DAPI fluorescence signal overlay in positive cells, which is a representation of nuclear localization. WT: wild-type FLAG-PAFAH2 or FLAG-ESD transfection, as shown in a and b, respectively. NLS: NLS-PAFAH2 or NLS-ESD transfection, as shown in e and f, respectively. Quantification of signal in e: WT (n=7), NLS (n=9). Quantification of signal in f: WT (n=7), NLS (n=6). Scale bars=10 μm in all images. Blue channel: DAPI nuclear; red channel: ADPL signal; gray channel: DIC. ***Student's t-test. Each dot represents a single cell fluorescence measurement, center line and whiskers denote the mean and 95% C.I. of the population, respectively. Representative images are from triplicate technical replicates of two or more independent biological experiments.

Localization of biomolecules to distinct sub-cellular compartments and complexes can have a significant impact on protein function, however the simultaneous detection of activity and localization is challenging with current approaches. To determine if ADPL could detect the sub-cellular localization of active enzymes, the cytosolic PAFAH2 and ESD enzymes were tagged with a C-terminal nuclear localization sequence (NLS) and transiently expressed in parallel with the wild-type enzymes. A minority of ADPL signal from wild-type PAFAH2 (~25%) and ESD (~16%) overlapped with the DAPI nuclear signal in a central cellular z-plane (FIG. 3G, H). In contrast, the vast majority of PAFAH2-NLS (~92%) and ESD-NLS (~88%) ADPL signals were localized to the nuclear compartment, confirming that ADPL provides spatially resolved information on active enzymes (FIG. 3E-H). The inventors speculate that preservation of sub-cellular information is dependent upon the use of cell-permeable activity probes to tag enzymes in their native environments as well as the subsequent coupling of probe and enzyme in signal amplification and detection.

2. ADPL Quantifies Endogenous Determinants of Enzyme Activity

Figure 4:
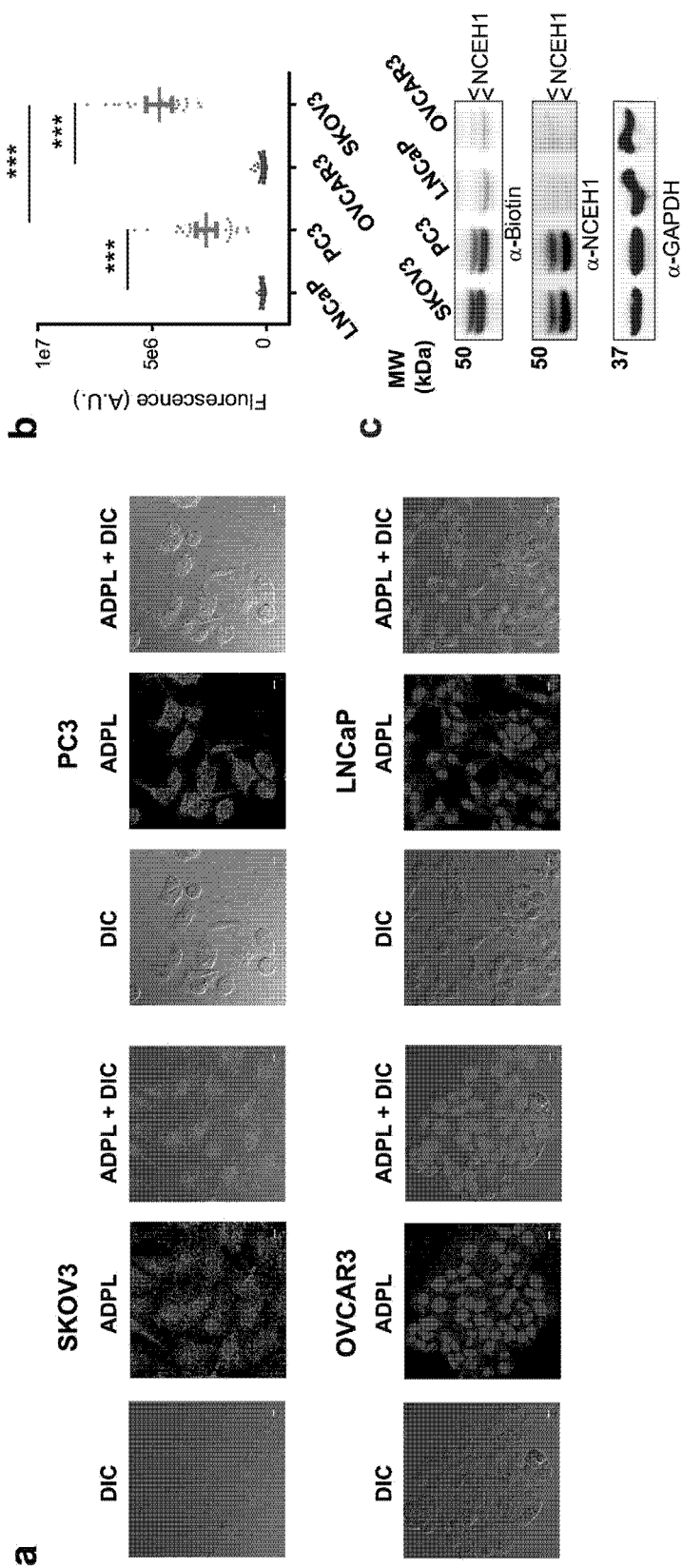
FIG. 4A-C. ADPL profiling of differential enzyme activity correlated with distinct phenotypes in native contexts. (a) Representative ADPL images measuring endogenous NCEH1 activity in paired aggressive (SKOV3 and PC3) and non-aggressive (OVCAR3 and LNCaP) cancer cell lines from ovarian and prostate cancers, respectively. (b) Relative quantification of NCEH1 activity in each cell line from a. Statistical evaluations shown are comparing mean ADPL signal between non-aggressive and aggressive cells within each tissue of origin. Quantification in b: LNCaP (n=47), PC3 (n=43), OVCAR3 (n=60), SKOV3 (n=35). (c) α-Biotin western blot "gel-based" profiling of serine hydrolase activity in the four cell lines is shown. The two bands at approximately 42 and 45 kDa are glycoforms of NCEH1; the overlapped intermediate band is another enzyme family member. α-NCEH1 immunoblotting indicates protein abundance. α-GAPDH immunoblotting from the same experiment is shown as a loading control. Scale bars=10 μm in all images. Blue channel: DAPI nuclear; red channel: ADPL signal; gray channel: DIC. ***$P<0.001$, Student's t-test. Each dot represents a single cell fluorescence measurement, center line and whiskers denote the mean and 95% C.I. of the population, respectively. Representative images are from quadruplicate technical replicates of three or more independent biological experiments.
Figure 9:
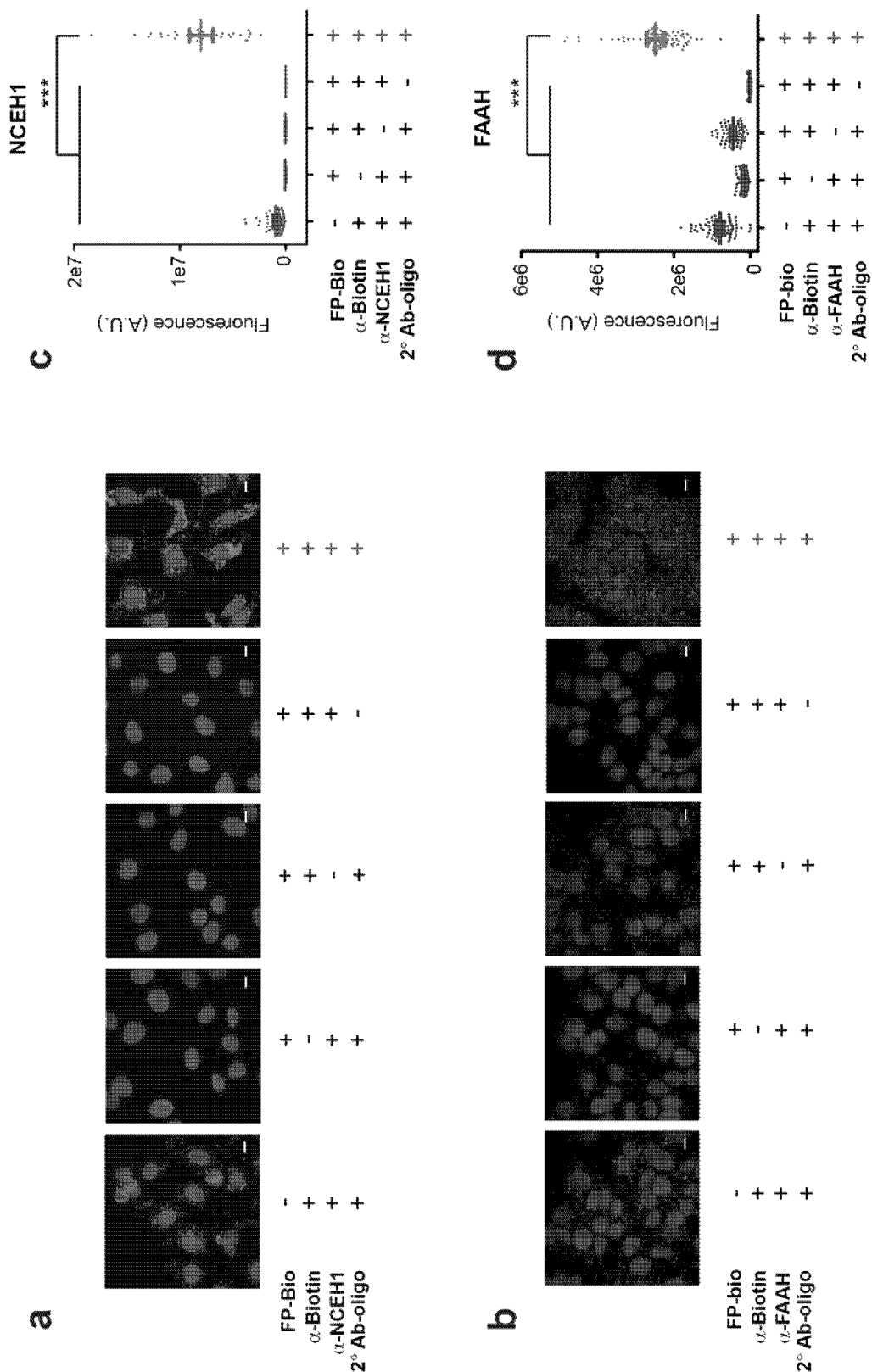
FIG. 9A-D. Specific detection of endogenous, active serine hydrolases NCEH1 and FAAH by ADPL imaging. (a, b) Representative ADPL detection and visualization of NCEH1 in SKOV3 cells (a) or FAAH in MCF7 cells (b) in the presence or absence of indicated ADPL components. Channels shown are DAPI nuclear stain (blue), ADPL signal (red). (c, d) Quantified single cell ADPL fluorescent signal from active NCEH1 (c) or FAAH (d) in the presence or absence of indicated ADPL components, demonstrating the probe- and POI-dependent nature of robust ADPL signal. Quantification of signal in b: minus FP-Bio treatment (n=55), minus α-biotin (n=37), minus α-NCEH1 (n=34), minus 2° antibody oligo (n=42), positive ADPL (n=38). Quantification of signal in d: minus FP-Bio treatment (n=74), minus α-biotin (n=79), minus α-FAAH (n=69), minus 2° antibody oligo (n=72), positive ADPL (n=67). Unpaired t-test results in b and d are between individual ADPL conditions in the absence of one component and the positive ADPL condition containing all components. ***P<0.001. Each dot represents a single cell fluorescence measurement, center line and whiskers denote the mean and 95% C.I. of the population, respectively. Scale bars=10 Data are representative of four or more technical replicates in three or more biological replicates.

The inventors next sought to determine whether this proteomic approach could be used to visualize and quantify endogenous active enzymes in cells. Furthermore, it was wondered if ADPL could enable interrogation of enzymes that are resistant to the typical biochemical workflow of orthogonal expression, purification and isolated study with in vitro assays. Neutral cholesterol ester hydrolase 1 (NCEH1, also known as AADACL1 and KIAA1363) is a single-pass transmembrane, differentially glycosylated serine hydrolase implicated in cholesterol ester as well as neutral ether lipid metabolism. The activity of this enzyme has been studied in membrane homogenates from tissues and cells, however it is an example of an enzyme that has not been studied in isolation with typical in vitro biochemical approaches. Similar to the results obtained with FLAG-tagged enzymes, an ADPL workflow coupling the family-wide FP-Bio probe and anti-NCEH1 antibodies detected active NCEH1 in SKOV3 ovarian cancer cells (FIG. 9A, B). Previous studies have shown high NCEH1 activity in aggressive tumor cell lines from diverse tissues, whereas less aggressive cell lines display 10-to-20-fold lower enzyme activity. Additionally, high NCEH1 activity has been correlated with tumorigenicity in primary human breast tumors. The inventors thus profiled paired low- and high-aggressiveness cell lines to determine if ADPL could detect and quantify endogenous changes in enzyme activity that correlate with cellular phenotypes. ADPL signal from active NCEH1 enzymes was found to be significantly higher in the more tumorigenic ovarian (SKOV3) and prostate (PC3) cancer cell lines relative to the less-aggressive OVCAR3 and LNCaP cells from the same tissues of origin (FIG. 4A, B). The qualitative differences between these distinct cell lines was apparent in ADPL images; the mean relative differences in NCEH1 activity between the aggressive/non-aggressive pairs from prostate and ovarian cancer cells were 18- and 35-fold, respectively. By comparison, gel-based profiling of NCEH1 signal generated from whole cell lysate exhibited mean fold-changes of 7- and 18-fold between these same cell line pairs measured by FP-Bio Western blot, which was similar to detected changes in total NCEH1 protein abundance by Western blot (FIG. 4C). Gel-based profiling also revealed modest differences in NCEH1 activity between the two aggressive cancer cell lines, with SKOV3 cells exhibiting an ~1.6-fold increase relative to PC3 cells. Indeed, this difference was detected by ADPL, with SKOV3 cells showing a statistically significant difference of 1.8-fold increased NCEH1 activity, compared to PC3 cells. Relative to gel-based profiling, the ability to quantify signal at the single cell level, compared to roughly $10^6$ cells needed for the profile in 4 C, enables interrogation of cell population heterogeneity and detection of distinct phenotypes (e.g., FIG. 3A). Additionally, co-migration of other enzyme family members complicates accurate quantification of gel-based signal to a specific enzyme, which is exemplified by a serine hydrolase that co-migrates with the two glycoforms of NCEH1 (FIG. 4C). Together these data establish that the ADPL workflow captures quantitative endogenous variation in enzyme activity in distinct biological states, and comparison with averaged activity-based profiling gels validates that single cell ADPL data can quantify differences that range from modest (~1.5-fold) to robust (>10-fold).

Figure 10:
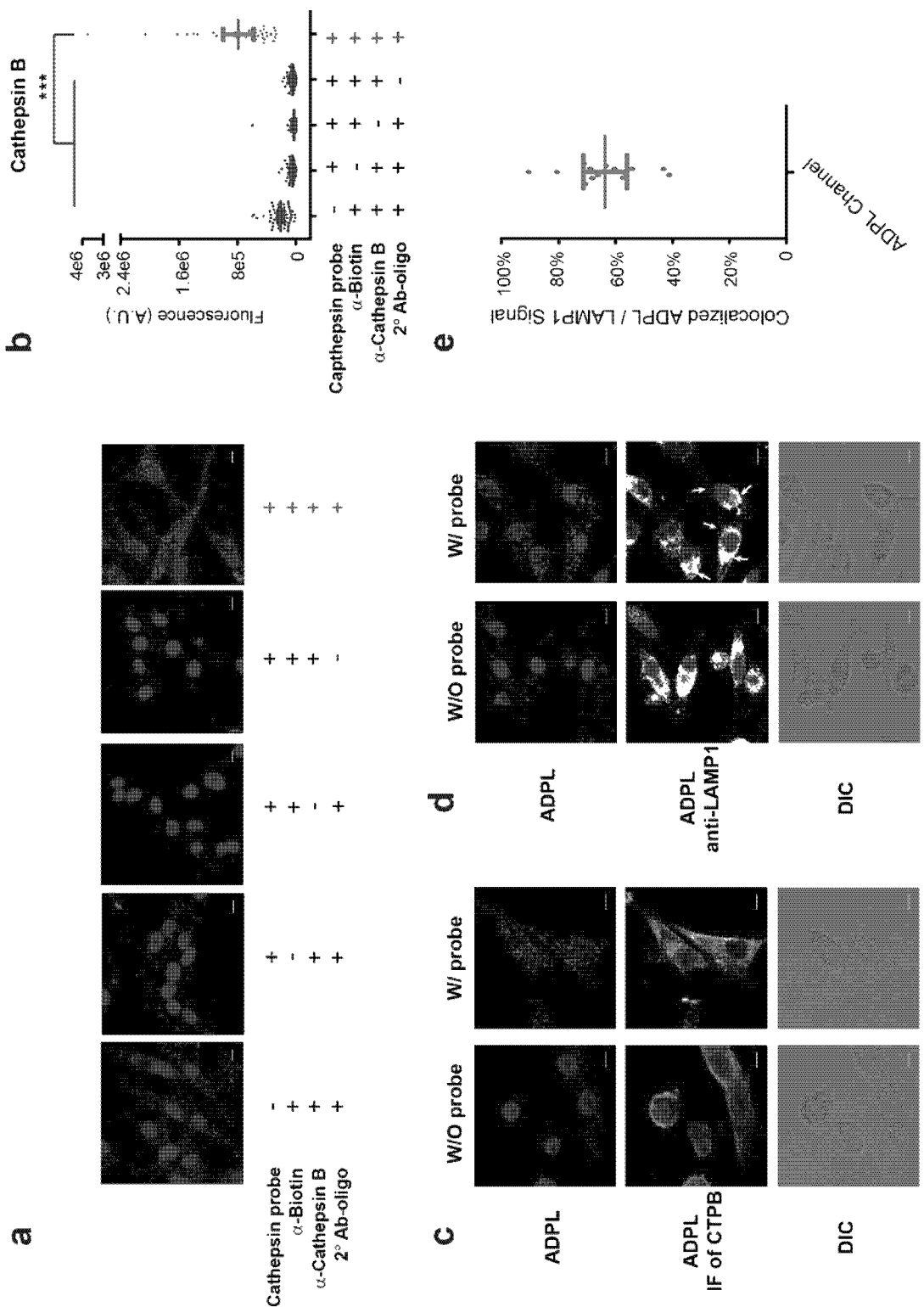
FIG. 10A-E. Specific detection of endogenous, active cysteine hydrolases cathepsin B by ADPL imaging and characterizing the localization of ADPL signal of cathepsin B. (a) Representative ADPL detection and visualization of cathepsin B in U87 cells in the presence or absence of indicated ADPL components. Channels shown are DAPI nuclear stain (blue), ADPL signal (red). (b) Quantified single cell ADPL fluorescent signal from active cathepsin B in the presence or absence of indicated ADPL components, demonstrating the probe- and POI-dependent nature of robust ADPL signal. Quantification of signal in b: minus FP-Bio treatment (n=54), minus α-biotin (n=70), minus α-cathepsin B (n=63), minus 2° antibody oligo (n=57), positive ADPL (n=39). Characterizing the localization of ADPL signal of cathepsin B in U87 cells. (c) Co-localization analysis of ADPL and immunofluorescence detection of cathepsin B without (w/o) and with (w/) probe. (d) Co-localization analysis of ADPL and lysosome marker anti-LAMP1 Alexa Fluor® 647 without (w/o) and with (w/) probe. White arrows indicate the co-localized ADPL signal; yellow arrows indicate the signal outside LAMP1-stained lysosomes. (e) Quantification of the percentage of ADPL signal in lysosome on a per-cell basis. Unpaired t-test results in b are between individual ADPL conditions in the absence of one component and the positive ADPL condition containing all components. ***P<0.001. Each dot represents a single cell fluorescence measurement, center line and whiskers denote the mean and 95% C.I. of the population, respectively. Scale bars=Data are representative of four or more technical replicates in three or more biological replicates.

To test whether ADPL could be applied to other protein families and probe classes, the inventors also utilized a cell-permeable, family-wide probe targeting cathepsins, a subfamily of cysteine proteases. In particular, the activity of Cathepsin B in U87 glioblastoma cells was assessed by ADPL, and results similar to those observed for serine hydrolases were found (FIG. 10A, B). Antibody-based immunofluorescent (IF) staining of cathepsin B (CTBP) protein revealed signal distributed evenly throughout the cytosol (FIG. 10C). ADPL signal from CTBP, in contrast, was more restricted to foci that predominantly co-localized with LAMP1+ lysosomes (FIG. 10D,E). These results demonstrate the notion that ADPL simultaneously measures protein activity and location, which in the case of CTBP has been shown to occur primarily in the low pH environment of endolysosomal compartments. Immunofluorescence and other proteomic approaches, on the other hand, indiscriminately report on both active and inactive proteins. These results, and the modular nature of this ADPL platform suggest that ADPL should be applicable to diverse protein families and probe classes.

Figure 5:
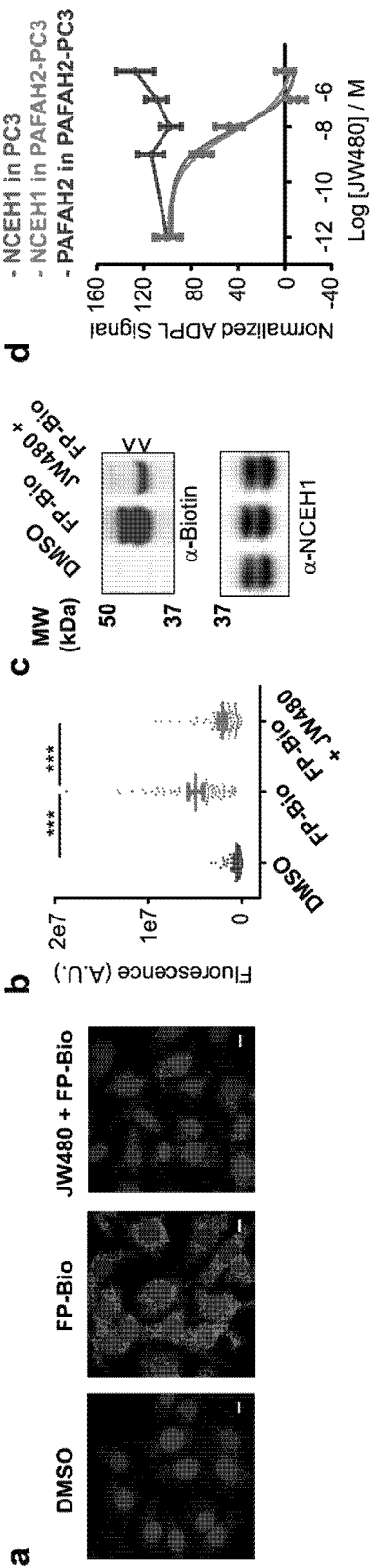
FIG. 5A-D. ADPL detects active enzymes and the specific action of small molecule inhibitors. (a, b) Representative ADPL images (a) and quantification (b) of endogenous NCEH1 activity in SKOV3 cells with no FP-Bio probe treatment (DMSO), with FP-Bio and with FP-Bio after pre-treatment of live cells with the specific NCEH1 inhibitor JW480 (1 μM, 4 hr). Quantification in b: DMSO (n=73), FP-Bio (n=73), FP-Bio+JW480 (n=79). (c) α-Biotin Western blot "gel-based" profiling of NCEH1 activity from conditions in a show that while NCEH1 is present in all conditions, JW480 specifically inhibits labeling of NCEH1 by the FP-Bio. (d) Quantification of NCEH1 activity by ADPL in wild-type or PAFAH2 expressing PC3 cells treated with JW480 prior to ADPL imaging. $IC_{50}$ curves exhibit potent and precise inhibition of NCEH1 by JW480 in wild-type PC3 cells ($IC_{50}$=6 nM) and PAFAH2 expressing PC3 cells ($IC_{50}$=8 nM). Parallel quantification of PAFAH2 activity in the stable PC3 cell line shows no effect of JW480 over the same dose-range. In b each point represents a single cell fluorescence measurement, center line and whiskers denote the mean and 95% C.I. of the population, respectively. Sigmoidal $IC_{50}$ curves in d were generated in Prism 6 software, with center lines and error bars denoting mean and s.e.m. Scale bars=10 μm in all images. Blue channel: DAPI nuclear; red channel: ADPL signal; gray channel: DIC. ***$P<0.001$, Student's t-test. Data are from quadruplicate technical replicates in two or more biological experiments.

3. ADPL Enables Quantification of Small Molecule Target Engagement in Live Cells In certain embodiments, a key advantage of activity-based probes is their dependence upon the catalytic integrity of target proteins. This requisite connection between protein activity and probe signal enables the quantification of endogenous changes in protein activity, for example caused by post-translational modification of a given target, as well as the action of exogenous agents, such as small molecule drugs. To understand whether ADPL is indeed reporting on the activity of target proteins, rather than abundance, the inventors sought to detect and quantify the effects of small molecule inhibitors with ADPL. First, SKOV3 cells were treated with 1 µM of an NCEH1-selective small molecule inhibitor, JW480, prior to pulse labeling with FP-Bio and ADPL processing. NCEH1 activity in JW480-treated cells was significantly reduced relative to those treated with vehicle alone, which was apparent by both ADPL imaging and quantification (FIG. 5A, B). Parallel gel-based profiling from homogenized cells likewise revealed significant and selective inhibition of NCEH1 activity with JW480 treatment, despite equivalent NCEH1 protein levels across these conditions (FIG. 5C). Treatment of cells with JW480 also demonstrated dose-dependent inhibition of NCEH1, with an apparent $IC_{50}$=6 nM and 8 nM in PC3 and PAFAH2-expressing PC3 cells, respectively (FIG. 5D). These $IC_{50}$ values were very similar to those previously reported by gel-based profiling under slightly different conditions in PC3 cells. To confirm that the inhibitory action observed was specific to NCEH1, the activity of PAFAH2 was monitored in parallel; no inhibition of target signal was observed in response to JW480 (FIG. 5D). These data confirm that ADPL can detect graded changes in enzyme activity in response to both endogenous and exogenous activity modulators. Furthermore, this approach offers a general way to detect and quantify target engagement in live cells, particularly for enzyme targets that are resistant to traditional in vitro approaches, such as post-translationally modified, insoluble enzymes like NCEH1.

Figure 6:
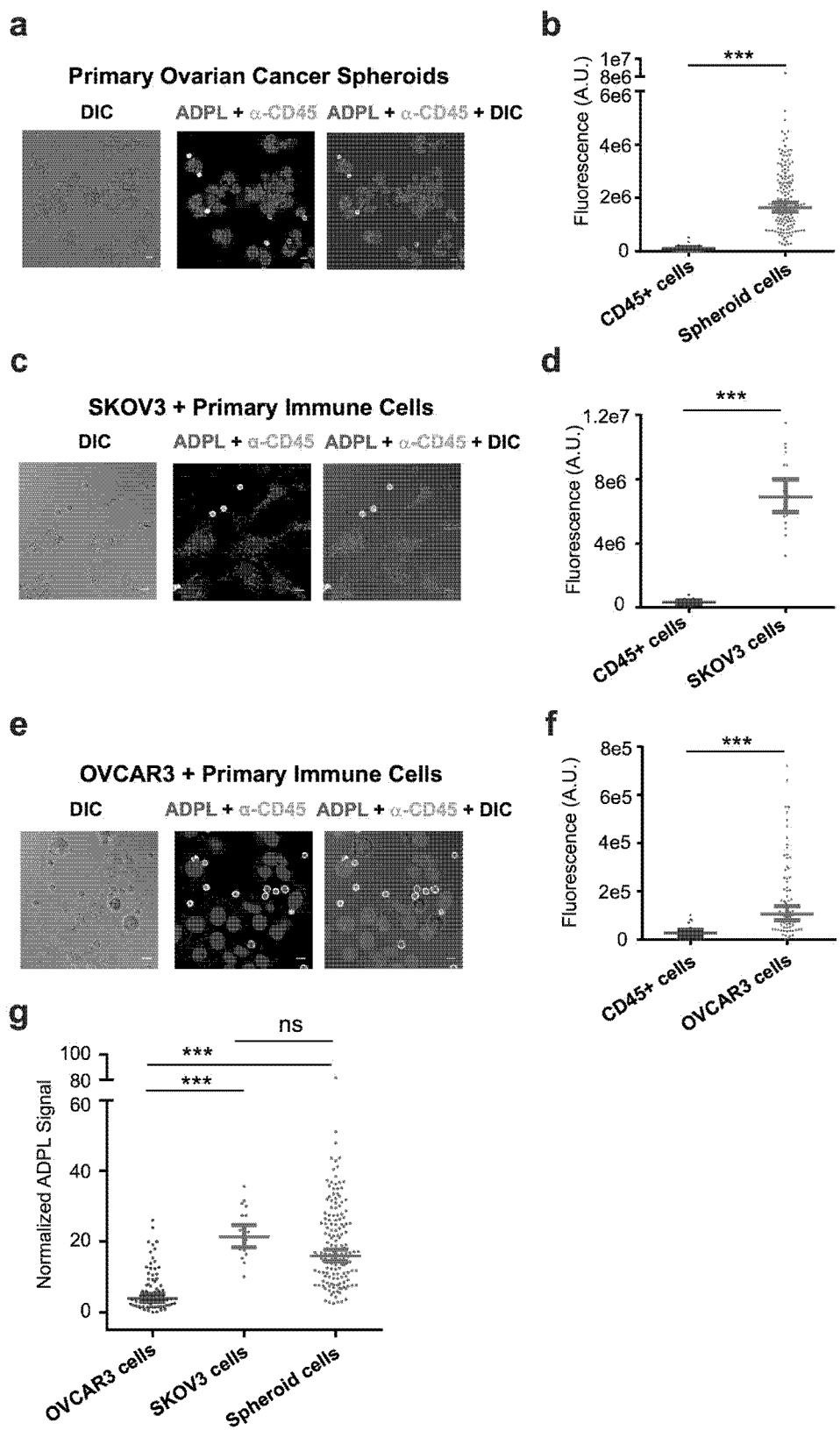
FIG. 6A-G. ADPL quantification of endogenous enzyme activity in cellular co-culture and primary patient samples. (a, b) Representative ADPL images (a) and quantification (b) of NCEH1 activity in primary ovarian cancer spheroids. Simultaneous CD45 staining (green) marks immune cells present in heterogeneous spheroids. Quantification in b: immune cells (n=25), cancer cells (n=155). (c, d) Representative ADPL images (c) and quantification (d) of NCEH1 activity in cellular co-culture of aggressive SKOV3 ovarian cancer cells and primary immune cells. Quantification in d: immune cells (n=16), cancer cells (n=20). (e, f) Representative ADPL images (e) and quantification (f) of NCEH1 activity in cellular co-culture of non-aggressive OVCAR3 ovarian cancer cells and primary immune cells. Quantification in f: immune cells (n=23), cancer cells (n=74) (g) Normalized ADPL signal of OVCAR3, SKOV3, spheroid cancers cells relative to co-cultured CD45+ immune cells (data in b, d, f). Scale bar: 10 μm. Blue channel: DAPI; red channel: ADPL; green channel: CD45; gray channel: DIC. Each point represents a single cell fluorescence measurement, center-line and whiskers denote the mean and 95% C.I. of the population; unpaired student t-test was used for statistical significance. ***, P<0.001; ns, not significant, Student's t-test. Data are from four or more technical replicates from independent duplicate biological experiments.
Figure 11:
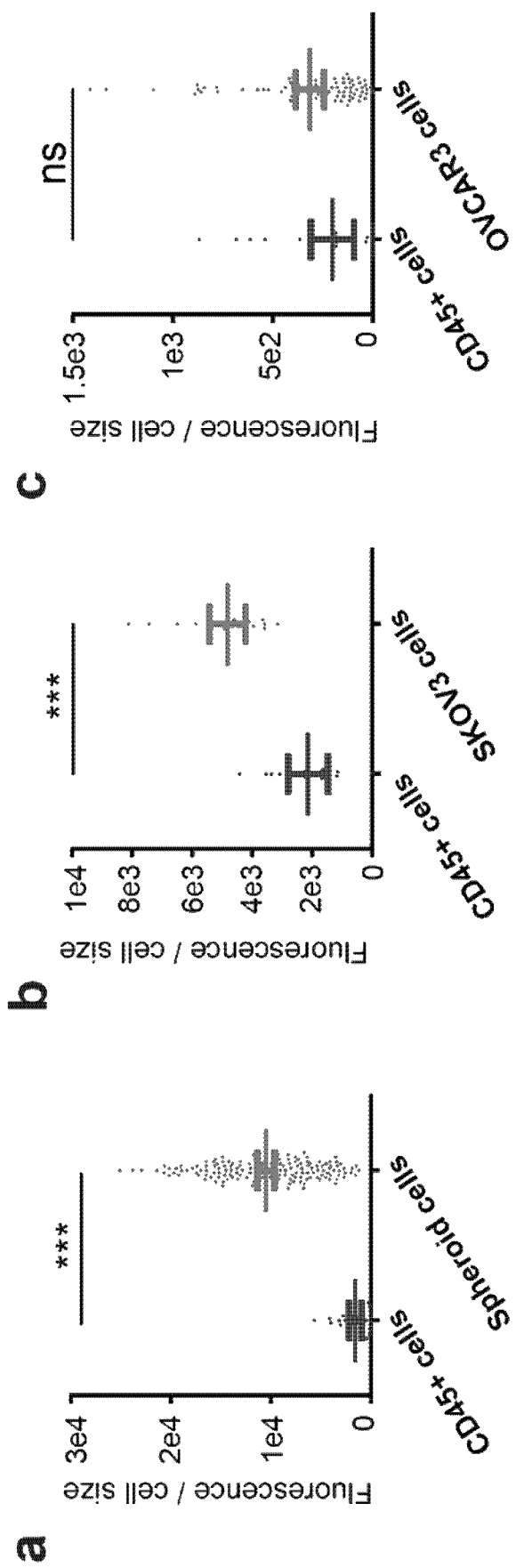
FIG. 11A-C. Area-normalized ADPL quantification of endogenous enzyme activity in cellular co-culture and primary patient samples. (a-c) Cell area-normalized quantification of NCEH1 activity in primary ovarian cancer spheroids (a), SKOV3 ovarian cancer cells (b) and OVCAR3 ovarian cancer cells (c) and primary immune cells. Quantification in a: immune cells (n=25), cancer cells (n=155). Quantification in b: immune cells (n=14), SKOV3 cancer cells (n=20). Quantification in c: immune cells (n=23), OVCAR3 cancer cells (n=74). Each point represents a single cell fluorescence measurement, center-line and whiskers denote the mean and 95% C.I. of the population; unpaired student t-test was used for statistical significance. ***, P<0.001; ns, not significant. Data are from four or more technical replicates from independent duplicate biological experiments.

4. Quantifying Cellular and Phenotypic Heterogeneity in Co-Culture and Primary Patient Tissues One of the challenges with both traditional and activity-based proteomic approaches is determining whether the averaged signal observed by gel or LC-MS/MS-based detection is representative of the population being studied. Due to the retention of cellular structure and reporting of activity from single cells, the inventors hypothesized that ADPL could detect and quantify active enzymes in biologically-relevant, heterogeneous environments such as cellular co-culture. Furthermore, the inventors sought to test whether ADPL could be used to probe enzyme activity in complex primary tissue samples, such as individual patient-derived, ovarian cancer cell spheroids. These organoid tissues are heterogeneous mixtures of cells often detected in ascites, as well as other tumor types. Despite the significance of these organoids in disease, standard mass-spectrometry or gel-based methods cannot be used to study protein abundance or activity due to their small size (~100's of cells). Given the established relationship between NCEH1 activity and ovarian cancer cell aggressiveness, the inventors applied ADPL to detect and quantify active NCEH1 in cellular co-culture and patient-derived spheroids. Image-based ADPL quantification of NCEH1 activity in dissociated individual spheroids revealed that they were not homogeneous and instead consisted of both ovarian cancer cells and CD45+ immune cells (FIG. 6A). NCEH1-dependent ADPL signal was almost entirely localized to the ovarian cancer cells relative to CD45+ cells, quantified as an ~20-fold and ~7-fold increased in raw and area-normalized NCEH1 ADPL activity, respectively (FIG. 6A, B; FIG. 11). To determine if these patient-derived cells were more similar to aggressive or non-aggressive ovarian cancer cell lines, the inventors quantified NCEH1 activity in a co-culture system of CD45+ lymphocyte monocyte immune cells and aggressive SKOV3 or non-aggressive OVCAR3 cancer cells. Consistent with ADPL experiments on these cell lines alone (FIG. 4A), NCEH1 activity was almost exclusively present in the SKOV3 cancer cells, quantified as an ~22-fold increase in NCEH1 activity relative to immune cells (FIG. 6C, D), whereas much less signal were present in both OVCAR3 and its co-cultured immune cells, likewise quantified as a ~6-fold increase relative to immune cells (FIG. 6E, F). Using the immune cells as a standard the inventors generated a ratiometric 'aggressiveness index,' enabling direct comparison of phenotypes in these distinct cellular contexts. These data show significantly increased NCEH1 activity in aggressive SKOV3 and primary ovarian cancer spheroid cells, relative to non-aggressive OVCAR3 cells. These data suggest that the primary ovarian cancer spheroid cells are similar to aggressive, metastatic cells (FIG. 6G), which fits with their annotation as an early stage in ovarian cancer metastasis.

B. Materials and Methods

1. Cell Culture

HeLa, PC3, LNCaP, SKOV3, MCF7 and U87 and OVCAR3 cell lines were obtained from ATCC and were not STR profiled. Cell lines have been tested for *mycoplasma* contamination. HeLa, LNCaP, PC-3, SKOV3, MCF7 and U87 cells were cultured in RPMI 1640 (Hyclone, #SH30027.01) supplemented with 10% fetal bovine serum (FBS, Atlanta Biologicals, #912850) and 1% Penicillin/Streptomycin (Hyclone, #SV30010). OVCAR3 and PC3 cells were cultured in DMEM (Hyclone, #SH30243.01) supplemented with 10% FBS, 1% Penicillin/Streptomycin, 1% MEM nonessential amino acids (Corning, #25-025-CI), and 1% MEM vitamins (Corning, #25-020-CI). All cell lines were grown at 37° C. in a 5% $CO_2$ humidified incubator.

2. Family-Wide Probes a. Fluorophosphonate-Biotin Probe Synthesis

Figure 12:
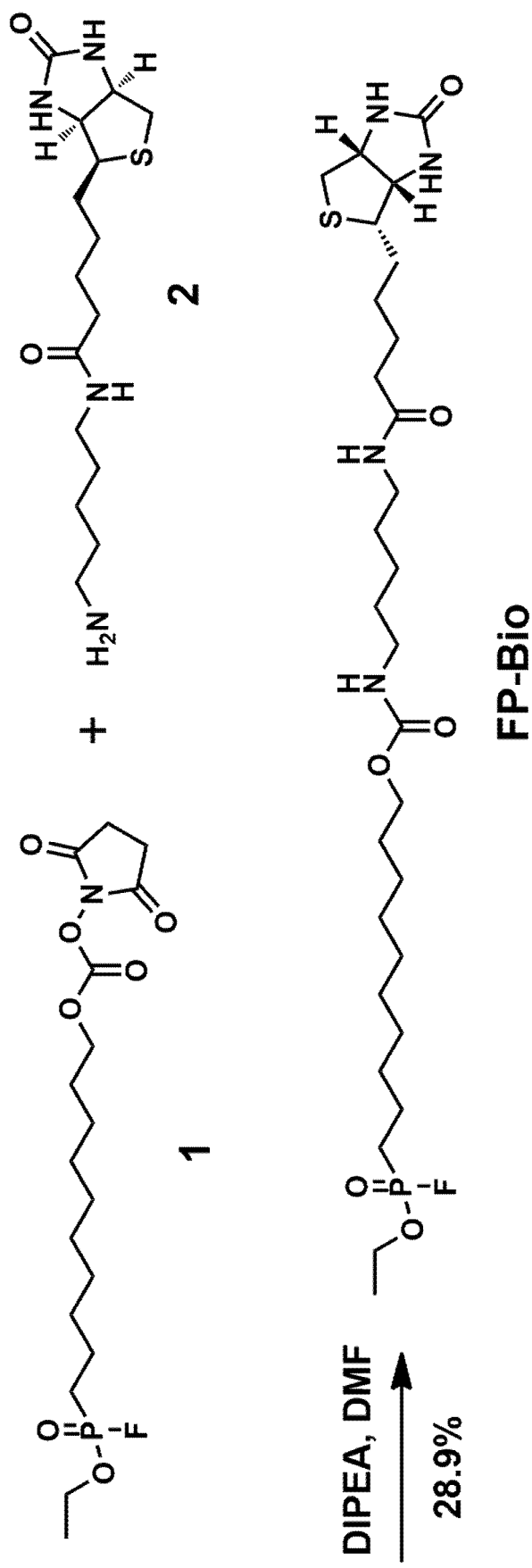
FIG. 12. Fluorophosphonate-biotin (FP-bio) probe synthesis.

To synthesize the probe FP-biotin (FP-Bio), precursors 1 and 2 (FIG. 12) were synthesized according to the previous published procedures (Liu, Y., et al., *Proceedings of the National Academy of Sciences of the United States of America* 96, 14694-14699 (1999) and Tully, S. E. & Cravatt, B. F. *Journal of the American Chemical Society* 132, 3264-3265 (2010)). Precursor 1 (41 mg, 0.1 mmol, 1.0 equivalent) and DIPEA (70 µL, 0.4 mmol, 4.0 equivalent) were dissolved in DMF (0.4 mL, 0.25 M) at the room temperature. Precursor 2 (40 mg, 0.12 mmol, 1.2 equivalent) was then added and the mixture was stirred overnight, concentrated under reduced pressure. The crude material was purified by column chromatography (2% to 12% MeOH/DCM gradient) to give FP-Bio as a white solid. (18 mg, 28.9%). $^1$H NMR (500 MHz, $CDCl_3$) δ 6.16 (s, 2H), 5.35 (s, 1H), 4.90 (s, 1H), 4.52 (dd, J=7.4, 5.1 Hz, 1H), 4.33 (dd, J=7.4, 4.8 Hz, 1H), 4.26 (m, 2H), 4.02 (t, J=6.5 Hz, 2H), 3.23 (dd, J=12.7, 6.6 Hz, 2H), 3.16 (m, 3H), 2.92 (dd, J=12.8, 4.9 Hz, 1H), 2.77-2.71 (m, 1H), 2.21 (t, J=7.2 Hz, 2H), 1.95-1.83 (m, 2H), 1.80-1.25 (m, 31H). $^{13}$C NMR (126 MHz, $CDCl_3$) δ 173.30 (s), 164.19 (s), 156.19 (s), 64.97 (s), 63.17 (d, J=7.3 Hz), 61.91 (s), 60.27 (s), 55.64 (s), 40.66 (s), 39.34 (s), 35.95 (s), 30.43 (s), 30.30 (s), 29.74 (s), 29.50 (s), 29.31 (s), 29.27 (s), 29.15 (d, J=4.9 Hz), 29.03 (s), 28.13 (s, J=7.0 Hz), 25.95 (s), 25.70 (s), 25.07 (s), 24.84 (s), 23.91 (s), 23.69 (s), 21.98 (d, J=5.5 Hz), 16.47 (d, J=5.6 Hz). HRMS (m/z): $[M]^+$ calcd. for C28H52FN4O6PS, 622.3329; found 622.3342.

The cathepsin family-wide probe was obtained from ActivX Biosciences (AX13146).

3. Immunoblotting

Cells were harvested by scraping in PBS, pelleted by centrifugation at 1,000 rpm, washed twice with PBS and lysed in PBS (pH 7.4) containing complete protease inhibitor cocktail (Sigma, #92714-1BTL) by sonication at 4° C. Protein concentration was determined by BCA assay (Pierce, #23225); the cell lysate was diluted into 4× Laemmli buffer (4×: 200 mM Tris pH 6.8, 400 mM DTT, 8% SDS, 0.4% bromophenol, 40% glycerol), followed by heating to 95° C. for 5 minutes, cooling to room temperature, and gel electrophoresis on NuPAGE Novex 4-12% Bis-Tris Protein Gels (Invitrogen, NP0322BOX). PAGE gels were transferred onto nitrocellulose membranes, blocked in 2% BSA in TBS containing 0.1% tween-20 (TBST) and probed with primary and secondary antibodies. Primary antibodies used in this study include: anti-FLAG-M2 (1:2000, F1804, Sigma Aldrich), anti-NCEH1 (in-house mouse polyclonal 1:2000 from 1 mg/mL stock), anti-GAPDH (1:2000, Cell Signaling Technology, #2118S). Blots were imaged using fluorescence-labeled secondary antibodies, IRDye®R-800CW anti-rabbit (LI-COR, #926-32213) or IRDye®M-680RD anti-mouse (LI-COR, #926-68072), on the OdysseyCLxImager (LI-COR). Quantification of band intensities has been performed using ImageJ software (NIH).

4. ESD-NLS and PAFAH2-NLS Plasmid Construction

Full-length, human ESD (NM_001984) and PAFAH2 (NM_000437) in pCMV6 entry vectors with C-terminal Myc-DDK tag were purchased from Origene. The ESD-NLS and PAFAH2-NLS were generated according to a previously published procedure. Briefly, TagMaster mutagenesis kit (GM Biosciences, #GM7002) was employed to introduce a C-terminal SV40 nuclear localization sequence (PKKKRKV) between the existing DDK-tag and stop codon in the pCMV6 entry vector. Mutagenesis was performed according to manufacturer's protocol with the following primers:

Forward: 5'-aaggatgacgacgataagccgaagaagaagcgcaaggtggtttaaacggccggcc-3';

Reverse: 5'-ggccggccgtttaaaccaccttgcgcttcttcttcggcttatcgtcgtcatcctt-3'. The resulting ESD-NLS and PAFAH2-NLS constructs were used for transient transfection experiments in HeLa cells.

5. Transient Transfection $4 \times 10^5$ HeLa cells were seeded in 6-well plate. About 16 hours later, transfection were performed when the cells reached to 60-80% confluency. In terms of the transfection, 200 ng plasmid was added to 60 µL serum free RPMI 1640 medium and 2.5 µL lipofectamine 2000 (Thermo Fisher, #11668027) was added to 60 µL serum free RPMI 1640 medium. The two solutions were incubated at room temperature for 10 minutes. Then, the plasmid was added to the lipofectamine solution and the mixture was incubated at room temperature for 15 minutes, followed by addition of 480 µL serum free medium. The cells were washed with PBS then transfection mixture was added. After 4 hours' transfection, the medium was changed to normal medium. 24 hours later, the cells were trypsinized and seeded into 12-well chamber slide (Ibidi, #81201). ADPL was run according to the protocol below.

6. Immunofluorescence Sample Preparation

Cells were seeded in 12-well chamber slide. 12-24 hours later, when reaching 80-90% confluency, the cells were fixed with 4% paraformaldehyde in PBS at room temperature for 15 min, washed twice with PBS for 5 min each with orbital shaking. Cells were permeabilized in 0.5% Triton X-100 (Fisher) in PBS at room temperature for 15 min, washed twice with 0.05% Tween-20 (Fisher) in PBS for 5 min each at room temperature with orbital shaking. The chamber was removed and the well boundary was delineated with the hydrophobic barrier pen (Vector laboratories, #H-4000). One-drop Duolink blocking buffer (Sigma, #DUO92004)

was added and the slide was incubated at 37° C. for 30 min in a humidified chamber. Anti-FLAG antibody diluted (mouse, 1:100, final concentration 10 µg/ml) was added to the wells and incubated overnight at 4° C. The slide was washed in TBST buffer 3 times for 5 min each. Oregon Green® 488 goat anti-mouse (Invitrogen, #011033, final concentration 10 µg/ml) was added to the wells and incubated 1 hour at 37° C., followed by washing in TBST buffer three times. The slide was mounted in mounting buffer (ProLong Gold, Thermo Fisher Scientific, #P10144) and used for confocal fluorescence microscopy.

7. Lentiviral Expression Vector Cloning

To generate lentiviral vectors for constitutive expression, PAFAH2 and ESD were cloned into the pLenti6 backbone. pLenti-6-TP53-R273H (Addgene, #22934) was digested with BamH1-HF (New England BioLabs, #R3136S) and Age1-HF (New England BioLabs, #R35525) and extracted with phenol-chloroform. Blunt ends were created using DNA Polymerase I, Large (Klenow) Fragment (New England BioLabs, #M0210S), followed by phenol-chloroform extraction. Antarctic Phosphatase (New England BioLabs, #M0289) was used to dephosphorylate the 5' and 3' ends. Following electrophoresis (0.8% agarose), linearized backbone was excised and frozen. DNA was eluted through a polyethylene filter and phenol-chloroform extracted.

PAFAH2 (Origene, #RC200355) and ESD (Origene, #RC200533) constructs were digested using EcoR1-HF (New England BioLabs, #R31015) and Fse1 (New England BioLabs, #R05885), followed by heat inactivation. Blunt ends were created using DNA Polymerase I, Large (Klenow) Fragment (New England BioLabs, #M0210S). Following electrophoresis (0.8% agarose), and the linearized insert excised and frozen. DNA was eluted through a polyethylene filter and phenol-chloroform extracted.

Backbone and insert were ligated using T4 DNA ligase (New England BioLabs, #M0202). NEB 5-alpha Competent *E. coli* (High Efficiency) cells (New England BioLabs, #C2987I) were transformed with the ligated plasmid. Transformed bacteria were plated on LB+Amp (100 µg/ml) agar plates and incubated at 37° C. overnight. Plasmid sequences were verified with Sanger sequencing at the University of Chicago Comprehensive Cancer Center DNA Sequencing Facility using CMV-f and pBABE-r primers. Forward sequencing primer: CMV-f 5'-CGCAAATGGGCGGTAGGCGTG-3.' Reverse sequencing primer: pBABE-r 5'-ACCCTAACTGACACACAT-TCC-3.'

8. Stable Cell Line Generation 293T cells were seeded in 6 cm dishes (BD Biosciences, #353004) at $1.0 \times 10^6$ cells per dish and transfected after 24 hours with transfer plasmid (1 µg PAFAH2 or ESD in pLenti6) and packaging vectors (0.1 µg pCMV-VSV-G, Addgene #8454; 0.9 µg pCMV-dR8.2, Addgene #12263) using Lipofectamine 2000 (Invitrogen #11668027). Following overnight transfection, media was exchanged and allowed to incubate for an additional 24 hours. Viral collection was performed at 24, 48 and 72 hours. Viral media was filtered with a Millex®-AA 0.8 µm filter (Fisher Scientific #SLAAV255F) and Polybrene (Sigma #H9268) was added to a concentration of 8 µg/mL before infection of target cell lines. SKOV3 and PC-3 cell lines were infected with 48-hour viral harvest. After 24 hours, cells were allowed to recover by exchanging the media. Cells were selected with Blasticidin (Fisher Scientific #20-335-025MG) at 5 µg/mL for the first three passages as a lower stringency selection. Then, 20 µg/mL was employed as a higher stringency for the following three passages.

9. Gel-Based Activity Profiling

Cells were grown in 6-well plates or 6-cm dishes until reaching 80-90% confluence. FP-biotin (FP-Bio, 10 mM stock in DMSO) was diluted to 2 µM in DMEM, and added to cells at 37° C. for 40 minutes. Cells were then washed in PBS, scraped and lysed by sonication using PBS buffer supplemented with protease inhibitor cocktail (Sigma, #92714-1BTL). Protein concentration was determined by BCA assay (Pierce, #23225), lysate was diluted in Laemmli buffer (4×: 200 mM Tris pH 6.8, 400 mM DTT, 8% SDS, 0.4% bromophenol, 40% glycerol), heated to 95° C. for 5 minutes, and resolved on a 4-12% PAGE gel (ThermoFisher, NP0322BOX). PAGE gels were processed for Western blot as indicated above with IR800-conjugated streptavidin (LI-COR, #926-32230) overnight at 4° C. Images were captured by Odyssey CLx imaging system (LI-COR). Quantification of band intensities was performed using ImageJ software (NIH).

10. Activity-Based Proximity Ligation (ADPL)

Cells were seeded in the 12-well chamber slide, typically at 10,000-30,000 cells per well (Ibidi, #81201). To get an even distribution of the cells, the chamber slide was pre-wetted with cell culture medium, drained off, and the chamber was left at room temperature for 5-10 min after seeding. Cells at 80-90% confluency were pulse treated with either FP-Bio (2 µM) in DMEM and incubated at 37° C. for 40 min or Capthepsin probe (5 µM) in complete medium and incubated at 37° C. for 3 hr. Cells were washed with PBS, fixed with 4% paraformaldehyde in PBS at room temperature for 15 minutes, washed twice with PBS for 5 minutes each at room temperature with orbital shaking and then permeabilized in 0.5% Triton X-100 in PBS at room temperature for 15 minutes. Finally, cells were washed twice with 0.05% Tween-20 in PBS for 5 minutes each at room temperature with orbital shaking.

Prior to antibody incubation, the chamber was removed and the well boundaries delineated with the hydrophobic barrier pen (Vector laboratories, #H-4000). One-drop Duo-link blocking buffer (Sigma, #DUO92004) was added and the slide was incubated at 37° C. for 30 minutes in a humidified chamber. The blocking solution was removed by tapping, followed by addition of 10 µg/ml of the anti-biotin (rabbit, Abcam, #G196266) and primary antibody for the protein of interest: anti-FLAG (mouse, 4 µg/ml of Sigma, #F1804-5 mg); anti-NCEH1 (mouse, 4 µg/ml of in-house polyclonal), anti-FAAH (mouse, 4 µg/ml of Abcam, #ab54615) for serine hydrolase members. For the cathepsin B, 20 µg/ml of the anti-biotin (rabbit, Abcam, #G196266) and 10 µg/ml of the anti-cathepsin B (mouse from Abcam, #ab58802) were added following the blocking step. Generally, a 20 uL solution of the two primary antibodies per well was incubated at 4° C. overnight with orbital shaking. Primary antibodies solution was removed by tapping; the slide was washed in wash buffer A (150 mM NaCl, 10 mM Tris, 0.05% Tween 20, pH 7.3) three times for 5 minutes with gentle orbital shaking. Oligo-linked secondary antibodies were then diluted 5-fold in antibody diluent buffer (Duolink anti-mouse minus and anti-rabbit plus from Sigma; #DUO92004 and #DUO92002), added to the slide and incubated at 37° C. for 1 hour with orbital shaking.

The secondary antibody-probe solution was removed by tapping the slide, followed by washing in buffer A three times with gentle orbital shaking. Ligation mixture (Sigma, Duolink In Situ Detection Reagents Orange kit, #DUO92007) was diluted five-fold in water prior to addition of ligase at a 40-fold dilution. The ligation mixture was incubated at 37° C. for 30 minutes with orbital shaking, removed, and the slide was washed twice. Finally, amplification solution was diluted 5-fold in water prior to addition of polymerase at 80-fold dilution. This amplification solution was added to each well, incubated at 37° C. for 90 minutes in the dark, and removed by washing with buffer B (0.1 M NaCl, 0.2 M Tris, pH 7.3) twice for 10 minutes each, followed by wash with 100-fold dilution of wash buffer B for 1 minute. Slides were dried at room temperature in the dark, mounted with 50 μL anti-fade mounting solution (Life technology, #P36961), covered with the cover glass (Fisher, #12-545M), and sealed with nail polish.

For the characterization of the location of cathepsin B in U87 cells, the above ADPL procedure was followed until the amplification step. After wash with buffer B twice for 10 minutes each, the slides were incubated with either Oregon Green® 488 goat anti-mouse (Invitrogen, #011033, final concentration 10 μg/ml) at 4° C. overnight for immunofluorescence, or Alexa Fluor® 647 anti-human LAMP1 Antibody (BD, #522622, 5 fold dilution) at 4° C. overnight for co-localization study. Then the slide was washed with buffer A twice for 5 minutes each, followed by washing with 100-fold dilution of PBS for 1 minutes. Slides were sealed following the procedure above.

11. Confocal Fluorescence Microscopy Imaging

Leica SP8 Laser Scanning Confocal was used to image a single focal plane to accurately detect the ADPL signal location using HyD detectors. An Olympus "live cell" DSU Spinning Disk Confocal microscope was employed to get the integrated z-stack images to accurately quantify the ADPL signal intensity in FIG. 5A. Identical microscope acquisition parameters were set and used within experiments. Post-acquisition processing was performed using ImageJ software (NIH).

12. ADPL Image Processing and Quantification

ImageJ was used to process all images. Lossless TIFF files were employed to quantify fluorescence intensity. To simplify the image processing workflow a Macro script to automatically process all images was created. The workflow was as follows: open all channels for each field of view; designate a color for each channel; adjust brightness/contrast for all channels (applying the same levels for all conditions within and between experiments to allow for direct comparison); merge the channels together; adjust the image unit from pixel to micrometer; add scale bars; export the processed TIFF files for quantification.

For quantitative analysis single cell boundaries were identified manually using the DIC image. Then the "ROI Manager" tool in Image) was utilized to add all the cell outlines as a collection and overlay with the ADPL channel to measure per-cell fluorescence intensity. Typical quantitative comparisons were made using data from three or more independent fields of view per independent biological replicate condition.

13. Inhibitor Profiling by ADPL

Confluent (80-90%) PC3 cells or PAFAH2 expressing PC3 cells were treated with indicated final concentrations of JW480 (0 nM, 1 nM, 10 nM, 100 nM, 1 μM) in complete cell culture medium for four hours at 37° C., prior to FP-Bio probe (2 μM) labeling at 37° C. for 40 minutes in serum free medium. ADPL workflow was followed as indicated above. Normalized ADPL signal based on no JW480 treatment was created. $IC_{50}$ curves for NCEH1 were generated in Graphpad Prism 6 using the non-linear regression and dose-response inhibition and the connecting curve for PAFAH2 was generated simultaneously.

14. ADPL Imaging of Ovarian Cancer Spheroids and Co-Culture

Ovarian cancer spheroid cells were isolated from the ascites of patients undergoing primary tumor debulking at the University of Chicago Comprehensive Cancer Center with informed consent and with University of Chicago Institutional Review Board approval. Ascites fluid was centrifuged at 3000 rcf for 5 minutes and resuspended in PBS. Spheroids were collected by passing spheroid suspension through 40 μm nylon mesh (Fisher Scientific, 22363547) and washed thoroughly with PBS. Enriched spheroids were collected from the top of the filter in DMEM growth media and transferred to ultra-low attachment plates (Corning 07-200-601) until seeding. Before seeding the cells, the chamber slide was pre-coated with fibronectin (1:50 from 1 mg/mL stock) for 30 minutes at room temperature. As a heterogeneous mixture of cells, spheroids cells were seeded directly without cell counting. 2-fold and 4-fold dilutions were tried simultaneously for proper confluency at the point of probe treatment. Then, typical ADPL procedure was performed through the rolling circle amplification and detection step. After the slide was washed in wash buffer B, the slide was washed in TBST three times for 5 minutes and blocked again for 30 minutes at 37° C. The anti CD45-FITC (BD Biosciences, #555482; 1:50 dilution) was added to the wells and incubated overnight at 4° C. The slide was then washed in TBST three times for 5 minutes and dried at room temperature in the dark, mounted with 50 μL anti-fade mounting solution, covered with cover glass, and sealed with nail polish.

15. Co-Culture of SKOV3, OVCAR3 and Immune Cells

Peripheral blood was collected from patients with informed consent (IRB 13372) into purple-cap vacutainers ($K_2$EDTA; BD Biosciences, 367861) and peripheral blood mononuclear cells isolated with Ficoll-Paque PLUS (GE Healthcare, 17-1440-02) using manufacturer's recommended protocol. Before seeding the cells, the chamber slide was pre-coated with fibronectin (1:50 from 1 mg/mL stock) for 30 minutes at room temperature. Then 8,000 SKOV3 and 40,000 $CD45^+$ immune cells, or 30,000 OVCAR3 and 10,000 immune cells were seeded in the chamber slide. The same procedure as spheroid cells was adopted in the following steps.

Statistics Statements.

All experiments consisted of at least three independent replicates, with biological or technical replicates indicated. All center values given refer the mean and error bars shown represent the standard error of the mean, unless otherwise stated. Sigmoidal binding curves were applied using Prism software and affinities or $IC_{50}$ values reported represent the mean and the 95% confidence interval. Asterisks in figure legends refer to P-value thresholds of <0.05 (*), <0.01 () or <0.005 (*) from two-sided Student's t-tests. No statistical methods or power calculations were used to determine sample size, however these were kept constant between groups whenever possible.

Example 2: A Concise, Modular Antibody-Oligonucleotide Conjugation Strategy Based on Disuccinimidyl Ester Activation Chemistry Synthesis of antibody-oligonucleotide conjugates has enabled the development of highly sensitive bioassays for specific epitopes in the laboratory and clinic. Most synthetic schemes to generate these hybrid molecules require expensive reagents, significant quantities of input antibody, and multi-step purification routes, thus limiting widespread application. Here the inventors report a facile and robust conjugation strategy that involves "plug-and-play" antibody conjugation with succinimidyl-functionalized oligonucleotides, which are high-yielding and compatible for use directly after buffer exchange. The succinimidyl-linked oligonucleotides are synthesized with 5'-amine-modified oligonucleotides and disuccinimidyl suberate (DSS), both of which are inexpensive and commercially available. Direct incubation of the resulting stable succinimidyl-oligonucleotide conjugates with commercial antibodies yields conjugates ready for use after benchtop buffer exchange. Here the inventors demonstrate that the resulting oligonucleotide-antibody and oligonucleotide-streptavidin conjugates retain potent and specific binding in activity-dependent proximity ligation imaging, and proximity ligation-mediated qPCR detection of endogenous proteins in native cellular contexts down to picorgram levels of whole proteome. This DSS conjugation strategy should be widely applicable in the synthesis of protein-oligonucleotide conjugates.

A. Results and Discussion

Figure 15:
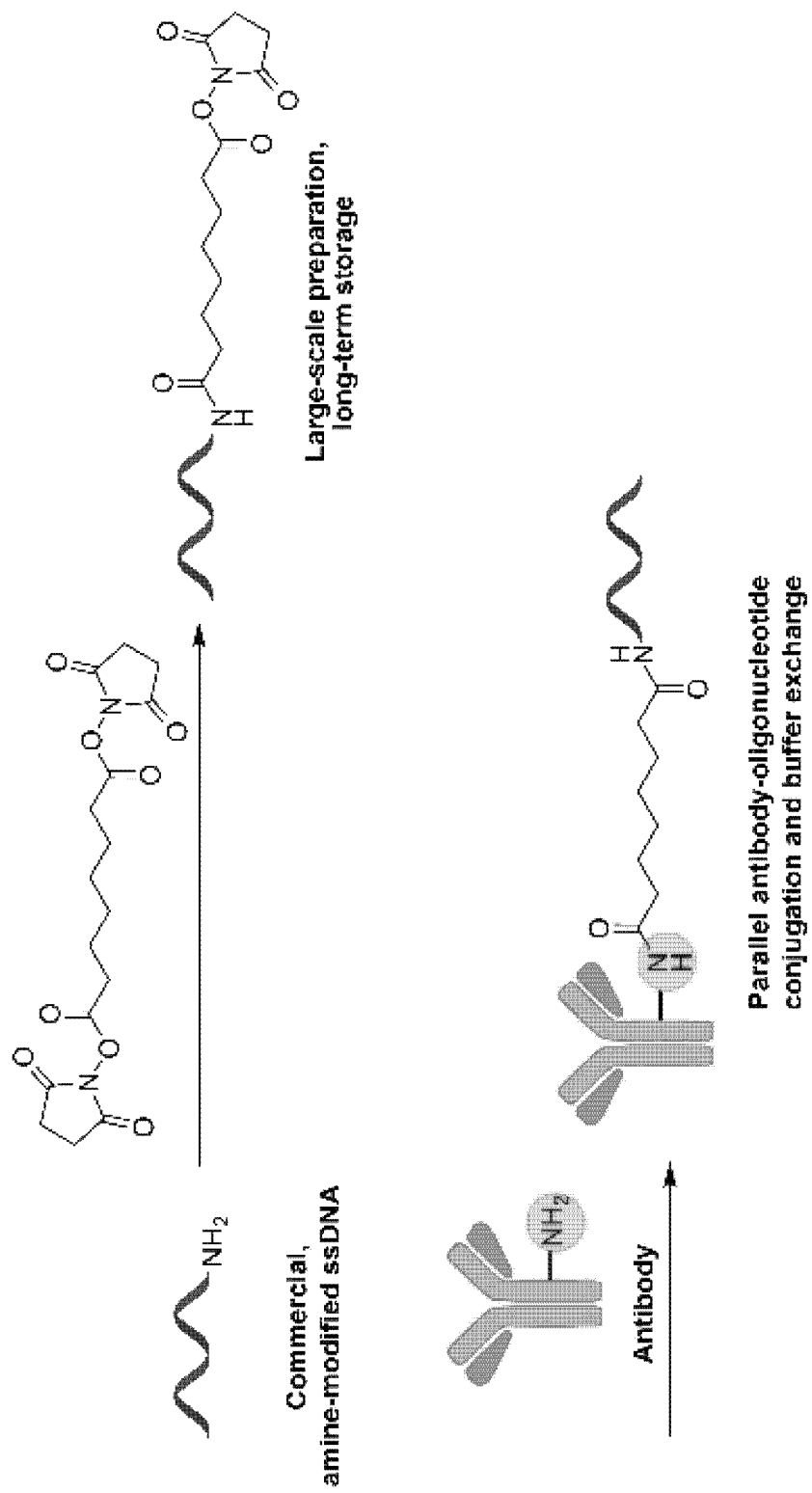
FIG. 15 depicts general DSS conjugation reaction schematic. Disuccinimidyl ester modification of amine-modified ssDNA, followed by parallel reaction with commercial antibodies yields stable antibody-oligonucleotide conjugates after benchtop sample buffer exchange.

In this design, commercially available and affordable amino-containing single-stranded DNA (ssDNA) is reacted with an excess of the homobifunctional linker disuccinimidyl suberate (DSS), and purified by high performance liquid chromatography (HPLC). The resulting activated-oligonucleotides can be stably aliquoted and stored under acidic conditions for months prior to direct introduction to antibody conjugation reactions (FIG. 15). To test this approach, a model 5'-amine modified, single-stranded 60-mer ssDNA was reacted with an excess of DSS linker at room temperature for 30 minutes, followed by ethanol precipitation and reverse phase HPLC purification. The hydrophobic nature of the succinimidyl suberate linker results in consistent chromatographic separation of the product from the starting material and side products (FIG. 16A). Modification yields above 50% were consistently observed, and the purified succinimidyl-modified ssDNA products could be lyophilized under acidic conditions (0.1% TFA), aliquoted and stably stored for several months, as confirmed by MALDI-TOF. In particular, the absence of hydrolysis product confirmed the stability of the activated oligonucleotide. Using this DSS labeling scheme, a single round of synthesis and HPLC purification yielded sufficient succinimidyl-modified ssDNA for ~20 conjugations with 10 µg antibody samples that represent the lower limit of input antibody currently employed in other conjugation routes.

To test the antibody-oligonucleotide conjugation reaction, 3-4 equivalents of succinimidyl-modified ssDNA was added to ~10 µg of antibody (0.3-1 mg/mL in PBS) in 0.25 M HEPES, 0.25 M NaCl (pH 7.4) buffer. Reactions were run overnight at room temperature, quenched with 1.0 M TRIS buffer (pH 7.5), and unreacted and hydrolyzed oligonucleotide was removed by passage through a centrifugal filter. Reducing SDS-PAGE gel analysis of conjugation reactions with three commercial antibodies (anti-CTSB, anti-Myc, and anti-FAAH) confirmed the appearance of higher molecular weight conjugates primarily consistent with heavy chain and light chain monomers attached to a single oligonucleotide (FIG. 16B). Notably, the presence of bovine serum albumin (BSA), a common additive to commercial antibody stocks, did not influence the conjugation reaction or the resulting activity of conjugates (vide infra). Close inspection of the antibody-conjugates by non-denaturing PAGE gel electrophoresis revealed a degree of conjugation (DoC) is series of between one and three ssDNAs, with a single ssDNA conjugate being the most abundant species for all antibodies tested (FIG. 16C). These results were confirmed by MALD-TOF detection of the mono-substituted, full length ssDNA-antibody conjugate). Conjugation yields for the three representative commercial antibodies were 85.7, 82.8 and 79.1% for anti-CTSB, anti-Myc, and anti-FAAH, respectively. Together with functional validation of antibody activity after oligo-conjugation, these data establish that DSS chemistry is a highly efficient, modular strategy for constructing antibody-oligonucleotide conjugates.

The inventors next sought to validate the activity and potential applications of ssDNA-antibody conjugates synthesized with this modular DSS ligation strategy. The inventors recently reported an activity-dependent proximity ligation (ADPL) platform for the spatially-resolved, quantitative imaging of active enzymes in single cells. This method involves treating live cells with a biotinylated, family-wide activity-based probe targeting an enzyme family of interest, followed by cell fixation. Fixed cells are then labeled with probe-specific and protein-of-interest (POI)-specific primary antibodies, followed by secondary antibodies conjugated to barcoded, single-stranded oligonucleotides (FIG. 17A). Coincidence of the probe- and protein-directed dual antibody complexes enables specific ligation of a bridging oligonucleotide and rolling circle amplification. Finally, ADPL signal is detected by incubation with a complementary, fluorophore-labeled oligonucleotide and fluorescence microscopy. It was speculated that a potential liability of the dual primary-secondary antibody "sandwich" complex, which could theoretically extend up to ~40 nm from either the probe or POI, may result in background signal generated from complexes formed on the POI and endogenous biotinylated proteins or other non-POI targets of the probe. Based on this assumption, the inventors sought to shorten the distance between the protein epitope and the probe recognition element (i.e. biotin) by installing the oligonucleotide barcode directly to the primary antibody-of-interest. For chemical probe recognition and labeling, the inventors sought to replace the α-biotin antibody with a streptavidin-ssDNA conjugate, which would take advantage of its smaller size and higher binding affinity to biotin. To compare the performance of the dual sandwich complex and direct ssDNA-Ab conjugates side-by-side the inventors synthesized a barcoded ssDNA conjugate on polyclonal antibodies directed at the serine hydrolase enzyme neutral cholesterol ester hydrolase 1 (NCEH1), as well as a non-antibody protein, streptavidin, for chemical probe recognition. The inventors compared NCEH1 activity in aggressive ovarian cancer cell line SKOV3 with the established dual antibody sandwich complex (FIG. 17B-C), as well as the direct anti-NCEH1-oligonucleotide and streptavidin-oligonucleotide conjugates. Consistent with previous findings, the dual sandwich structure has a relatively high amount of background signal, as indicated by a probe/no-probe fluorescence ratio of 3.2-fold (FIG. 17C). In contrast, ADPL quantification of NCEH1 activity with DSS-synthesized direct oligonucleotide conjugates had significantly lower background signal in the no probe control, marked by a probe/no-probe ratio of 9.0 (FIG. 17D-F). Similar with previous result, the inventors found omission of any component or step in the protocol resulted in significant loss of signal. The inventors note that signal with probe treatment obtained using the DSS synthesized direct oligonucleotide conjugates was lower compared to the signal obtained by dual sandwich complex, which is expected due to the lack of signal amplification caused by multivalent secondary antibodies binding to primary antibody.

To determine whether protein levels alone could be quantified with direct ssDNA-antibody conjugates generated by DSS chemistry, the inventors tested the conjugates by solution-phase PLA-qPCR targeting the glycolytic enzyme GAPDH. This ultrasensitive quantification method requires the binding of two antibodies to distinct epitopes on the same protein molecule, thus templating proximity-based hybridization of unique barcoded oligonucleotides with splint oligonucleotide (FIG. 18A), which is unable to form at the extremely dilute concentrations in free solution. Using DSS chemistry the inventors synthesized three anti-GAPDH-oligonucleotide conjugates to test two different PLA-qPCR quantification formats directly in whole proteome from PC3 prostate cancer cells. First, the inventors separately labeled a polyclonal antibody mixture with two complementary barcoded antibodies (poly1+poly2). Consistent with previous literature reports, because polyclonal antibodies can bind an array of sites on the target protein the combined mixture can detect proximity of both bound oligonucleotides and template subsequent hybridization, ligation and amplification. The inventors also separately labeled the polyclonal antibody with one oligonucleotide and separately labeled a monoclonal antibody species raised against a unique epitope with a second complementary ssDNA (mono1+poly2), which similarly should be able to template a proximity-dependent ligation on a single target molecule. Using these two sets of barcoded antibodies the inventors performed GAPDH-directed PLA in whole lysate from PC3 cells, which led to specific and robust qPCR signal when all PLA reagents were included (FIG. 18B). Specificity of PLA detection was highlighted by >200-fold increases in signal between measurements made in cell lysate with the full complement of assay reagents compared to several mock conditions; these results were consistent for both poly1+poly2 and mono1+poly2 antibody pairs (FIG. 18B). PLA-qPCR measurements across a dilution series of whole proteome demonstrated high linearity across several orders of magnitude (FIG. 18C), and limit-of-detection (LOD) values down to pg levels of whole proteome for both antibody pairs (FIG. 18D). Notably, PLA detection of endogenous proteins in native cellular contexts represents a greater challenge than detection of purified or recombinant proteins. In terms of dynamic range and limit-of-detection, this DSS strategy is on par with published method. These results validate that antibody-oligonucleotide conjugates synthesized by DSS chemistry retain activity and can be used for ultrasensitive detection and quantification of protein abundance or activity from native proteome.

B. Conclusions

Recently, many methods have been developed for preparing covalent antibody conjugates, especially in the field of antibody-drug conjugates (ADCs), which have been used successfully as cancer therapeutics. Given the high demand for convenient strategies with a low technical barrier of entry, heterobifunctional cross-linker chemistries have been widely utilized. In this report, the inventors developed homobifunctional DSS chemistry for facile plug-and-play synthesis of antibody-oligonucleotide conjugates. Previous reports have also shown that succinimidyl-modified ssDNAs can be used in the specific cases of metal-binding or epitope-tagged proteins through the use of a template DNA strand to bring the reactive ssDNA into specific proximity on the protein. Likewise, commercial kits are available using DSS conjugation chemistry that involve pre-activation of the protein with DSS, which generates a tethered succinimidyl group directly on the antibody surface, leading to inter- and intra-protein crosslinks, lower yield and reduced activity. In contrasts to these approaches, the data herein demonstrate that direct labeling with succinimidyl-ssDNAs can be applied generally to diverse natural proteins like antibodies and streptavidin, without requirements for DNA-templated guides, while still generating specific affinity reagents that avoid unwanted background reactions. DSS conjugation has the advantages of streamlined procedures, high conjugation yield, low sample loss, and minimal perturbation to antibody function. Additionally, comparison to conjugation strategies using other heterobifunctional cross-linkers (e.g. SMCC, SANH and DBCO) with respect to oligonucleotide price, conjugation steps, purification method, and minimum antibody requirements highlights several advantages for the DSS conjugation strategy (Table 1). In terms of the oligonucleotide price, DSS chemistry only requires an amine-modified ssDNA, which is ~10-fold cheaper than thiol-modified oligonucleotides and ~100-fold cheaper than azide-modified oligonucleotides. Likewise, the disuccinimidyl linker itself is considerably cheaper than bifunctional linkers for Michael addition-like conjugations (e.g. SMCC) or click chemistry (e.g. DBCO). DSS chemistry only requires one step—DSS modification of target ssDNA—prior to direct conjugation to commercial antibodies. This one-step preparation can be performed in a parallel fashion, and the resulting succinimidyl-ssDNA species is stable for long-term storage and sufficient for many downstream parallel labeling reactions to generate, for example, multiplexed barcoded antibody libraries. Finally, the average labeling yield for DSS chemistry is in excess of 80%, which allows omission of FPLC or magnetic bead purification, labeling of small amounts of input antibody (~10 µg tested here), which greatly reduces the waste of precious antibodies. It is anticipated that DSS chemistry will serve as a useful synthetic strategy for the preparation of antibody or other protein-oligonucleotide conjugates in a range of applications.

TABLE 1

Comparison of DSS to SMCC, SANH, and click chemistry.

| Method | Oligo Price [a] | Additional Reagent(s) Price | Typical Conjugation Procedure | Minimum Ab amount |
|---|---|---|---|---|
| DSS chemistry | amine-modified ssDNA: ~$10/100 nmol | DSS: $9.7/ 100 mg [b] | 1) ssDNA-amine reaction with DSS; HPLC purification and storage 2) Parallel reaction of succinimidyl-ssDNA with antibody; buffer exchange | ~10 µg |

TABLE 1-continued

Comparison of DSS to SMCC, SANH, and click chemistry.

| Method | Oligo Price [a] | Additional Reagent(s) Price | Typical Conjugation Procedure | Minimum Ab amount |
|---|---|---|---|---|
| SMCC chemistry | Thio-modified ssDNA: ~$130/100 nmol | sSMCC: $491.6/100 mg [b] | 1) Reaction of sSMCC with antibody; desalt<br>2) Reduce the ssDNA-thiol with DTT; desalt<br>3) Reaction of sSMCC-modified antibody with ssDNA-thiol;<br>4) FPLC purification and concentrate for use | ~100 μg |
| SAHN chemistry | amine-modified ssDNA: ~$10/100 nmol | All-in-one conjugation Kit [c]: $546.0/100 μg Ab | 1) Reaction of ssDNA-amine with sulf-S-4FB; desalt<br>2) Reaction of S-HyNic with antibody; desalt<br>3) Reaction of modified ssDNA and antibody with aniline catalyst<br>4) Magnetic-affinity, solid phase purification & elution | ~100 μg |
| Click chemistry | azide-oligo: ~$1270/100 nmol | DBCO—PEG4—NHS ester: $523.2/100 mg | 1) Reaction of DBCO—PEG4—NHS ester with antibody; desalt<br>2) Reacton of ssDNA-azide with DBCO-antibody; buffer exchange | ~10 μg |

[a] representative prices from oligo vendor IDT.
[b] prices from Thermo Fisher.
[c] price from TriLink Biotechnologies.

C. Materials and Methods.

All chemicals were purchased from Sigma-Aldrich unless noted otherwise and were used as received. The amine modified single strand oligonucleotides were purchased from Integrated DNA Technologies (IDT); detailed sequences are listed in supplementary Table 1, 2. Commercial antibodies were purchased from Abcam (#ab58802, anti-cathepsin B), Millipore Sigma (#05-724, anti-Myc tag), Abcam (#ab54615, anti-FAAH1), respectively. Polyclonal anti-NCEH1 antibody was prepared in house by antigen immunization. Duolink PLA probes (#DUO92004 and #DUO92002) and Duolink PLA detection reagents (#DUO92007) were purchased from Sigma-Aldrich. NuPAGE Novex 4-12% Bis-Tris protein gels were purchased from Thermo Fisher Scientific (#NP0322BOX). Sybr-gold nucleic acid gel stain solution was purchased from Thermo Fisher Scientific (#S11494). Streptavidin was purchased from Leinco Technoligies, Inc (#S203). IgG was purchase from Thermo Scientific (#02-6202). Absorption measurement were recorded on a Thermo Scientific Nanodrop 2000 spectrophotometer. 12-well chamber slide was purchased from Ibide (#81201). HPLC for oligonucleotide modification purification was performed using a Waters e2695 Separations Module. FPLC for streptavidin-oligonucleotide conjugate was performed using a AKTAexplorer with HiTrap Q HP column. Leica SP8 Laser Scanning Confocal was used to image a single focal plane to accurately detect the ADPL signal location using HyD detectors. Identical microscope acquisition parameters were set and used within experiments. Post-acquisition processing was performed using ImageJ software (NIH).

1. Activated NHS Ester Modified Oligonucleotides Preparation.

5' or 3' amine modified oligonucleotide was dissolved in water (20 nmol, 75 μL). DSS linker was dissolved in DMF (50 mM), then 75 μL of the DSS solution was added to oligonucleotide solution together with 75 μL of acetonitrile and 1 μL of triethylamine. The mixture was shaken at room temperature for 30 minutes, followed by ethanol precipitation. Briefly, 28 μL of sodium acetate (3 M, pH 5.2), 565 μL of pure ethanol and 2 μL of glycogen (20 mg/ml) were added to the mixture. After thorough vortexing, the mixture was kept in −80° C. for one hour, followed by centrifugation at 14,000 rpm for 30 minutes. The pellet was recovery by removing the supernatant, reconstituted in 0.03 M acetic acid (pH 4.5), and filtered through 0.2 μm filter. Reverse phase HPLC (phase A: 0.05 M trimethylamine/acetic acid buffer, pH 7.0; phase B: acetonitrile) was employed to purify the mixture. The HPLC gradient was 0-20% of phase B in 35 minutes. The peak of product fraction was collected and equal volume of 0.2% trifluoroacetic acid solution was added to stabilize the activated NHS ester product. Then the modified oligonucleotide was aliquoted and lyophilized. The concentration was quantified based on the absorbance at 260 nm by Nanodrop.

2. Succinimidyl-Modified ssDNA MALDI-TOF Characterization.

50 mg/mL 3-HPA was dissolve in water and acetonitrile (1:1). 50 mg/mL ammonium citrate was dissolve in water. Then mix 3-HPA solution with ammonium citrate solution (9:1) to act as the matrix. ~100 pmol of succinimidyl-modified ssDNA (1 μL) was spot together with matrix (1 μL). The oligonucleotides were characterized by Bruker ultraflextreme MALDI-TOF.

3. Antibody-Oligonucleotide Conjugate Preparation.

The antibody was dialyzed against PBS at 4° C. overnight, then concentrated using a 50 kD centrifugal filter tube. The concentration of the antibody was quantified based on absorbance at 280 nm. The typical concentration should be within 0.3-1.0 mg/ml. Lyophilized oligonucleotide (200 pmol, 3 equivalents) was dissolved in 4 μL of 1.0 M HEPES plus 1.0 M NaCl buffer (pH 7.4) and mixed with antibody (10 μg in PBS) and stirred at room temperature overnight. After quenching the reaction with 1 μL 1.0 M Tris (pH 7.5), excess oligonucleotide was removed by 50 kD centrifugal filter tube 6× for 10 minutes each. Antibody-oligonucleotide concentration was quantified by microBCA assay (Thermo Fisher Scientific, #23235) and the labeling conjugate was validated by native and denature PAGE gels. The gels were stained with Sybr-gold stain solution for 30 minutes at room temperature and briefly washed with water. The gel images were captured in a Chemidoc imaging system and the labeling yield was quantified by densitometry in ImageJ.

4. Antibody-Oligonucleotide Conjugates Characterization.

The DNA-modified antibody or IgG (~1 mg/ml) was desalted using Zeba spin columns (7000 MWCO). A matrix solution was prepared by dissolving sinapinic acid (1 mg) in acetonitrile (70 µL) and water with 0.1% trifluoroacetic acid (30 µL). 1 µl of the DNA-antibody solution was deposited onto the MALDI plate and then mixed with 1 µL of MALDI matrix. The plate was allowed to dry at room temperature for ~4-5 hours. The oligonucleotides-antibody conjugates were characterized by Bruker ultraflextreme MALDI-TOF.

5. Streptavidin-Oligonucleotide Conjugate Preparation.

DSS modified oligonucleotide (960 pmol, 0.5 equivalent) was dissolved in 20 µL 0.03M acetic acid (pH 4.5). Streptavidin (100 in 30 µL PBS) was added to the oligonucleotide solution together with 15 µL of 1.0 M HEPES plus 1.0 M NaCl buffer (pH 7.4). The mixture was stirred at room temperature overnight. After quenching the reaction with 1 µL 1.0 M Tris (pH 7.5), the mixture was purified by ion exchange fast protein liquid chromatography (FPLC) in an AKTAexplorer with HiTrap Q HP (1 ml) column (Fig. S8 for FPLC chromatogram).

6. Activity-Based Proximity Ligation (ADPL) with "Sandwich Probe Structure".

PC3 cells were seeded in the 12-well chamber slide at 30,000 cells per well. Cells at 80-90% confluency were pulse treated with serine hydrolase family-wide inhibitor FP-Bio (2 µM) in RPMI1640 medium and incubated at 37° C. for 40 minutes. Cells were washed with PBS, fixed with 4% paraformaldehyde in PBS at room temperature for 15 minutes, washed twice with PBS for 5 minutes each at room temperature with orbital shaking, then permeabilized in 0.5% Triton X-100 in PBS at room temperature for 15 minutes, and washed twice with 0.05% Tween-20 in PBS for 5 minutes each at room temperature with orbital shaking. Prior to antibody incubation, the chamber was removed and the well boundaries delineated with the hydrophobic barrier pen (Vector laboratories, #H-4000). One-drop Duolink blocking buffer was added and the slide was incubated at 37° C. for 30 minutes in a humidified chamber. The blocking solution was removed by tapping, followed by addition of 20 µg/ml of the anti-biotin (rabbit, Abcam, #G196266) and anti-NCEH1 (mouse, 4 µg/ml of in-house polyclonal). Generally, a 20 uL solution of the two primary antibodies per well was incubated at 4° C. overnight with orbital shaking. Primary antibodies solution was removed by tapping; the slide was washed in wash buffer A (150 mM NaCl, 10 mM Tris, 0.05% Tween 20, pH 7.3) three times for 5 minutes with gentle orbital shaking. Oligo-linked secondary antibodies were then diluted 5-fold in antibody diluent buffer (Duolink anti-mouse minus and anti-rabbit plus), added to the slide and incubated at 37° C. for 1 hour with orbital shaking. The secondary antibody-probe solution was removed by tapping the slide, followed by washing in buffer A three times with gentle orbital shaking. Ligation mixture from the Duolink In Situ Detection Reagents Orange kit was diluted five-fold in water prior to addition of ligase at a 40-fold dilution. The ligation mixture was incubated at 37° C. for 30 minutes with orbital shaking, removed, and the slide was washed twice. Finally, amplification solution was diluted 5-fold in water prior to addition of polymerase at 80-fold dilution. This amplification solution was added to each well, incubated at 37° C. for 90 minutes in the dark, and removed by washing with buffer B (0.1 M NaCl, 0.2 M Tris, pH 7.3) twice for 10 minutes each, followed by wash with 100-fold dilution of wash buffer B for 1 minute. Slides were dried at room temperature in the dark, mounted with 50 µL anti-fade mounting solution (Life technology, #P36961), covered with the cover glass (Fisher, #12-545M), and sealed with nail polish.

7. Activity-Based Proximity Ligation (ADPL) with "Direct-Conjugated Probe Structure".

PC3 cells were seeded, treated with probe, fixed, permeabilized and blocked as mentioned above. Then the cells were incubated with 20 µg/ml of streptavidin-oligonucleotide 1 and 4 µg/ml of anti-NCEH1-oligonucleotide 2 at 4° C. overnight with orbital shaking. After washing, the cells were incubated with the hybridization mixture containing 250 nM bridging oligonucleotide 1, 250 nM bridging oligonucleotide 2, 0.25 mg/ml BSA, 0.25 M NaCl, 0.05% Tween 20 and 1×T4 ligation buffer (10 mM Tris-acetate, 10 mM magnesium acetate, 50 mM potassium acetate, pH 7.5). After 30 minutes, the slide was washed with 1×T4 ligation buffer for 2 minutes and incubated with the ligation mixture containing 0.1 U/µL T4 DNA ligase, 1 mM ATP, 0.25 mg/ml BSA, 0.25 M NaCl, 0.05% Tween 20 and 1×T4 ligation buffer for 30 minutes. After wash with buffer A twice, the slide was incubated with amplification buffer containing 0.25 U/µL Phi29, 0.25 mM dNTP, 0.2 mg/ml BSA, 0.05% Tween 20 and 1×RCA buffer (50 mM Tris-HCl, 10 mM magnesium chloride, 10 mM ammonium sulfate, pH 7.5) for 100 minutes. Following wash with buffer A twice, the slide was incubated with detection mixture containing 10 nM detection oligonucleotide, 2×SSC buffer, 0.25 mg/ml BSA, 7.5 ng/µL Poly A, 0.05% Tween 20, and 1×DAPI for 30 minutes. The slide was washed, mounted and sealed as mentioned above.

ADPL image processing and quantification. ImageJ was used to process all images. Lossless TIFF files were employed to quantify fluorescence intensity. To simplify the image processing workflow a Macro script to automatically process all images was created. The workflow was as follows: open all channels for each field of view; designate a color for each channel; adjust brightness/contrast for all channels (applying the same levels for all conditions within and between experiments to allow for direct comparison); merge the channels together; adjust the image unit from pixel to micrometer; add scale bars; export the processed TIFF files for quantification. For quantitative analysis single cell boundaries were identified manually using the DIC image. Then the "ROI Manager" tool in ImageJ was utilized to add all the cell outlines as a collection and overlay with the ADPL channel to measure per-cell fluorescence intensity. Typical quantitative comparisons were made using data from three or more independent fields of view per independent biological replicate condition.

8. PLA-qPCR Quantification in Cell Lysate.

PC3 cell lysate was diluted in a 3-fold aliquots, PEG-8000 was added to a final concentration of 5% and incubated at 4° C. for 30 min, then centrifuged at 4,000 rpm for 20 minutes to remove potential assay interferences. 2 µL of each sample was added to 2 µL of probe mix resulting in a 200 pM concentration of each antibody-ssDNA probe in PBS pH 7.2, 20 µg/mL poly-A, 2 mM EDTA, 1% BSA, 0.05% goat IgG. Incubation were performed at 37° C. for 2 hours. As for the ligation reaction, 116 µL ligation solution were added containing 100 nM splint oligonucleotide, 2.5 units of Ampligase (Lucigen), 0.3 mM NAD+ (Sigma), 10 mM DTT, 20 mM Tris-HCl pH 8.3, 50 mM KCl, 1.5 mM MgCl2. Ligation proceeded at 30° C. for 15 minutes, and was terminated by adding 2.5 µL of the 10-fold dilution of the USER (Uracil-Specific Excision Reagent) enzyme (NEB, #M5505S) to degrade the uracil containing connectors for another 15 minutes. 5 µL of the ligation reaction was added to a 20 µL PCR tube using 200 nM primers for 18 cycles. The product was then diluted 2-fold in 1×TE buffer prior to real-time PCR. 9 µL of the diluted pre-amplification product was added to 11 µL of qPCR mix (NEB, #M3004S) resulting in a 0.9 µM of primers and 0.45 µM Taqman probe (IDT). Samples were run on a Roche LightCycler 480 with the default cycling protocol.

Example 3—Solution-Phase Activity-Dependent Proximity Ligation

As another alternative detection method, sADPL is complementary with gel-based and MS-based detection methods. In this design, the inventors treat the live cell with several family-wide probes. The probes will label all the members of the protein families. Then one could get the labeled proteome after the cell lysis. Then ab-oligo and SA-oligo can be added to bind with the target enzyme and the biotin tag, respectively. The proximity of the two oligos will stabilize the ternary complex with the splint to enable the ligation process. In this way, one can convert the activity detection into oligo detection. After pre-amplification and qPCR one could profile the activities among different cell states or use the clinical sample for prognosis. Likewise, one could also do the target engagement like gel-based or MS based method.

A summary of this assay is provided below:
1. Live cells are treated with a combination of activity-based family-wide probes to label the enzymes belonging to different families.
2. After cell lysis, labeled proteome is incubated with multiplexing antibody-oligos recognizing the POIs as well as streptavidin-oligo recognizing the biotin tag created from the activity probes. The proximity of the two oligos will stabilize the ternary complex with the splint to enable the ligation process.
3. In the oligo design, the orthogonal forward primers were employed for different antibody to enable the multiplexing real time PCR readout. However, the binding site to the splint were the same. So one universal splint was added to enable the ligation for multiple target simultaneously.
4. After pre-amplification, multiplexing qPCR is utilized to profile the activity in different cell state (like aggressive and non-aggressive cancer, cancer-related spheroid for the purpose of prognosis) and target engagement in vitro or in vivo.

FIG. 20 shows the detailed structure of sADPL design. Two amine modified oligos were conjugated to antibody and streptavidin, respectively. Forward primer (FP) and reverse primer (RP) were utilized in real time PCR step. The splint were complementary to the two probes to facilitate the ligation of the hydroxyl group and phosphate group at the two termini. The 3-base overhand at two ends were designed to prevent the connector oligonucleotide from giving rise to ligation independent products by acting as a primer and/or template for amplification. A Taqman probe was designed for real time PCR quantification. A standard curve for Taqman probe qPCR were generated with a series dilution of the ligation product. The amplification factor and PCR efficiency were obtained from the curve so that we could transform the CT difference into activity fold change.

Figure 21:
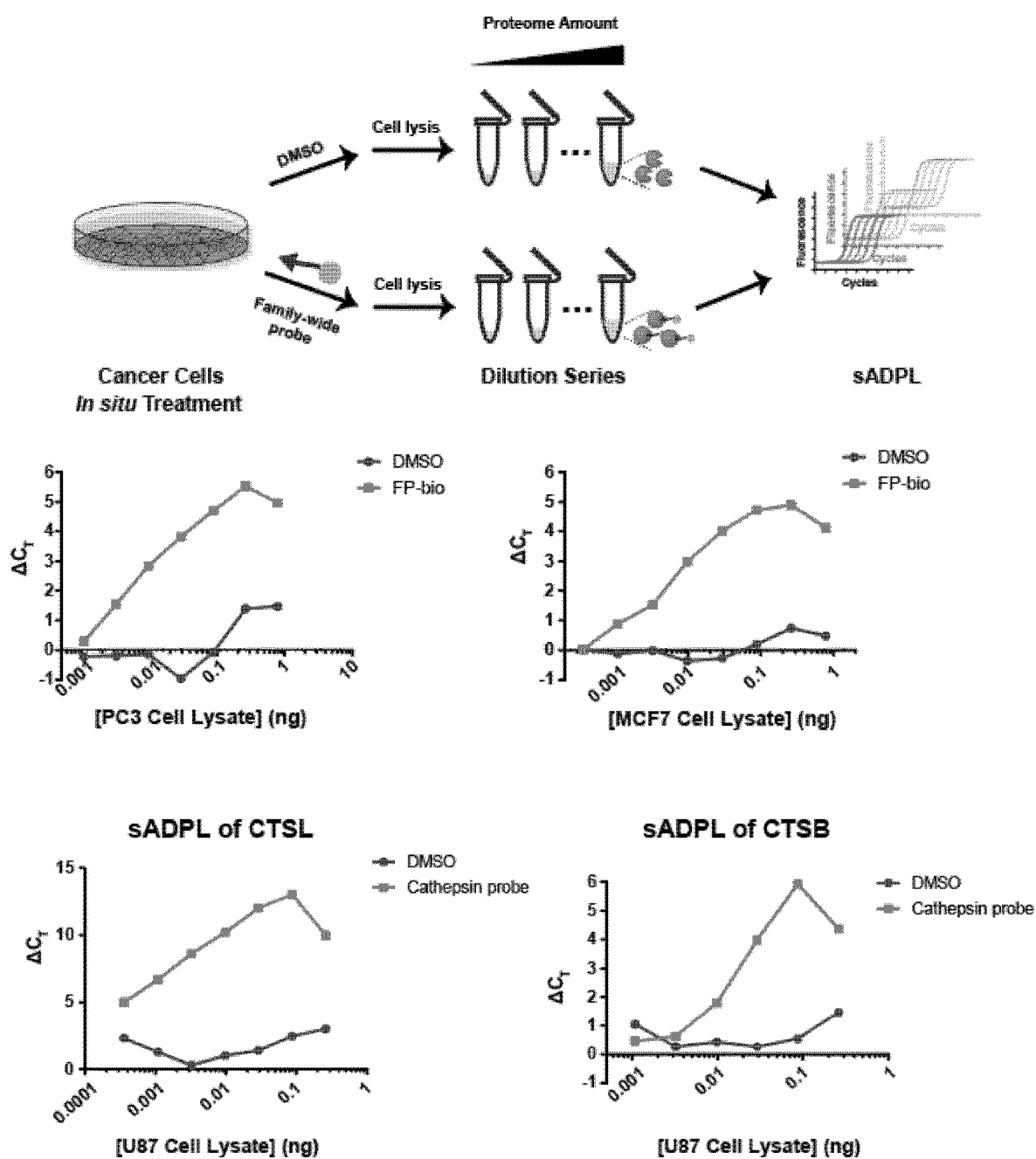
FIG. 21. sADPL for Diverse Targets. Live cells are treated with either DMSO or probe (FP-biotin for serine hydrolases or cathepsin family-wide probe for cathepsins) in situ. The cell proteome was diluted in a 3-fold series to test the dynamic range and limit of detection (LOD) for sADPL. The ΔCT in the y axis of the figure is the normalized Ct value with PBS (no proteome control). The Ct range for the dilution series is 5-8 cycles which represent a broad working window; the dynamic range is across several hundred to several thousand dilution fold.
Figure 24:
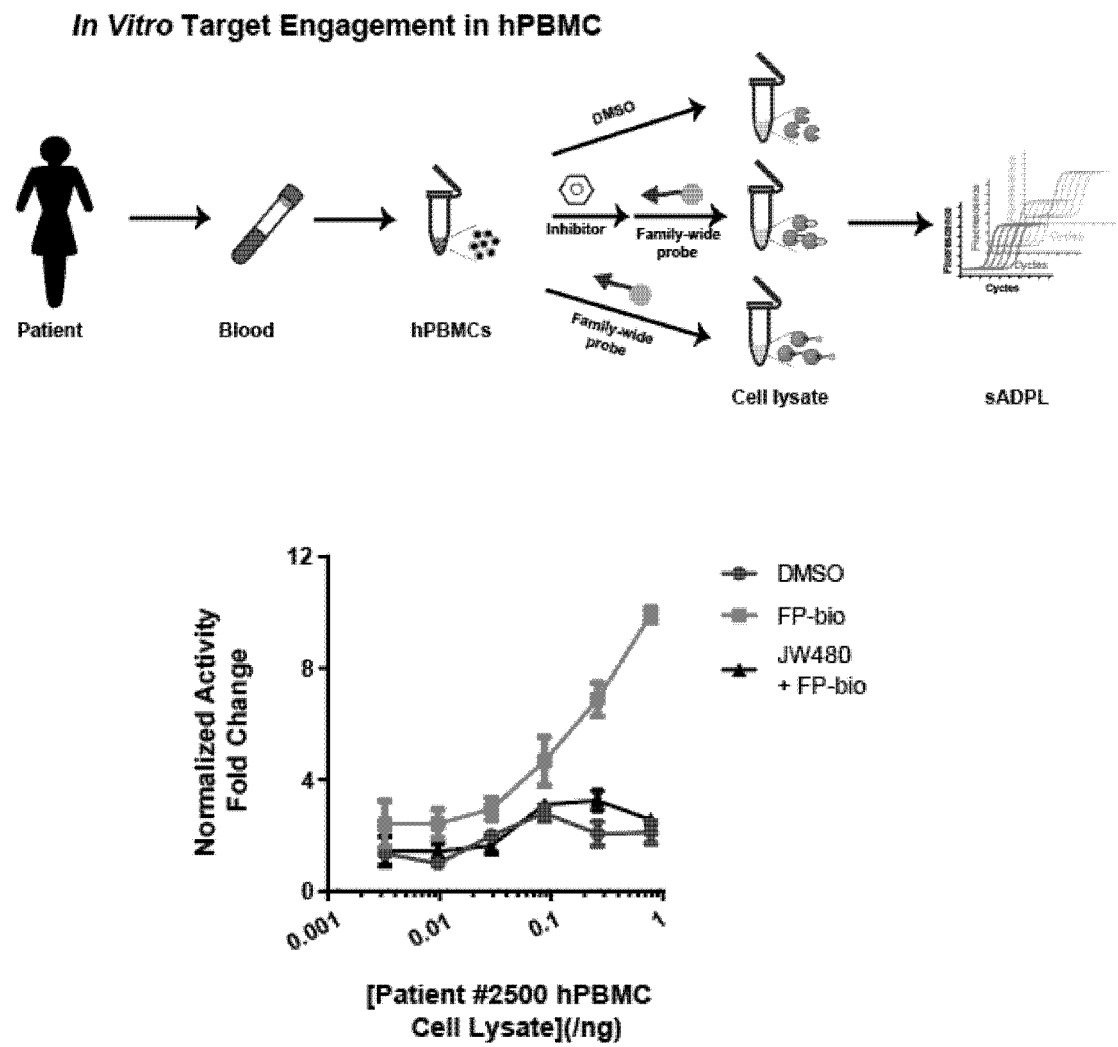
FIG. 24. Target Engagement in Patient-derived PBMCs. The human peripheral blood mononuclear cells (hPBMCs) were extracted from patient-derived blood samples. Likewise, hPBMCs were treated with DMSO as the control, with inhibitor prior to family wide probe to pre-block the active site, or with family-wide probe directly. Then sADPL workflow was applied to read out the CT difference. Similar with in situ target engagement result, JW480 competition will bring the activities down to the levels of DMSO controls to indicate the target engagements in hPBMCs.

With the optimized probe condition, sADPL can be used to detect the activity for diverse targets. FIG. 21 depicts the workflow. The cancer cells which has high expression of the target will be treated with DMSO or probe in situ (FP-biotin for serine hydrolases or cathepsin family-wide probe for cathepsins). Then the lysate will be diluted in a series for the following sADPL-qPCR measurement. This technology was used to detect the activity of diverse targets, including the membrane proteins, NCEH1, FAAH, MGLL and CD26 as well as the cytosolic protein Cathepsin B, cathepsin L. These proteins belong to different enzyme families, namely serine hydrolase and cathpsin. This data suggests that sADPL is amendable to diverse targets and diverse protein family. The best delta Ct value is about 4 to 6 cycles, that is 20-40 folds activity difference. And the dynamic range is about several hundred to several thousand dilution fold.

It was also found that the assay exhibited good reproducibility. The Ct values in two biological runs on two different days could correlated well (FIG. 22, left graph). Next, the detection limit and dynamic range between sADPL and WB were compared. It was found that sADPL has a broader dynamic range across these 7 dilution points, while WB only has a dynamic range of 4 dilution points; and sADPL has a detection limit that is about 1 million fold lower than WB (FIG. 22, right graph). Detection limits for biomarkers, including the assay LOD and sample LOD, is listed below:

| Biomarker | Sample LOD (ng) | Assay LOD (ng) |
|---|---|---|
| NCEH1 | 0.39 | 5.9E-4 |
| FAAH | 0.21 | 3.2E-4 |
| MGLL | 8.17 | 1.2E-2 |
| CD26 | 6.16 | 9.2E-3 |
| CTSB | 1.51 | 2.3E-3 |
| CTSL | 6.9E-3 | 1.0E-5 |

Since the inventors did about 700 fold dilution in the workflow, the sample LOD divided by the dilution fold could provide the assay LOD.

After a proof-of-principle experiment, the inventors tested sADPL for target engagement detection. Shown in FIG. 23 is the in vitro cell line based study. The inventors treated the cancer cells with DMSO, inhibitor then probe, probe only, then tested with sADPL platform. It was found that the in situ target engagement works well where the inhibitors block the activity sites and that the activity is similar with DMSO control group in both cases.

Figure 25:
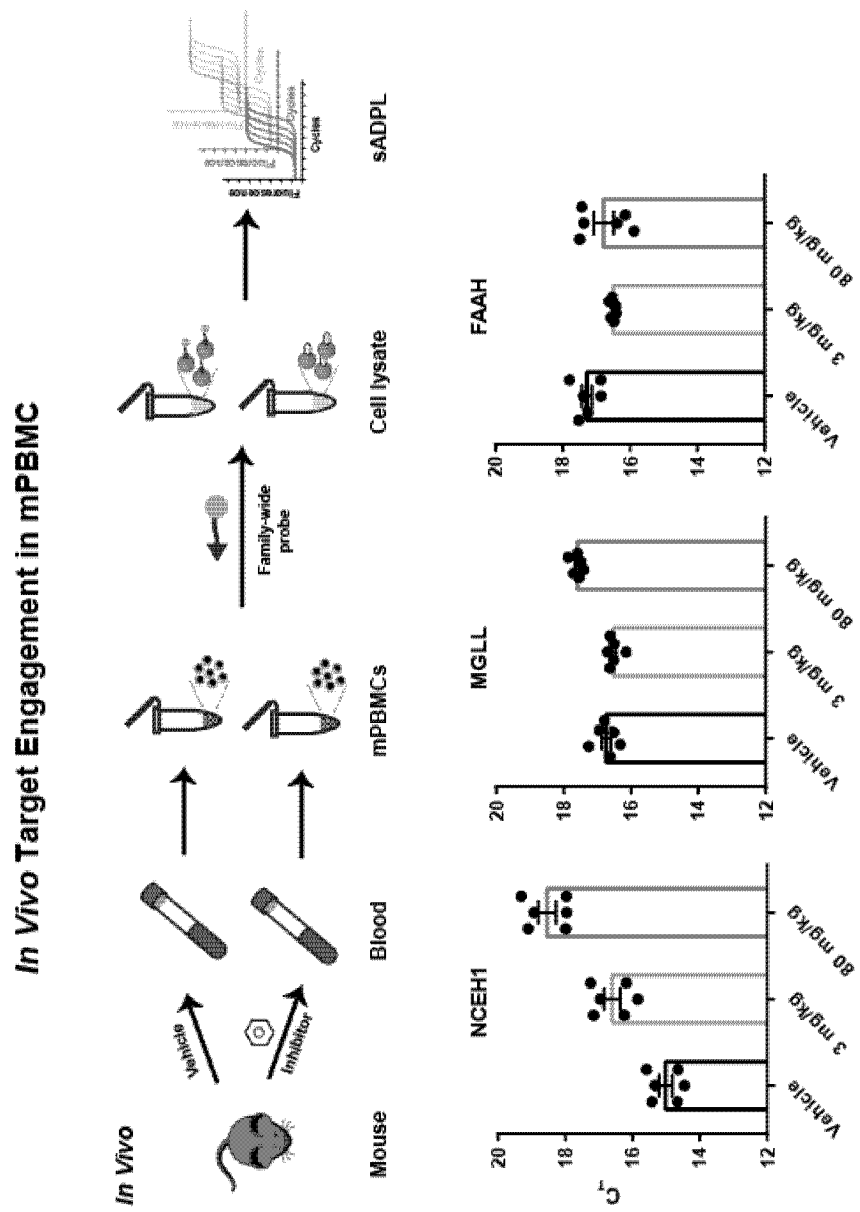
FIG. 25. In vivo Target Engagement. The mice were administrated with vehicle (PEG300) or NCEH1 inhibitor JW480 by oral gavage. Then the mPBMCs were acquired from the mouse blood and subjected to family wide probe treatment to profile the in vivo target engagement. According to the previous published results, 3 mg/kg dose was chosen to partially inhibit the enzyme, while 80 mg/kg to completely inhibit the enzyme. For NCEH1, raw Ct values indict that lower activity was observed in the partial inhibition and even lower activity in completely inhibition to indicate the in vivo target engagement. For the off-target, MGLL and FAAH, no target engagements were observed.

Following the in vitro study, in vivo target engagement was planned. In this experiment, the inventors orally gavaged the mice with vehicle or inhibitors, then collected the mPBMCs for probe treatment and sADPL measurement. Again, first the activity of NCEH1 was tested in mice PBMCs, and good activity was found. The delta Ct is over 7 cycles, which is over 100 fold change. This is shown in FIG. 25.

Figure 26:
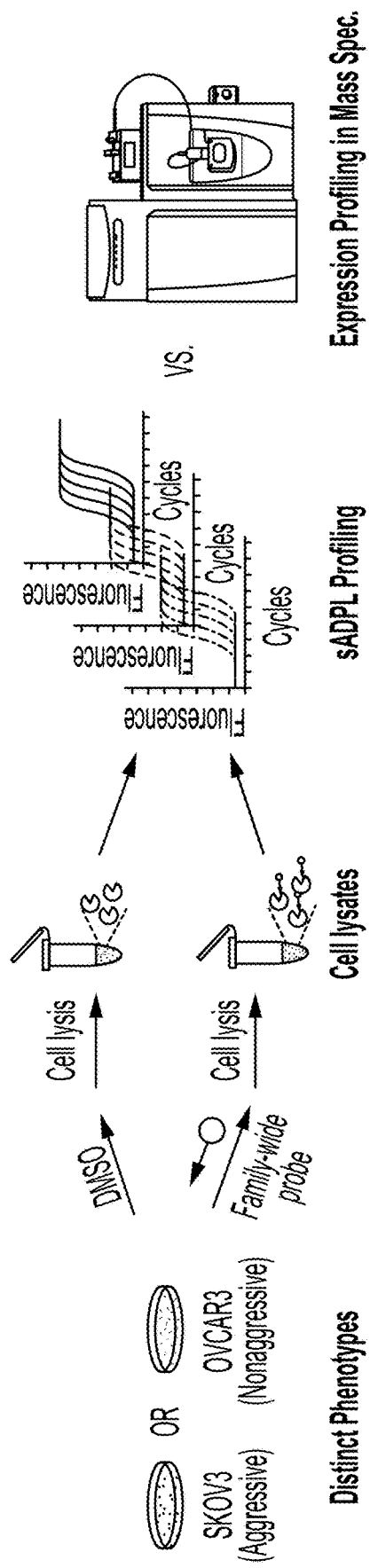
FIG. 26. Validation of sADPL for Activity Profiling. To validate the accuracy of sADPL, aggressive and non-aggressive ovarian cancer cell line SKOV3 and OVCAR3 were pulsed with DMSO or family-wide probe. Then the proteome were applied to sADPL measurement. The profiling of the biomarker activities will compared with published expression profiling generated in mass spectrometry based proteomic dataset.
Figure 27:
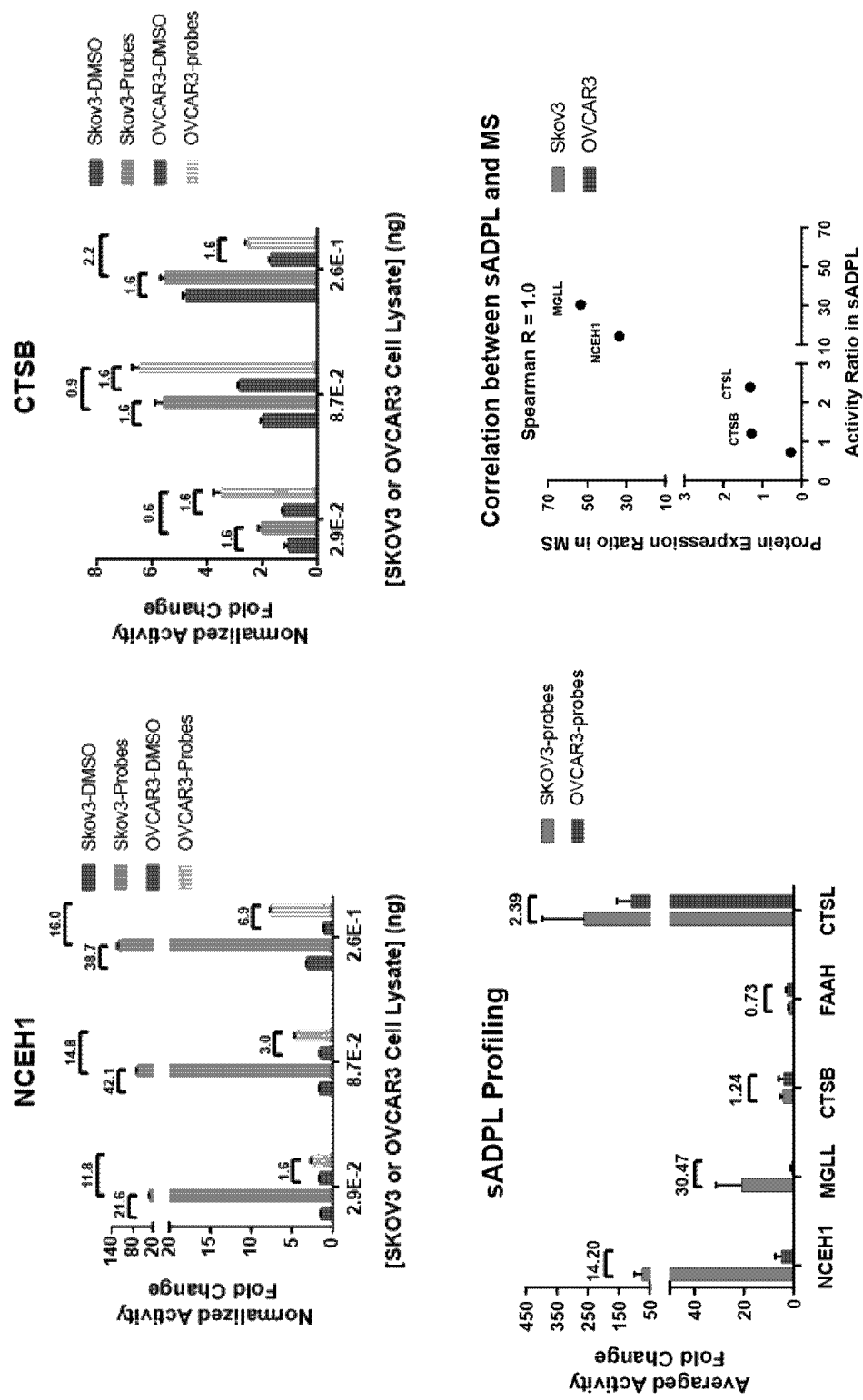
FIG. 27. Validation of sADPL for Activity Profiling. The activity profiling for NCEH1 and CTSB is shown as the representative examples. The X-axis denotes the concentration of the cell lysate, while the Y-axis is the normalized activity fold change by 'PBS' blank control. The values of activity ratios for SKOV3-probes over SKOV3-DMSO, OVCAR3-probes over OVCAR3-DMSO, SKOV3-probes over OVCAR3-probes were labeled within the bar graph. The normalized activity fold changes from three cell lysate concentrations were averaged for SKOV3-probes and OVCAR3-probes. The activity ratio between cell lines were calculated and labeled within the bar graph. Correlation between enzyme activity from sADPL and enzyme expression from mass spectrometry. The X-axis denotes the activity ratio for SKOV3-probes over OVCAR3-probes as shown before, while Y-axis is published protein expression ratio in mass spectrometry. The good correlation between two measurement indicate the accuracy of sADPL.

Next, the inventors performed activity profiling. At the beginning, the accuracy of sADPL profiling was verified by using the SKOV3 and OVCAR3 as a pair of aggressive and non-aggressive cells and treating them with DMSO or probe for sADPL measurement. Then, the inventors compared the sADPL data with the published MS data for the protein expression profiling. This is depicted in FIG. 26. By comparing the DMSO and probe, the inventors were able to determine the activity level of the target, with DMSO serving as an internal control. By comparing the two cell lines with probe, the inventors were able to determine the activity difference between the two cell lines. Several targets were measured. For example, for NCEH1, it was found to show high activity in SkOV3 cells but low activity in OVCAR3, and this is the activity difference in different lysate concentration. Similar results were found with FAAH, CTSB, MGLL, CTSL.

Figure 28:
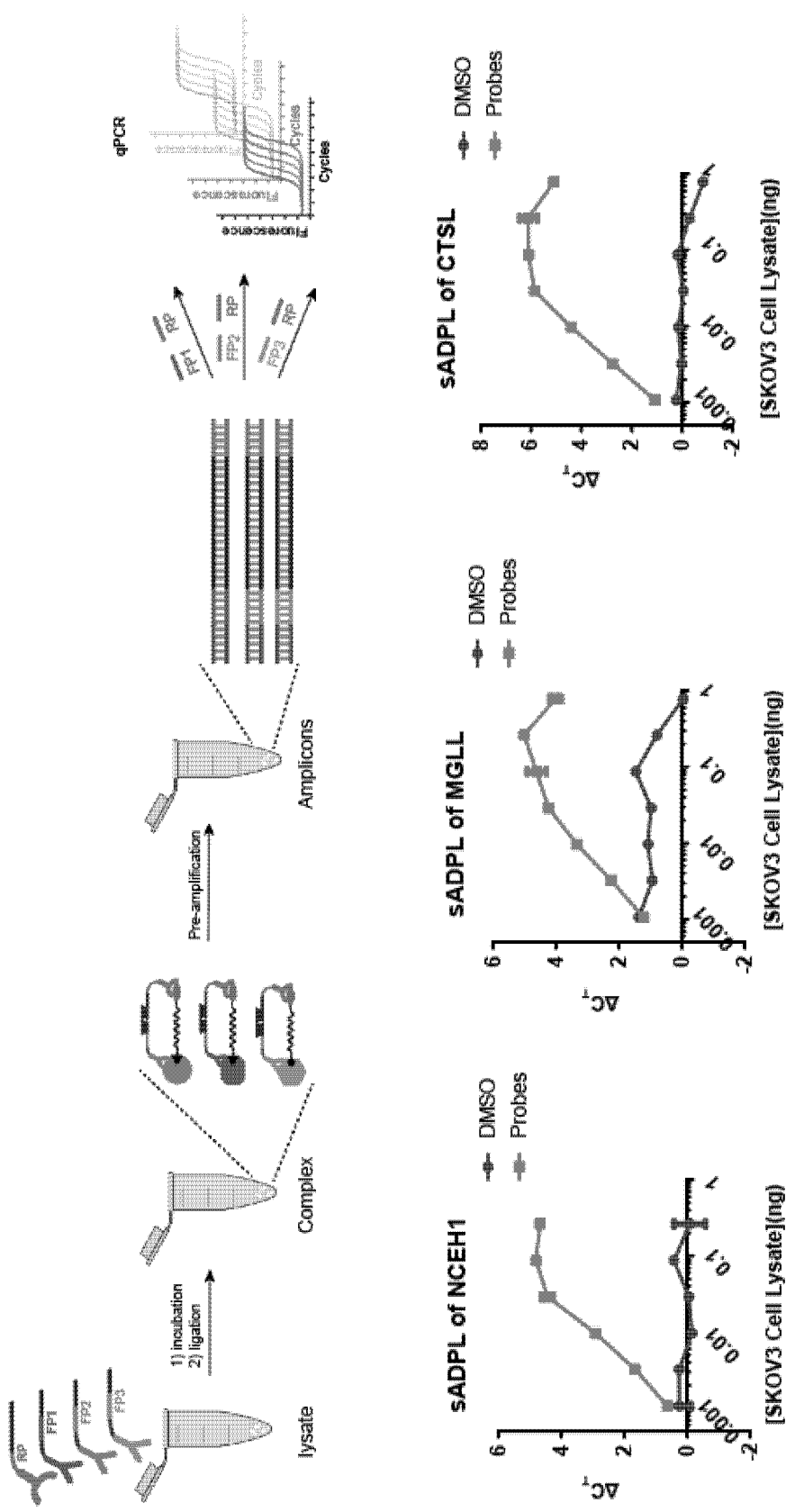
FIG. 28. Multiplexed sADPL. To test the feasibility of multiplexed sADPL, three different antibodies conjugated to oligonucleotides containing orthogonal forward primers and the universal streptavidin-oligo were added to the proteome at the same time. After incubation, ligation and pre-amplification, the amplicons representing the activities of each targets were deconvoluted by real time PCR with corresponding primers. Proteome were in situ treated with probes (cathepsin probe then serine hydrolase probe, FP-biotin) or DMSO, then analyzed in multiplexed sADPL where all the probes were added simultaneously. The ΔCT in the y axis of the figure is the normalized Ct value with PBS (no proteome control), x axis is the different concentration of the proteomes. The CT difference between 'DMSO' and 'probes' as well as the low signal in 'DMSO' control indicate the feasibility of multiplexed sADPL.
Figure 29:
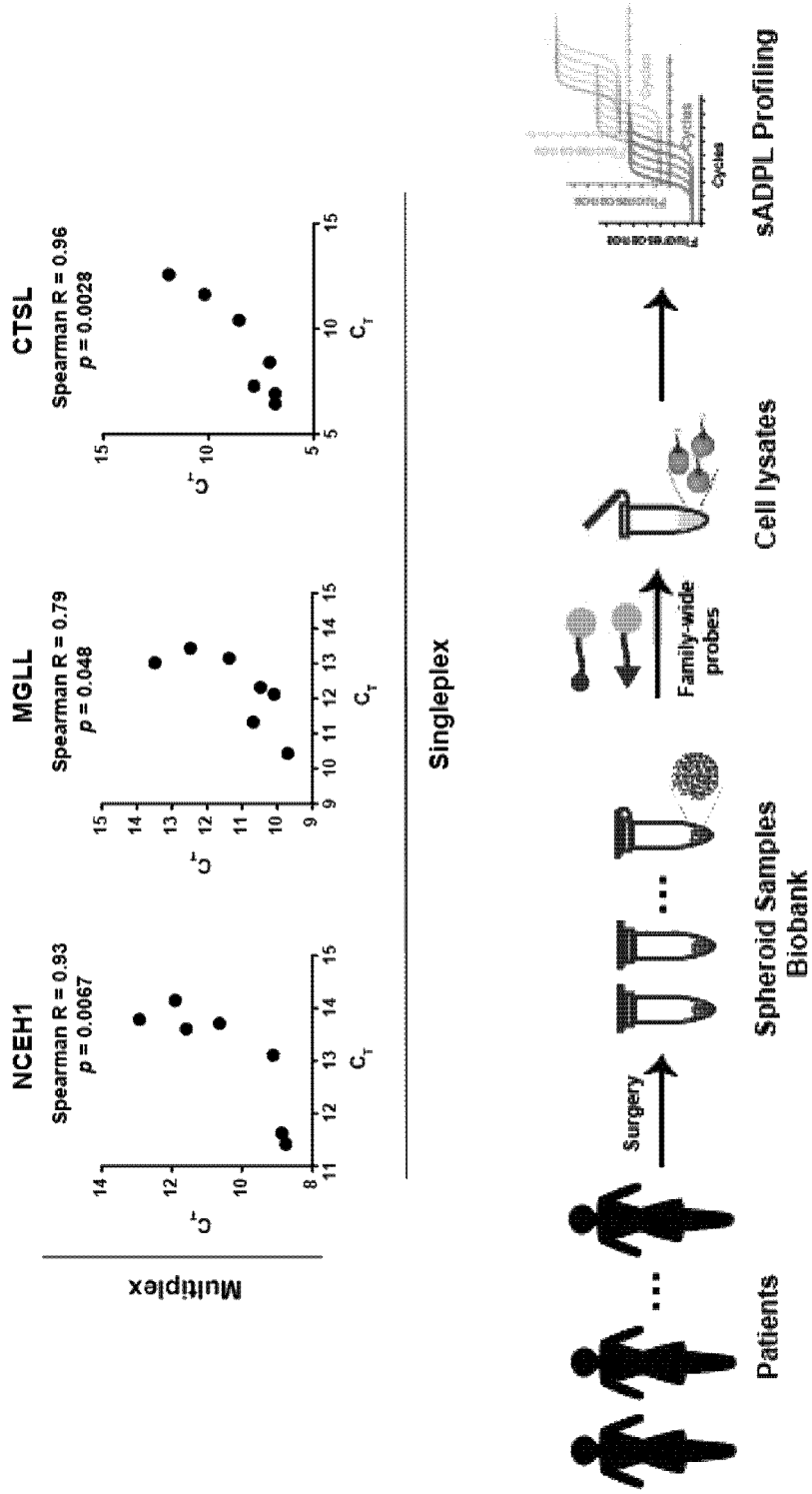
FIG. 29. Multiplexed sADPL. To further verify the multiplexed sADPL, the correlations between multiplex and singleplex were determined, the raw CT for different proteome concentration were plot. As an application of multiplexed sADPL, the biobanked patient-derived spheroid samples were pulsed with the probes and the activities were profiled by multiplexed sADPL.
Figure 30:
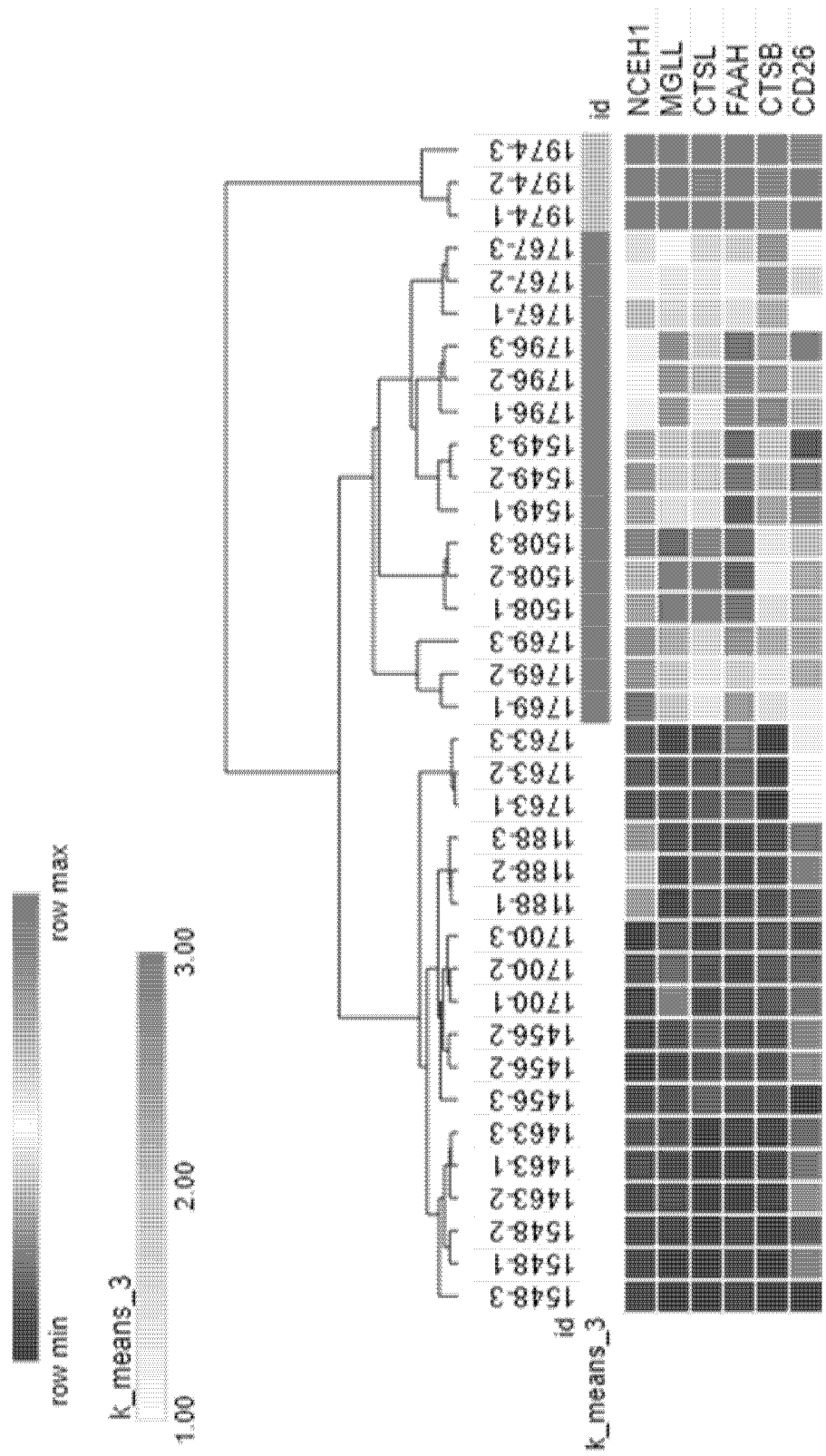
FIG. 30. Multiplexed sADPL. The activity of 6 enzymes, from two families, for 12 patients were measured in a single assay by multiplexing sADPL. The activities were plot and clustered.

FIGS. 28-30 show multiplexing with qPCR. The reverse primer on SA side was kept the same. The orthogonal forward primers, FP1, 2, 3 were designed, and all the four probes were simultaneously added. After incubation and ligation, the universal FP and RP were used to do the preamplification then tested with different primers for different enzyme activities.

Figure 31:
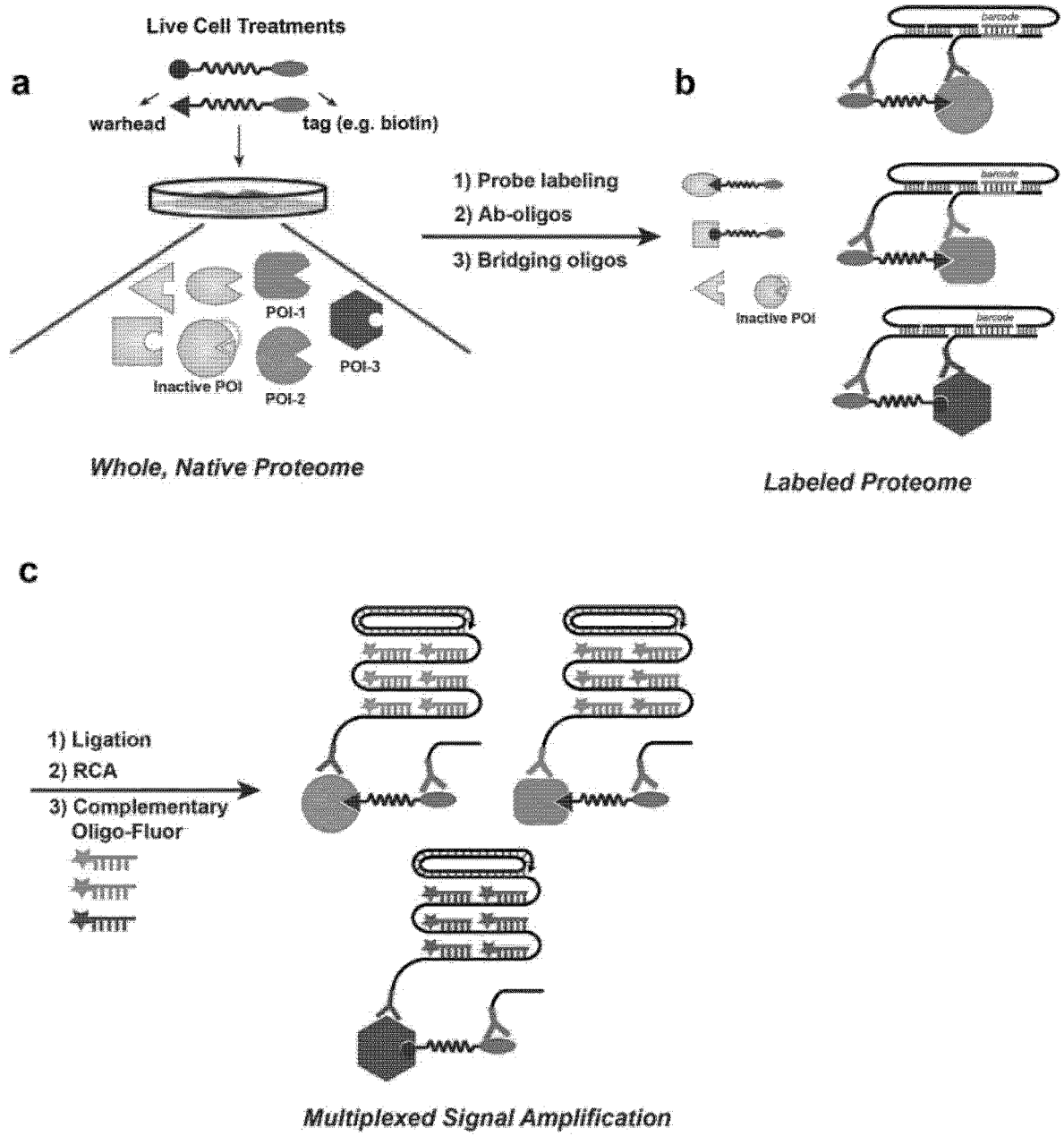
FIG. 31. 2nd Generation ADPL Imaging Design. In the first generation design, the oligonucleotides were conjugated to two orthogonal secondary antibodies (for example anti-mouse and anti-rabbit). So the options for these orthogonal secondary antibodies are limited. And 1st generation deign has no multiplexing capability. To solve this issue, a 2nd generation design was implemented, where the oligonucleotides were conjugated directly to antibodies or streptavidin and designed a barcode for each antibody for the purpose of multiplexing. In the workflow, the cells were pulsed with a combination of probes. Then antibody oligo, streptavidin-oligo and bridging oligonucleotides were added to facilitate the ligation process. After rolling circle amplification to amplify the signal, the complementary oligos with different fluorophores were added to image the fluorescent signals.

To further advance the ADPL design, the inventors developed the new ADPL imaging method with direct conjugation first. This design was found to be more specific. Then, the inventors added a barcode for multiplexing. Similarly, after live cell treatment, the inventors used the oligo directly conjugated to the primary ab. The inventors also added the barcode at the bridging oligo side. After the RCA, the complementary oligo coupled to different dye will detect its corresponding polymerization product. This is depicted in FIG. 31.

Figure 32:
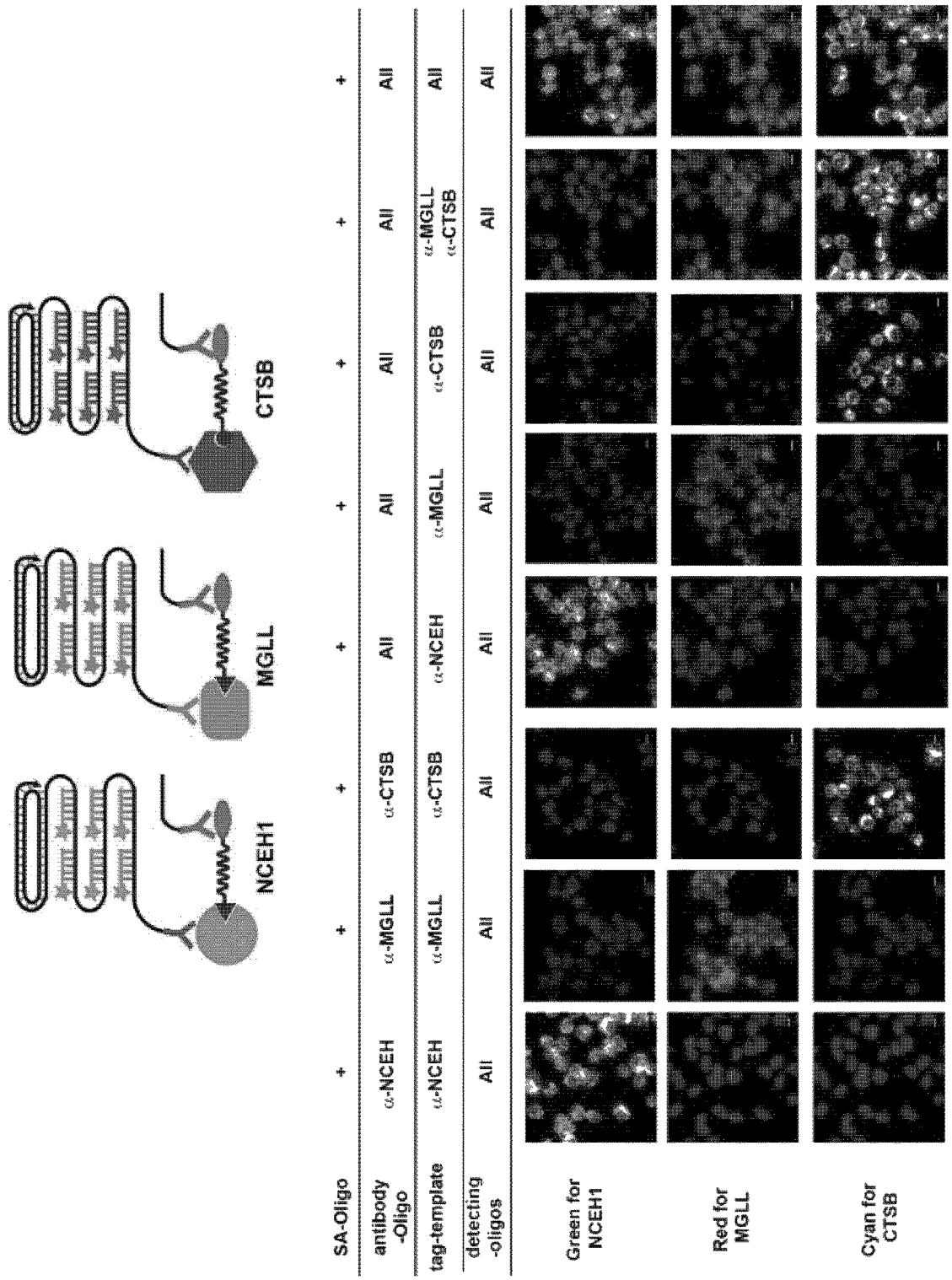
FIG. 32. Multiplexed ADPL-Between Family. To test the multiplexed ADPL imaging, 3 enzymes from different families were imaged: NCEH1 and MGLL are from serine hydrolase family, while CTSB is cathespin family. In the results, the first three columns are singleplex where only one antibody-oligo were added and only one tag-template (or barcode bridging oligo) was added as the standard. Then all three antibody-oligos were added simultaneously. If only one tag-template is added, then only signal in one channel will appear (column 4, 5, 6); if two tag-templates are added together (column 7), then the corresponding two channels signal will appear; likewise, if three tag templates are added, all three channels signal will show up (column 8). Together, this data demonstrate the multiplexed ADPL detection of the enzymes' activities.
Figure 33:
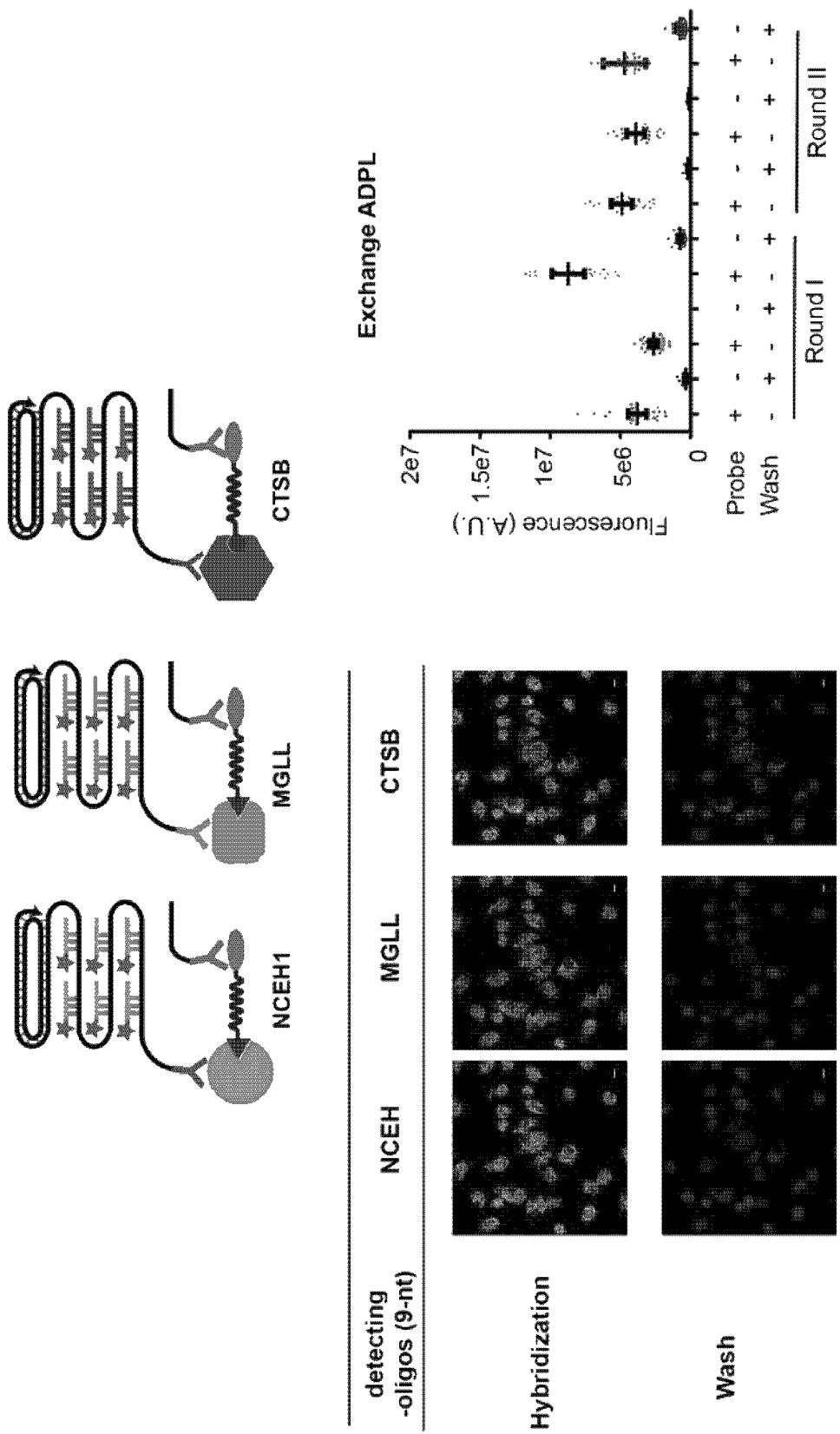
FIG. 33. Exchange ADPL. Notably, the spectrum overlap of the fluorophores in previously design will limit the multiplexing capability. To solve this issue, a short complementary detecting oligos (9 nt) conjugated to the same fluorophore was used. The short complementary oligos will bind with the amplified amplicon dynamically, where the signal could be easily be washed way and image with another oligo sequence. This one-by-one imaging method will breakthrough the limitation of fluorophore.
Figure 34:
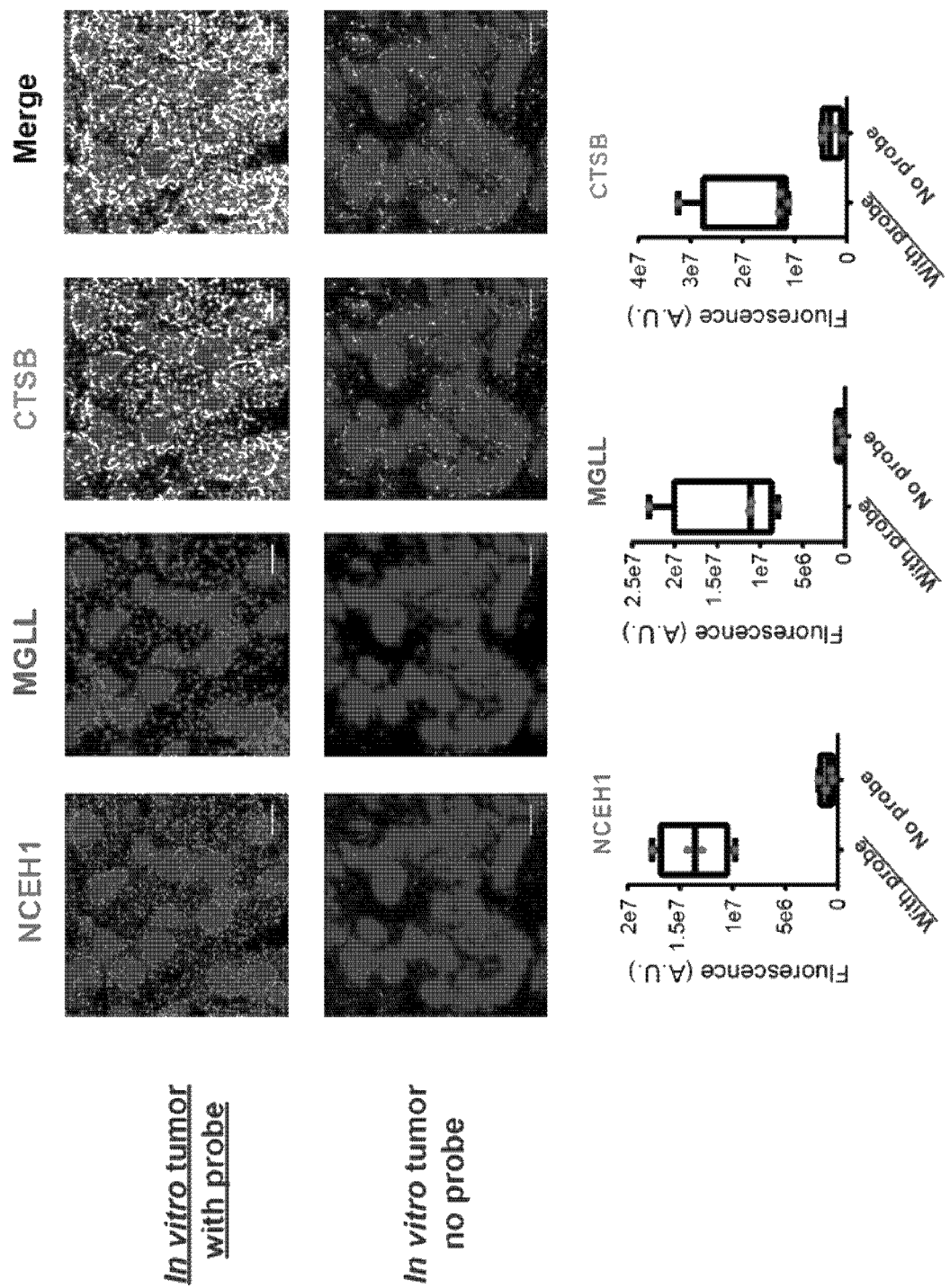
FIG. 34. Multiplexed ADPL in Xenograft Tissue. Last, the multiplexing ADPL was applied to mouse xenograft tumor tissue. The tumor tissues were treated with probes or DMSO, then imaging with multiplexing ADPL. The inventors could observe more signal in probes treated sample. This data indicate multiplexed ADPL is suitable for tissue samples.
Figure 36:
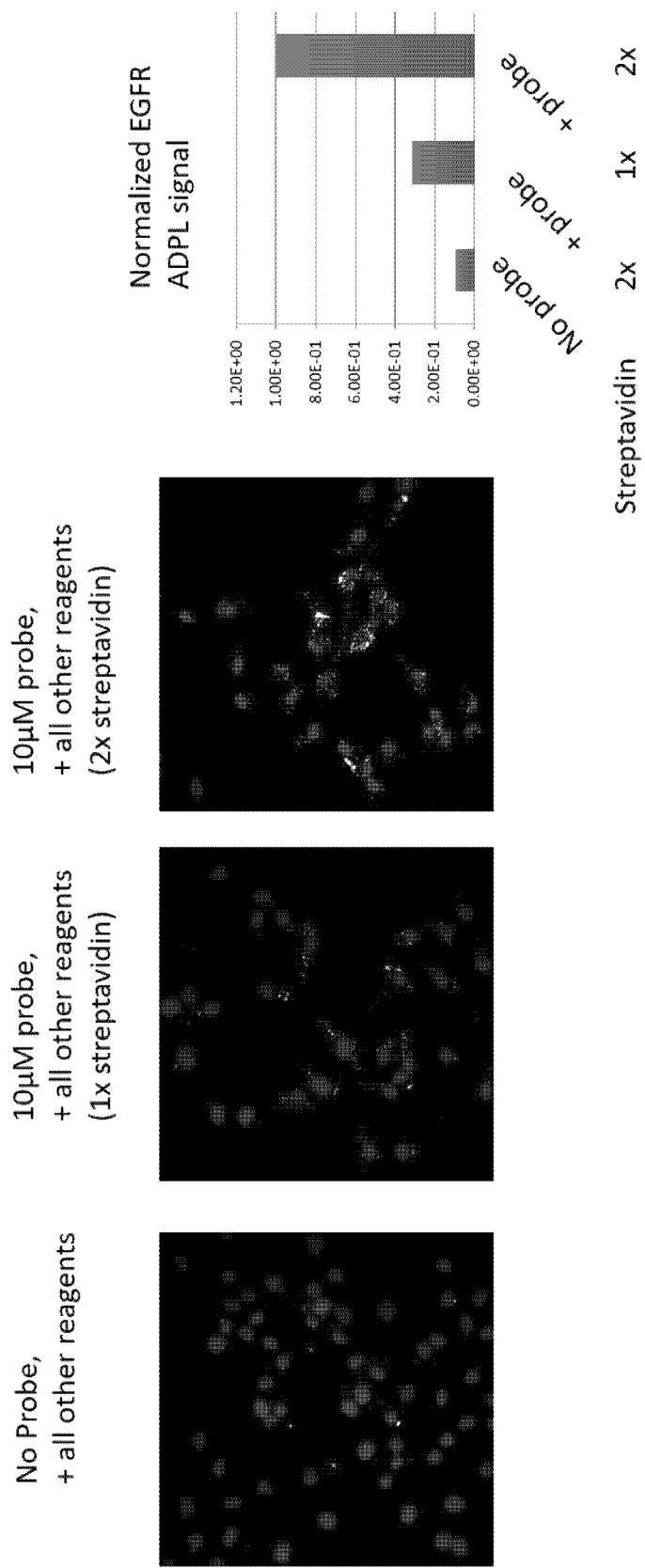
FIG. 36. Acylphosphate kinase probe imaging of active EGFR & SRC kinases. Hela cells, pulse treated with 10 µM kinase probe for 15 min with saponin in PBS, followed by ADPL sample processing and imaging with anti-EGFR and streptavidin to detect active EGFR.
Figure 37:
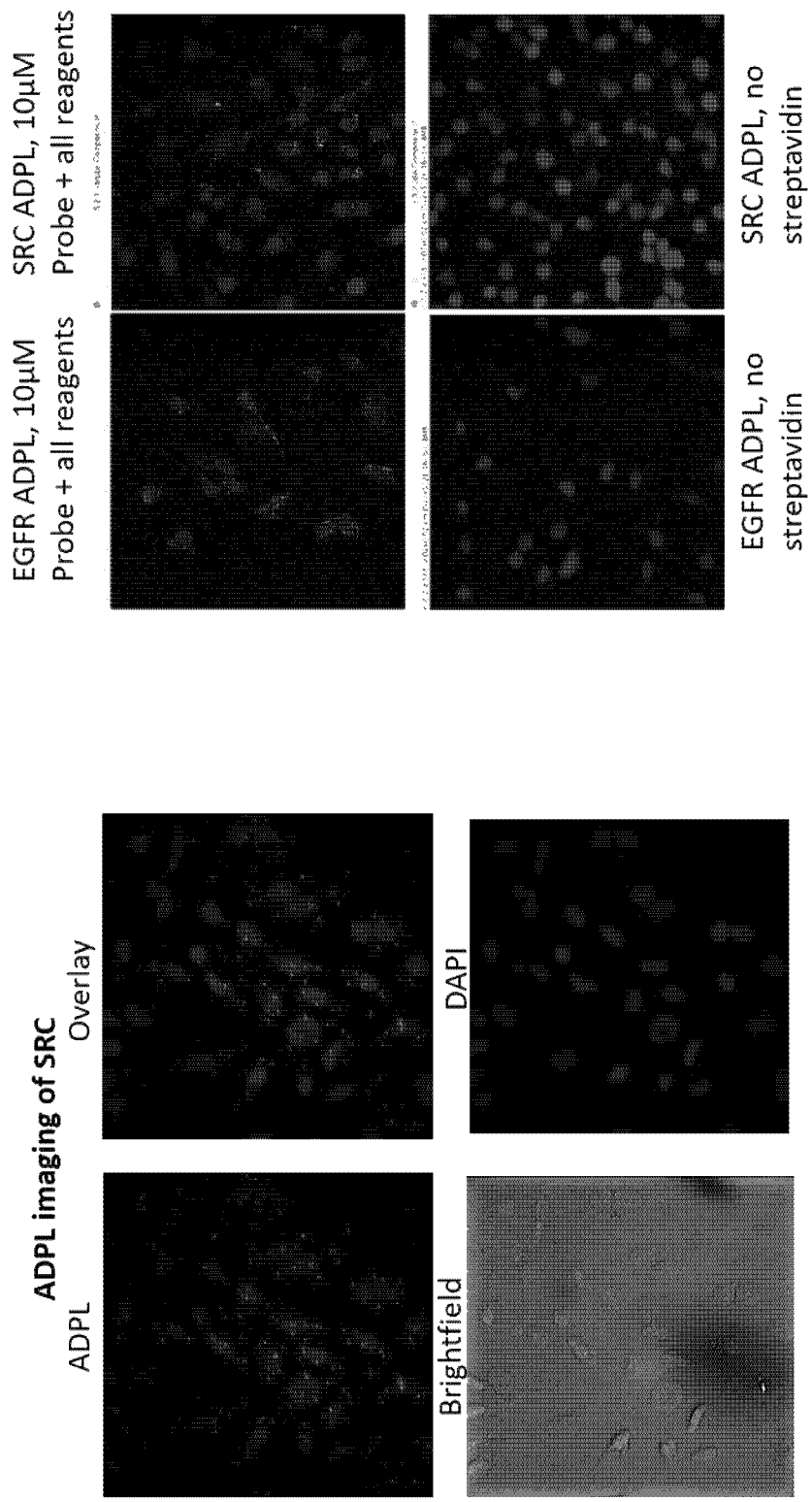
FIG. 37. Acylphosphate kinase probe imaging of active EGFR & SRC kinases. Hela cells, pulse treated with 5 µM probe for 15 min with saponin in PBS, followed by ADPL sample processing and imaging with anti-EGFR and anti-SRC antibodies.

As shown in FIGS. 32-34, multiplexing in between family targets was performed with NCEH1 and MGLL from the serine hydrolase family and CTSB from cathepsin family. The inventors first treated the cells with cathepsin probe and next with a serine hydrolase probe. Multiplexing capability was demonstrated for two and three target detection simultaneously. As an alternative to using a fluorescent dye, ADPL imaging was used. The inventors used a 9-nucleotide complementary oligo and imaged each target independently, washing away the imaging oligo in between.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

1. Agapakis, C. M., Boyle, P. M. & Silver, P. A. Natural strategies for the spatial optimization of metabolism in synthetic biology. Nature chemical biology 8, 527-535 (2012).
2. Pawson, T. & Nash, P. Protein-protein interactions define specificity in signal transduction. Genes & development 14, 1027-1047 (2000).
3. Kumar, A., et al. Subcellular localization of the yeast proteome. Genes & development 16, 707-719 (2002).
4. Yu, C. S., Chen, Y. C., Lu, C. H. & Hwang, J. K. Prediction of protein subcellular localization. Proteins 64, 643-651 (2006).
5. Walsh, C. Posttranslational modification of proteins: expanding nature's inventory, (Roberts and Co. Publishers, Englewood, Colo., 2006).
6. Fletcher, D. A. & Mullins, R. D. Cell mechanics and the cytoskeleton. Nature 463, 485-492 (2010).
7 Yu, H., Mouw, J. K. & Weaver, V. M. Forcing form and function: biomechanical regulation of tumor evolution. Trends in cell biology 21, 47-56 (2011).
8. Meloty-Kapella, L., Shergill, B., Kuon, J., Botvinick, E. & Weinmaster, G. Notch ligand endocytosis generates mechanical pulling force dependent on dynamin, epsins, and actin. Developmental cell 22, 1299-1312 (2012).
9. Eng, J. K., McCormack, A. L. & Yates, J. R. An approach to correlate tandem mass spectral data of peptides with amino acid sequences in a protein database. Journal of the American Society for Mass Spectrometry 5, 976-989 (1994).
10. Walther, T. C. & Mann, M. Mass spectrometry-based proteomics in cell biology. The Journal of cell biology 190, 491-500 (2010).
11. Cox, J. & Mann, M. Quantitative, high-resolution proteomics for data-driven systems biology. Annual review of biochemistry 80, 273-299 (2011).
12. Moellering, R. E. & Cravatt, B. F. How chemoproteomics can enable drug discovery and development. Chemistry & biology 19, 11-22 (2012).
13. Cravatt, B. F., Wright, A. T. & Kozarich, J. W. Activity-based protein profiling: from enzyme chemistry to proteomic chemistry. Annual review of biochemistry 77, 383-414 (2008).
14. Grammel, M. & Hang, H. C. Chemical reporters for biological discovery. Nature chemical biology 9, 475-484 (2013).
15. Liu, Y., Patricelli, M. P. & Cravatt, B. F. Activity-based protein profiling: the serine hydrolases. Proceedings of the National Academy of Sciences of the United States of America 96, 14694-14699 (1999).
16. Greenbaum, D., et al. Chemical approaches for functionally probing the proteome. Molecular & cellular proteomics: MCP 1, 60-68 (2002).
17. Adam, G. C., Sorensen, E. J. & Cravatt, B. F. Proteomic profiling of mechanistically distinct enzyme classes using a common chemotype. Nature biotechnology 20, 805-809 (2002).
18. Picotti, P., Aebersold, R. & Domon, B. The implications of proteolytic background for shotgun proteomics. Molecular & cellular proteomics: MCP 6, 1589-1598 (2007).
19. Bjornson, Z. B., Nolan, G. P. & Fantl, W. J. Single-cell mass cytometry for analysis of immune system functional states. Current opinion in immunology 25, 484-494 (2013).
20. Comi, T. J., Do, T. D., Rubakhin, S. S. & Sweedler, J. V. Categorizing Cells on the Basis of their Chemical Profiles: Progress in Single-Cell Mass Spectrometry. Journal of the American Chemical Society 139, 3920-3929 (2017).
21. Fredriksson, S., et al. Protein detection using proximity-dependent DNA ligation assays. Nature biotechnology 20, 473-477 (2002).

22. Soderberg, O., et al. Direct observation of individual endogenous protein complexes in situ by proximity ligation. Nature methods 3, 995-1000 (2006).
23. Gajadhar, A. & Guha, A. A proximity ligation assay using transiently transfected, epitope-tagged proteins: application for in situ detection of dimerized receptor tyrosine kinases. BioTechniques 48, 145-152 (2010).
24. Gu, G. J., et al. Protein tag-mediated conjugation of oligonucleotides to recombinant affinity binders for proximity ligation. New biotechnology 30, 144-152 (2013).
25. Robinson, P. V., Tsai, C. T., de Groot, A. E., McKechnie, J. L. & Bertozzi, C. R. Glyco-seek: Ultrasensitive Detection of Protein-Specific Glycosylation by Proximity Ligation Polymerase Chain Reaction. Journal of the American Chemical Society 138, 10722-10725 (2016).
26. Gao, X. & Hannoush, R. N. Single-cell in situ imaging of palmitoylation in fatty-acylated proteins. Nature protocols 9, 2607-2623 (2014).
27. Elfineh, L., et al. Tyrosine phosphorylation profiling via in situ proximity ligation assay. BMC cancer 14, 435 (2014).
28. Robinson, P. V., de Almeida-Escobedo, G., de Groot, A. E., McKechnie, J. L. & Bertozzi, C. R. Live-Cell Labeling of Specific Protein Glycoforms by Proximity-Enhanced Bioorthogonal Ligation. Journal of the American Chemical Society 137, 10452-10455 (2015).
29. Lemke, E. A. & Schultz, C. Principles for designing fluorescent sensors and reporters.
Nature chemical biology 7, 480-483 (2011).
30. Chang, J. W., Moellering, R. E. & Cravatt, B. F. An activity-based imaging probe for the integral membrane hydrolase KIAA1363. Angew Chem Int Ed Engl 51, 966-970 (2012).
31. Chang, J. W., Cognetta, A. B., 3rd, Niphakis, M. J. & Cravatt, B. F. Proteome-wide reactivity profiling identifies diverse carbamate chemotypes tuned for serine hydrolase inhibition. ACS chemical biology 8, 1590-1599 (2013).
32. Puri, A. W., Broz, P., Shen, A., Monack, D. M. & Bogyo, M. Caspase-1 activity is required to bypass macrophage apoptosis upon Salmonella infection. Nature chemical biology 8, 745-747 (2012).
33. Buchebner, M., et al. Cholesteryl ester hydrolase activity is abolished in HSL−/− macrophages but unchanged in macrophages lacking KIAA1363. Journal of lipid research 51, 2896-2908 (2010).
34. Okazaki, H., et al. Identification of neutral cholesterol ester hydrolase, a key enzyme removing cholesterol from macrophages. The Journal of biological chemistry 283, 33357-33364 (2008).
35. Chiang, K. P., Niessen, S., Saghatelian, A. & Cravatt, B. F. An enzyme that regulates ether lipid signaling pathways in cancer annotated by multidimensional profiling. Chemistry & biology 13, 1041-1050 (2006).
36. Chang, J. W., Nomura, D. K. & Cravatt, B. F. A potent and selective inhibitor of KIAA1363/AADACL1 that impairs prostate cancer pathogenesis. Chemistry & biology 18, 476-484 (2011).
37. Jessani, N., Liu, Y., Humphrey, M. & Cravatt, B. F. Enzyme activity profiles of the secreted and membrane proteome that depict cancer cell invasiveness. Proceedings of the National Academy of Sciences of the United States of America 99, 10335-10340 (2002).
38. Jessani, N., et al. A streamlined platform for high-content functional proteomics of primary human specimens. Nature methods 2, 691-697 (2005).
39. Shaw, T. J., Senterman, M. K., Dawson, K., Crane, C. A. & Vanderhyden, B. C. Characterization of intraperitoneal, orthotopic, and metastatic xenograft models of human ovarian cancer. Molecular therapy: the journal of the American Society of Gene Therapy 10, 1032-1042 (2004).
40. Okerberg, E. S., et al. High-resolution functional proteomics by active-site peptide profiling. Proceedings of the National Academy of Sciences of the United States of America 102, 4996-5001 (2005).
41. Bright, N. A., Davis, L. J. & Luzio, J. P. Endolysosomes Are the Principal Intracellular Sites of Acid Hydrolase Activity. Current biology: CB 26, 2233-2245 (2016).
42. Simon, G. M., Niphakis, M. J. & Cravatt, B. F. Determining target engagement in living systems. Nature chemical biology 9, 200-205 (2013).
43. Heath, J. R., Ribas, A. & Mischel, P. S. Single-cell analysis tools for drug discovery and development. Nature reviews. Drug discovery 15, 204-216 (2016).
44. Weroha, S. J., et al. Tumorgrafts as in vivo surrogates for women with ovarian cancer. Clinical cancer research: an official journal of the American Association for Cancer Research 20, 1288-1297 (2014).
45. Weiswald, L. B., Bellet, D. & Dangles-Marie, V. Spherical cancer models in tumor biology. Neoplasia 17, 1-15 (2015).
46. Jones, L. H. Cell permeable affinity- and activity-based probes. Future medicinal chemistry 7, 2131-2141 (2015).
47. Speers, A. E., Adam, G. C. & Cravatt, B. F. Activity-based protein profiling in vivo using a copper(i)-catalyzed azide-alkyne [3+2] cycloaddition. Journal of the American Chemical Society 125, 4686-4687 (2003).
48. Bunnage, M. E., Chekler, E. L. & Jones, L. H. Target validation using chemical probes. Nature chemical biology 9, 195-199 (2013).
49. Nomura, D. K., Dix, M. M. & Cravatt, B. F. Activity-based protein profiling for biochemical pathway discovery in cancer. Nature reviews. Cancer 10, 630-638 (2010).
50. Tully, S. E. & Cravatt, B. F. Activity-based probes that target functional subclasses of phospholipases in proteomes. Journal of the American Chemical Society 132, 3264-3265 (2010).
51. Moellering, R. E. & Cravatt, B. F. Functional lysine modification by an intrinsically reactive primary glycolytic metabolite. Science 341, 549-553 (2013).
52. Davidowitz, R. A., et al. Mesenchymal gene program-expressing ovarian cancer spheroids exhibit enhanced mesothelial clearance. The Journal of clinical investigation 124, 2611-2625 (2014).
53. a) T. Sano, C. L. Smith, C. R. Cantor, Science 1992, 258, 120-122; b) M. Adler, R. Wacker, C. M. Niemeyer, Analyst 2008, 133, 702-718.
54. a) S. Fredriksson, M. Gullberg, J. Jarvius, C. Olsson, K. Pietras, S. M. Gústafsdóttir, A. Östman, U. Landegren, Nature biotechnology 2002, 20, 473; b) O. Soderberg, M. Gullberg, M. Jarvius, K. Ridderstrale, K.-J. Leuchowius, J. Jarvius, K. Wester, P. Hydbring, F. Bahram, L.-G. Larsson, Nature methods 2006, 3, 995.
55. M. Lundberg, A. Eriksson, B. Tran, E. Assarsson, S. Fredriksson, Nucleic acids research 2011, 39, e102-e102.
56. R. Jungmann, M. S. Avendaño, M. Dai, J. B. Woehrstein, S. S. Agasti, Z. Feiger, A. Rodal, P. Yin, Nature methods 2016, 13, 439.
57. R. C. Bailey, G. A. Kwong, C. G. Radu, O. N. Witte, J. R. Heath, Journal of the American Chemical Society 2007, 129, 1959-1967.

58. G. Li, J. E. Montgomery, M. A. Eckert, J. W. Chang, S. M. Tienda, E. Lengyel, R. E. Moellering, Nature communications 2017, 8, 1775.
59. C. M. Niemeyer, T. Sano, C. L. Smith, C. R. Cantor, Nucleic Acids Research 1994, 22, 5530-5539.
60. Y. Chen, M. T. Kim, L. Zheng, G. Deperalta, F. Jacobson, Bioconjugate chemistry 2016, 27, 2037-2047.
61. O. Koniev, G. Leriche, M. Nothisen, J.-S. Remy, J.-M. Strub, C. Schaeffer-Reiss, A. Van Dorsselaer, R. Baati, A. Wagner, Bioconjugate chemistry 2014, 25, 202-206.
62. J. F. Ponte, X. Sun, N. C. Yoder, N. Fishkin, R. Laleau, J. Coccia, L. Lanieri, M. Bogalhas, L. Wang, S. Wilhelm, Bioconjugate chemistry 2016, 27, 1588-1598.
63. I. A. Kozlov, P. C. Melnyk, K. E. Stromsborg, M. S. Chee, D. L. Barker, C. Zhao, Biopolymers 2004, 73, 621-630.
64. H. Gong, I. Holcomb, A. Ooi, X. Wang, D. Majonis, M. A. Unger, R. Ramakrishnan, Bioconjug Chem 2016, 27, 217-225.
65. I. Dovgan, S. Ursuegui, S. Erb, C. Michel, S. Kolodych, S. Cianferani, A. Wagner, Bioconjug Chem 2017, 28, 1452-1457.
66. a) C. B. Rosen, A. L. Kodal, J. S. Nielsen, D. H. Schaffert, C. Scavenius, A. H. Okholm, N. V. Voigt, J. J. Enghild, J. Kjems, T. Tørring, Nature chemistry 2014, 6, 804; b) J. B. Trads, T. Tørring, K. V. Gothelf, Accounts of chemical research 2017, 50, 1367-1374.
67. M. Jarvius, J. Paulsson, I. Weibrecht, K.-J. Leuchowius, A.-C. Andersson, C. Wahlby, M. Gullberg, J. Botling, T. Sjöblom, B. Markova, Molecular & cellular proteomics 2007, 6, 1500-1509.
68. S. S. Agasti, Y. Wang, F. Schueder, A. Sukumar, R. Jungmann, P. Yin, Chemical science 2017, 8, 3080-3091.
69. a) M. Gullberg, S. M. Gústafsdóttir, E. Schallmeiner, J. Jarvius, M. Bjarnegørd, C. Betsholtz, U. Landegren, S. Fredriksson, Proceedings of the National Academy of Sciences of the U.S. Pat. No. 2,004,101, 8420-8424; b) S. Fredriksson, W. Dixon, H. Ji, A. C. Koong, M. Mindrinos, R. W. Davis, Nature methods 2007, 4, 327; c) E. Schallmeiner, E. Oksanen, O. Ericsson, L. Spøngberg, S. Eriksson, U.-H. Stenman, K. Pettersson, U. Landegren, Nature methods 2007, 4, 135; d) R. Y. Nong, D. Wu, J. Yan, M. Hammond, G. J. Gu, M. Kamali-Moghaddam, U. Landegren, S. Darmanis, Nature protocols 2013, 8, 1234; e) C. Albayrak, C. A. Jordi, C. Zechner, J. Lin, C. A. Bichsel, M. Khammash, S. Tay, Molecular cell 2016, 61, 914-924; f) P. V. Robinson, C.-t. Tsai, A. E. de Groot, J. L. McKechnie, C. R. Bertozzi, Journal of the American Chemical Society 2016, 138, 10722-10725.
70. a) V. Chudasama, A. Maruani, S. Caddick, Nature chemistry 2016, 8, 114; b) A. Beck, L. Goetsch, C. Dumontet, N. Corvaïa, Nature Reviews Drug Discovery 2017, 16, 315.

The invention claimed is:

1. A method for evaluating two or more target proteins of interest from the same family in a specified functional form, the method comprising:

(i) contacting a sample comprising or suspected of comprising the two or more proteins of interest with a molecular construct comprising: a targeting group operatively linked to a retrieval tag; wherein the targeting group comprises a small molecule probe that specifically binds and covalently links to the specialized functional form of the two or more target proteins of interest;

(ii) contacting the sample with at least two antibody-oligo constructs, wherein at least one of the constructs comprises a first antibody operatively linked to a first oligo and at least a second construct comprises a second antibody operatively linked to a second oligo; wherein the first antibody specifically binds to one of the two or more target proteins of interest and the second antibody specifically binds to the other of the two or more target proteins of interest;

(iii) contacting the sample with a second molecular construct comprising a retrieval tag binder operatively linked to a retrieval oligo;

(iv) incubating the sample under conditions sufficient for the ligation or annealing of the first oligo to the retrieval oligo when the first and retrieval oligos are in close proximity to each other and ligation of the second oligo to the retrieval oligo when the second and retrieval oligos are in close proximity to each other; and (v) detecting the ligated or annealed first and retrieval oligo and the ligated or annealed second and retrieval oligo.

2. The method of claim 1, wherein the two or more target proteins of interest are enzymes.

3. The method of claim 1, wherein the method further comprises determining the abundance of each of the two or more target proteins of interest in the specialized functional form in the sample, wherein determining the abundance of protein in a specialized functional form comprises one or more of: (i) PCR amplification of the ligated first and retrieval oligo and of the ligated second and retrieval oligo or PCR amplification of the first and second oligo and (ii) primer extension and/or PCR amplification of the annealed first and retrieval oligo and of the annealed second and retrieval oligo.

4. The method of claim 1, wherein the retrieval tag is covalently linked to the targeting group through a linker.

5. The method of claim 4, wherein the linker is organic or is an aliphatic linker.

6. The method of any claim 1, wherein the first antibody is covalently linked to a first oligo and/or the second antibody is covalently linked to a second oligo.

7. The method of claim 1, wherein the first antibody and/or second antibody is operatively linked to a first and/or second oligo, respectively, through a non-covalently bound secondary antibody and wherein the non-covalently bound secondary antibody is covalently linked to the first or second oligo.

8. The method of claim 1, wherein the first, second, and/or retrieval oligos are single-stranded oligos.

9. The method of claim 1, wherein (ii) further comprises contacting the sample with one or more bridging oligos, wherein at least one of the one or more bridging oligos comprises complementary regions to both the first oligo and the retrieval oligo and at least one of the one or more bridging oligos comprises complementary regions to both the second oligo and the retrieval oligo.

10. The method of claim 1, wherein the method further comprises performing rolling circle amplification after step (iv).

11. The method of claim 1, wherein the method further comprises contacting the sample with a first labeled primer and/or second labeled primer, wherein the first labeled primer is specifically complementary to the first oligo and non-complementary to the second oligo and the second labeled primer is specifically complementary to the second oligo and non-complementary to the first oligo.

12. The method of claim 1, wherein the sample in (i) comprises live cells.

13. The method of claim 12, wherein the method further comprises spatially detecting the specialized functional form of the two or more target proteins of interest.

14. The method of claim 1, wherein the two or more target proteins of interest are non-modified proteins and/or are expressed from endogenous non-genetically modified genes.

15. The method of claim 1, wherein the sample comprises less than 5000 cells and/or less than 1 μg of total protein.

16. The method of claim 1, wherein the method further comprises determining the total amount of target proteins of interest.

17. The method of claim 1, wherein the method further comprises adding a suspected target protein modifier.

18. The method of claim 1, wherein the first antibody operatively linked to the first oligo and/or the second antibody operatively linked to the second oligo comprises a molecular label.

19. The method of claim 18, wherein the molecular label comprises a fluorescent molecule.

20. The method of claim 1, wherein the small molecule probe comprises fluorophosphonate, diphenylphosphonate, sulfonyl fluoride, acyloxymethyl ketone, phenoxymethylketone, vinyl sulfone, epoxide, halomethylketone, alpha-haloester, alpha-haloamide, $\alpha$, $\beta$-unsaturated ester, $\alpha$, $\beta$-unsaturated ketone, diazomethylketone, acyl phosphate, acylphosphonate, hydroxamate, carbamate, ester, thioester, 2-deoxy-2-fluoro glycoside, $\alpha$-bromobenzylphosphonate, nucleotide acyl phosphate, and/or 2-ethynylnaphthalene.

* * * * *

UNITED STATES PATENT AND TRADEMARK OFFICE
CERTIFICATE OF CORRECTION

PATENT NO. : 12,276,654 B2  Page 1 of 1
APPLICATION NO. : 15/733113
DATED : April 15, 2025
INVENTOR(S) : Raymond E. Moellering and Gang Li It is certified that error appears in the above-identified patent and that said Letters Patent is hereby corrected as shown below:

In the Claims

In Claim 6, Column 81, Line 39, delete "any".

Signed and Sealed this
Fifteenth Day of July, 2025

Coke Morgan Stewart
*Acting Director of the United States Patent and Trademark Office*

SEQUENCE LISTING

```
<160> NUMBER OF SEQ ID NOS: 21

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Gly Ala Pro Val Pro Tyr Pro Asp Pro Leu Glu Pro Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Tyr Pro Tyr Asp Val Pro Asp Tyr Ala
1               5

<210> SEQ ID NO 4
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 4

Glu Gln Lys Leu Ile Ser Glu Glu Asp Leu
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Thr Lys Glu Asn Pro Arg Ser Asn Gln Glu Glu Ser Tyr Asp Asp Asn
1               5                   10                  15

Glu Ser

<210> SEQ ID NO 6
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 6

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Cys Cys Pro Gly Cys Cys
1               5

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide

<400> SEQUENCE: 8

Gly Lys Pro Ile Pro Asn Pro Leu Leu Gly Leu Asp Ser Thr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9
```

-continued

Tyr Thr Asp Ile Glu Met Asn Arg Leu Gly Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide

<400> SEQUENCE: 10

Ala His Ile Val Met Val Asp Ala Tyr Lys Pro Thr Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Lys Leu Gly Asp Ile Glu Phe Ile Lys Val Asn Lys
1               5                   10

<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 55
<212> TYPE: DNA
<213> ORGANISM: Artificial Sequence
<220> FEATURE:
<223> OTHER INFORMATION: Synthetic primer

<400> SEQUENCE: 13
aaggatgacg acgataagcc gaagaagaag cgcaaggtgg tttaaacggc cggcc       55

<210> SEQ ID NO 14
<211> LENGTH: 55
<212> TYPE: DNA
<213> ORGANISM: Artificial Sequence
<220> FEATURE:
<223> OTHER INFORMATION: Synthetic primer

<400> SEQUENCE: 14
ggccggccgt ttaaaccacc ttgcgcttct tcttcggctt atcgtcgtca tcctt       55

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
cgcaaatggg cggtaggcgt g                                            21

<210> SEQ ID NO 16
<211> LENGTH: 21

```
<212> TYPE: DNA
<213> ORGANISM: Artificial Sequence
<220> FEATURE:
<223> OTHER INFORMATION: Synthetic primer

<400> SEQUENCE: 16
accctaactg acacacattc c                                              21

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 17
auagcuaccg ugauucaucc agtgag                                         26

<210> SEQ ID NO 18
<211> LENGTH: 28
<212> TYPE: DNA
<213> ORGANISM: Artificial Sequence
<220> FEATURE:
<223> OTHER INFORMATION: Synthetic probe

<400> SEQUENCE: 18
tggatgaatc acggtagcat aaggtgca                                       28

<210> SEQ ID NO 19
<211> LENGTH: 99
<212> TYPE: DNA
<213> ORGANISM: Artificial Sequence
<220> FEATURE:
<223> OTHER INFORMATION: Synthetic oligonucleotide

<400> SEQUENCE: 19
catcgccctg gactagcata cccatgaaca caagttgcgt cacgatgaga ctggatgaat    60
cacggtagca taaggtgcac gttaccttga ttcccgtcc                           99

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
acccatgaac acaagttgcg                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
ggacgggaat caaggtaacg                                                20
```